United States Patent [19]
Scartazzini et al.

[11] Patent Number: 4,668,781
[45] Date of Patent: * May 26, 1987

[54] CEPH-3-ONE COMPOUNDS AND PROCESS FOR THEIR MANUFACTURE

[75] Inventors: Riccardo Scartazzini, Allschwil; Hans Bickel, Binningen, both of Switzerland

[73] Assignee: Ciba-Geigy Corporation, Ardsley, N.Y.

[ * ] Notice: The portion of the term of this patent subsequent to May 27, 2003 has been disclaimed.

[21] Appl. No.: 649,636

[22] Filed: Sep. 12, 1984

Related U.S. Application Data

[60] Division of Ser. No. 655,663, Feb. 5, 1976, which is a continuation-in-part of Ser. No. 373,819, Jun. 26, 1973, abandoned.

[30] Foreign Application Priority Data

Jun. 29, 1972 [CH] Switzerland .......................... 9787/72
Dec. 22, 1972 [CH] Switzerland .......................... 18721/72

[51] Int. Cl.$^4$ .................. C07D 501/04; A61K 31/545
[52] U.S. Cl. ..................................... 540/215; 540/222
[58] Field of Search ................... 544/16, 22; 540/215, 540/222

[56] References Cited

U.S. PATENT DOCUMENTS

| 3,917,587 | 11/1975 | Chauvette | 544/22 |
| 3,917,588 | 11/1975 | Chauvette | 544/22 |
| 4,389,524 | 6/1983 | Scartazzini et al. | 544/16 |
| 4,477,658 | 10/1984 | Scartazzini et al. | 544/16 |
| 4,591,642 | 5/1986 | Scartazzini et al. | 544/16 |

Primary Examiner—Nicholas S. Rizzo
Attorney, Agent, or Firm—Irving M. Fishman

[57] ABSTRACT

The invention concerns 7$\beta$-amino-cepham-3-one-4-carboxylic acid compounds, particularly esters thereof, and the N-substituted, especially N-acylated derivatives of such compounds. They can be used as intermediates, for example, for the manufacture of the corresponding enol ethers and esters, as well as the corresponding 3-unsubstituted 7$\beta$-amino-3-cephem-4-carboxylic acid compounds, which show outstanding pharmacological effects.

31 Claims, No Drawings

CEPH-3-ONE COMPOUNDS AND PROCESS FOR THEIR MANUFACTURE

CROSS REFERENCE TO RELATED APPLICATION

This is a division of application Ser. No. 655,663, filed Feb. 5, 1976 which is a continuation-in-part of Ser. No. 373,819 filed June 26, 1973 now abandoned.

The present invention relates to oxo compounds, especially 7β-amino-cepham-3-one-4-carboxylic acid compounds of the formula

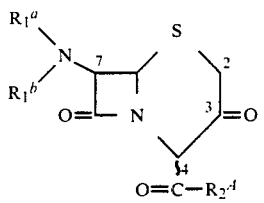

wherein $R_1^a$ represents hydrogen or an amino protective group $R_1^A$ and $R_1^b$ represents hydrogen or an acyl group Ac, or $R_1^a$ and $R_1^b$ together represent a bivalent amino protective group and $R_2^A$ represents a radical which together with the carbonyl grouping —C(=O)— forms a protected carboxyl group, or 3-ketal derivatives, as well as 1-oxides, of compounds of the formula I, or salts of such compounds having salt-forming groups, and also processes for their manufacture.

The present cepham-3-one compounds, as well as the corresponding 1-oxides, can be both in the keto form and in the enol form of the cephem-3-ol compounds of the formula

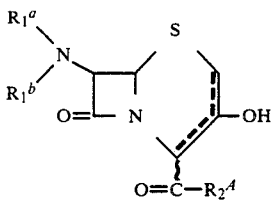

which contain a double bond in the 2,3-position or preferably in the 3,4-position, or are present as a mixture of both forms.

In compounds of the formula Ia having a double bond in the 2,3-position, the protected carboxyl group preferably has the α-configuration.

An amino protective group $R_1^A$ is a group which can be replaced by hydrogen, above all an acyl group Ac, also a triarylmethyl group, especially the trityl group, as well as an organic silyl group, and an organic stannyl group. A group Ac, which can also represent a radical $R_1^b$, above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid) and the acyl radical of a carbonic acid half-derivative.

A bivalent amino protective group formed by the radicals $R_1^a$ and $R_1^b$ together is, in particular, the bivalent acyl radical of an organic dicarboxylic acid, preferably with up to 18 carbon atoms, above all the diacyl radical of an aliphatic or aromatic dicarboxylic acid, and also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted and, for example, contains two lower alkyl groups, such as methyl groups. The radicals $R_1^a$ and $R_1^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—$R_2^A$ is above all an esterified carboxyl group but can also be an anhydride group, usually a mixed anhydride group, or an optionally substituted carbamoyl or hydrazino carbonyl group.

The group $R_2^A$ can be a hydroxyl group etherified by an organic radical, wherein the organic radical preferably contains up to 18 carbon atoms, which together with the —C(=O)— grouping forms an esterified carboxyl group. Examples of such organic radicals are aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2^A$ can also represent an organic silyloxy radical as well as a hydroxyl group etherified by an organometallic radical, such as an appropriate organic stannyloxy group, especially a silyloxy or stannyloxy group which is substituted by 1 to 3, optionally substituted hydrocarbon radicals, preferably with up to 18 carbon atoms, such as aliphatic hydrocarbon radicals, and optionally by halogen, such as chlorine.

A radical $R_2^A$ which forms a carbamoyl group with a —C(=O)— grouping is an optionally substituted amino group wherein substituents represent optionally substituted monovalent or bivalent hydrocarbon radicals, preferably with up to 18 carbon atoms, such as optionally substituted monovalent or bivalent aliphatic, cycloaliphatic, cycloaliphatic-aliphatic, aromatic or araliphatic hydrocarbon radicals with up to 18 carbon atoms, also appropriate heterocyclic or heterocyclic-aliphatic radicals with up to 18 carbon atoms and/or functional groups, such as optionally functionally modified, but especially free, hydroxyl and also etherified or esterified hydroxyl, wherein the etherifying or esterifying radicals have, for example, the abovementioned meanings and preferably containing up to 18 carbon atoms, as well as acyl radicals, above all of organic carboxylic acids and of carbonic acid half-derivatives, preferably with up to 18 carbon atoms.

In a substituted hydrazinocarbonyl group of the formula —C(=O)—$R_2^A$, one or both nitrogen atoms can be substituted, possible substituents being above all optionally substituted monovalent or bivalent hydrocarbon radicals, preferably with up to 18 carbon atoms, such as optionally substituted, monovalent or bivalent aliphatic, cycloaliphatic, cycloaliphatic-aliphatic, aromatic or araliphatic hydrocarbon radicals with up to 18 carbon atoms and also appropriate heterocyclic or heterocyclic-aliphatic radicals with up to 18 carbon atoms and/or functional groups, such as acyl radicals, above all of organic carboxylic acids or of carbonic acid half-derivatives, preferably with up to 18 carbon atoms.

The general concepts used in the preceding and following description have, for example, the following meanings:

The term "protective group" as employed in connection with functional groups, such as amino, hydroxy and carboxyl, has reference to groups commonly employed in protecting such functional groups during a reaction step and which can be split off subsequently without destroying or substantially destroying the β-lactam ring system. Such protective groups, the manner of attaching them to the functional group and the manner of their cleavage are wellknown in the art. For example, amino protective groups are described in J. F. W. Mc Omie, "Protective Groups In Organic Chemistry", Plenum Press, New York, N.Y. 1973, Chapter 2, or in E. Schröder and Lübke, "The Peptides", Vol. I, Academic Press 1965, page 72 to 74. Mc Omie, in Chapter 3, describes also hydroxy protective groups, and in Chapter 5 carboxyl protective groups. Carboxyl protective groups are also described by E. Schröder and Lübke on page 75. The terms "protected amino", "protected hydroxy", "protected carboxyl" and the like signifies amino, hydroxy or carboxyl and the like groups being protected or blocked by such protective group.

The term "optionally substituted" indicates that a group may be unsubstituted or substituted.

An aliphatic radical, including the aliphatic radical of an appropriate organic carboxylic acid, as well as an appropriate ylidene radical, is an optionally substituted monovalent or divalent aliphatic hydrocarbon radical, especially lower alkyl, as well as lower alkenyl or lower alkinyl, and also lower alkylidene which can contain, for example, up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio, phenyl-lower alkylthio, heterocyclylthio or heterocyclyl-lower alkylthio, optionally substituted lower alkoxycarbonyloxy or lower alkanoyloxy, or halogen, also by oxo, nitro, optionally substituted amino, for example lower alkylamino, di-lower alkylamino, lower alkyleneamino, oxalower alkyleneamino or aza-lower alkyleneamino, as well as acylamino, such as lower alkanoylamino, lower alkoxycarbonylamino, halogeno-lower alkoxycarbonylamino, optionally substituted phenyl-lower alkoxycarbonylamino, optionally substituted carbamoylamino, ureidocarbonylamino or guanidinocarbonylamino and also sulphoamino which is optionally present in the form of a salt, such as in the form of an alkali metal salt, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl and also optionally substituted ureidocarbonyl or guanidinocarbonyl, or nitrile, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for O-unsubstituted or O-monosubstituted phosphono to be in the form of a salt, such as in the form of an alkali metal salt.

A bivalent aliphatic radical, including the appropriate radical of a bivalent aliphatic carboxylic acid, is, for example, lower alkylene or lower alkenylene, which can optionally be monosubstituted, disubstituted or polysubstituted, for example like an aliphatic radical indicated above, and/or be interrupted by heteroatoms, such as oxygen, nitrogen or sulphur.

A cycloaliphatic or cycloaliphatic-aliphatic radical, including the cycloaliphatic or cycloaliphatic-aliphatic radical in an appropriate organic carboxylic acid or an appropriate cycloaliphatic or cycloaliphatic-aliphatic ylidene radical, is an optionally substituted, monovalent or bivalent, cycloaliphatic or cycloaliphatic-aliphatic hydrocarbon radical, for example monocyclic, bicyclic or polycyclic cycloalkyl or cycloalkenyl, and also cycloalkylidene, or cycloalkyl- or cycloalkenyl-lower alkyl or -lower alkenyl, as well as cycloalkyl-lower alkylidene or cycloalkenyl-lower alkylidene, wherein cycloalkyl and cycloalkylidene contains, for example, up to 12, such as 3–8, preferably 3–6, ring carbon atoms, whilst cycloalkenyl contains, for example, up to 12, such as 3–8, for example 5–8, preferably 5 or 6, ring carbon atoms and 1 to 2 double bonds, and the aliphatic part of a cycloaliphatic-aliphatic radical can contain, for example, up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned optionally substituted lower alkyl groups or, for example, like the abovementioned aliphatic hydrocarbon radicals, by functional groups.

An aromatic radical, including the aromatic radical of an appropriate carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

A bivalent aromatic radical, for example of an aromatic carboxylic acid, is above all 1,2-arylene, especially 1,2-phenylene, which can optionally be monosubstituted, disubstituted or polysubstituted, for example like the abovementioned aliphatic and cycloaliphatic hydrocarbon radicals.

An araliphatic radical, including the araliphatic radical in an appropriate carboxylic acid, and also an araliphatic ylidene radical, is, for example, an optionally substituted araliphatic hydrocarbon radical, such as an aliphatic hydrocarbon radical which is optionally substituted and possesses, for example, up to three optionally substituted monocyclic, bicyclic or polycyclic aromatic hydrocarbon radicals, and above all represents phenyl-lower alkyl or phenyl-lower alkenyl as well as phenyl-lower alkinyl and also phenyl-lower alkylidene, it being possible for such radicals to contain, for example, 1–3 phenyl groups and to be optionally monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, including heterocyclic or heterocyclic-aliphatic groups in appropriate carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic, or tetrazacyclic radicals of aromatic character, and also appropriate partially or wholly saturated heterocyclic radicals of this nature and such radicals can optionally be monosubstituted, disubstituted or polysubstituted, for example like the abovementioned cycloaliphatic radicals. The aliphatic part in heterocyclic-aliphatic radicals has, for example, the meaning indicated for the corresponding cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the $\alpha$- or $\beta$-position, as well as of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

An etherified hydroxyl group is above all optionally substituted lower alkoxy, wherein substituents above all represent free or functionally modified, such as etherified or esterified, hydroxyl groups, especially lower alkoxy or halogen, also lower alkenyloxy, cycloalkyloxy or optionally substituted phenyloxy, as well as heterocyclyloxy or heterocyclyl-lower alkoxy especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl, n-propyl, isopropyl, n-butyl, isobutyl, sec.-butyl or tert.-butyl, as well as n-pentyl, isopentyl, n-hexyl, isohexyl or n-heptyl, whilst lower alkenyl can, for example, be vinyl, allyl, isopropenyl, 2- or 3-methallyl or 3-butenyl, lower alkinyl can, for example, be propargyl or 2-butinyl and lower alkylidene can, for example, be isopropylidene or isobutylidene.

Lower alkylene is, for example, 1,2-ethylene, 1,2- or 1,3-propylene, 1,4-butylene, 1,5-pentylene or 1,6-hexylene, whilst lower alkenylene is, for example, 1,2-ethenylene or 2-buten-1,4-ylene. Lower alkylene interrupted by hetero-atoms is, for example, oxa-lower alkylene, such as 3-oxa-1,5-pentylene, thia-lower alkylene, such as 3-thia-1,5-pentylene, or aza-lower alkylene, such as 3-lower alkyl-3-aza-1,5-pentylene, for example 3-methyl-3-aza-1,5-pentylene.

Cycloalkyl is, for example, cyclopropyl, cyclobutyl, cyclopentyl, cyclohexyl or cycloheptyl as well as adamantyl, whilst cycloalkenyl is, for example, cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or -lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or -lower alkenyl represents, for example, 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, styryl or cinnamyl, naphthyl-lower alkyl is, for example, 1- or 2-naphthylmethyl and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl and also pyridinium, thienyl, for example 2- or 3-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, oxazacyclic, thiazacyclic or thiadiazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl, or 1,2,4- or 1,3,4-thiadiazolyl, for example 1,2,4-thiadiazol-3-yl or 1,3,4-thiadiazol-2-yl, or bicyclic diazacyclic, oxazacyclic or thiazacyclic radicals, such as benzimidazolyl, for example 2-benzimidazolyl, benzoxazolyl, for example 2-benzoxazolyl, or benzthiazolyl, for example 2-benzothiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl containing heterocyclic groups, especially those mentioned above. The abovementioned heterocyclyl radicals can be substituted, for example by optionally substituted aliphatic or aromatic hydrocarbon radicals, especially lower alkyl, such as methyl, or phenyl which is optionally substituted, for example by halogen such as chlorine, for example phenyl or 4-chlorophenyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy or tert.-pentoxy. These groups can be substituted, for example as in halogen-lower alkoxy, especially 2-halogen-lower alkoxy, for example 2,2,2-trichloroethoxy, 2-chloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentyloxy, cyclohexyloxy or adamantyloxy, phenyl-lower alkoxy is, for example, benzyloxy, 1- or 2-phenylethoxy, diphenylmethoxy or 4,4'-dimethoxydiphenylmethoxy and heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio, and phenyl-lower alkylthio is, for example, benzylthio, whilst mercapto groups etherified by heterocyclyl radicals or heterocyclyl-aliphatic radicals are especially pyridylthio, for example 4-pyridylthio, imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkanoyloxy, for example acetoxy or propionyloxy, lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxycarbonyloxy, 2-bromoethoxycarbonyloxy or 2-iodoethoxycarbonyloxy, or arylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentoxycarbonyl.

N-Lower alkyl- or N,N-di-lower alkyl-carbamoyl is, for example, N-methylcarbamoyl, N-ethylcarbamoyl, N,N-dimethylcarbamoyl or N,N-diethylcarbamoyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of a sodium or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, thia-lower alkyleneamino is, for example, thiomorpholino, and aza-lower alkyleneamino is, for example piperazino or 4-methylpiperazino. Acylamino in particular represents carbamoylamino, lower alkylcarbamoylamino, such as methylcarbamoylamino, ureidocarbonylamino, guanidinocarbonylamino, lower alkoxycarbonylamino, for example methoxycarbonylamino, ethoxycarbonylamino or tert.-butoxycarbonylamino, halogeno-lower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as acetylamino or propionylamino, and also phthalimido, or sulphoamino optionally present in the form of a salt, such as in the form of an alkali metal salt, for example in the form of a sodium salt or ammonium salt.

Lower alkanoyl is, for example, formyl, acetyl, propionyl or pivaloyl.

O-Lower alkyl-phosphono is, for example, O-methyl- or O-ethyl-phosphono, O,O'-di-lower alkyl-phosphono is, for example, O,O'-dimethyl-phosphono or O,O'-diethylphosphono, O-phenyl-lower alkyl-phosphono is, for example, O-benzyl-phosphono, and O-lower alkyl-O'-phenyl-lower alkyl-phosphono is, for example, O-benzyl-O'-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, 4-methoxy-benzyloxycarbonyl, diphenylmethoxycarbonyl or α-4-biphenylyl-α-methyl-ethoxycarbonyl. Lower alkoxycarbonyl, wherein lower alkyl contains, for example, a monocyclic, monoazacyclic, monooxacyclic or monothiacyclic group, is, for example, furyl-lower alkoxycarbonyl, such as furfuryloxycarbonyl, or thienyl-lower alkoxycarbonyl, such as 2-thenyloxycarbonyl.

2-Lower alkylhydrazino and 2,2-di-lower alkylhydrazino are, for example, 2-methylhydrazino or 2,2-dimethylhydrazino, 2-lower alkoxycarbonylhydrazino is, for example 2-methoxycarbonylhydrazino, 2-ethoxycarbonylhydrazino or 2-tert.-butoxycarbonylhydrazino and lower alkanoylhydrazino is, for example, 2-acetylhydrazino.

An acyl group Ac in particular represents an acyl radical of an organic carboxylic acid, preferably with up to 18 carbon atoms, contained in a naturally occurring or biosynthetically, semi-synthetically or total-synthetically obtainable, preferably pharmacologically active, N-acetyl derivative of a 6-amino-penam-3-carboxylic acid compound or 7-amino-3-cephem-4-carboxylic acid compound, or represents an easily removable acyl radical, especially of a carbonic acid half-derivative.

An acyl radical Ac contained in a pharmacologically active N-acyl derivative of a 6-amino-penam-3-carboxylic acid compound or 7-amino-3-cephem-4-carboxylic acid compound is above all a group of the formula

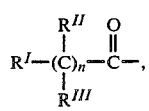
(A)

wherein n represents 0 and $R^I$ denotes hydrogen or an optionally substituted cycloaliphatic or aromatic hydrocarbon radical or an optionally substituted heterocyclic radical, preferably of aromatic character, a functionally modified, for example esterified or etherified, hydroxyl or mercapto group or an optionally substituted amino group, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, an optionally functionally modified, preferably etherified or esterified, hydroxyl or mercapto group, an optionally functionally modified carboxyl group, an acyl group, an optionally substituted amino group or an azido group and each of the radicals $R^{II}$ and $R^{III}$ represents hydrogen, or wherein n represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably has aromatic character, $R^{II}$ denotes an optionally functionally modified, for example esterified or etherified, hydroxyl or mercapto group, such as a halogen atom, an optionally substituted amino group, an optionally functionally modified carboxyl or sulpho group, an optionally O-monosubstituted or O,O'-disubstituted phosphono group or an azido group, whereby $R^{II}$ cannot be an optionally substituted amino group, when $R^{I}$ is 1,4-cyclohexadienyl, and $R^{III}$ represents hydrogen, or wherein n represents 1, each of the radicals $R^{I}$ and $R^{II}$ denotes a functionally modified, preferably etherified or esterified, hydroxyl group or an optionally functionally modified carboxyl group, and $R^{III}$ represents hydrogen, or wherein n represents 1, $R^{I}$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein n represents 1 and $R^{I}$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

An acyl group of the formula A can for example be a group of the formula

(A₁)

wherein $R^{I}$ represents hydrogen or a cycloalkyl group with 5–7 ring carbon atoms which is optionally substituted, preferably in the 1-position, by optionally protected amino, such as amino, acylamino, wherein acyl above all represents the acyl radical of a carbonic acid half-ester, such as a lower alkoxycarbonyl, 2-halogeno-lower alkoxycarbonyl or phenyl-lower alkoxycarbonyl radical, or a sulphoamino group which is optionally present in the form of a salt, for example in the form of an alkali metal salt, a phenyl, naphthyl or tetrahydronaphthyl group which is optionally substituted, preferably by hydroxyl, lower alkoxy, for example methoxy, acyloxy, wherein acyl above all represents the acyl radical of a carbonic acid half-ester, such as a lower alkoxycarbonyl, 2-halogeno-lower alkoxycarbonyl or phenyl-lower alkoxycarbonyl radical, and/or halogen, for example chlorine, a heterocyclic group which is optionally substituted, for example by lower alkyl, for example methyl and/or phenyl, which can in turn carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine, or an acyl group of the formula (A) can be an acyl group of the formula

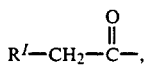

(A₂)

wherein $R^{I}$ represents a lower alkyl group which is optionally substituted, preferably by halogen, such as chlorine, by phenyloxy which is optionally substituted, such as phenyloxy containing hydroxyl, acyloxy, wherein acyl has the abovementioned meaning, and/or halogen, for example chlorine, or by optionally protected amino and/or carboxyl, for example a 3-amino-3-carboxyl-propyl radical which has an optionally protected amino and/or carboxyl group, for example a silylated, such as tri-lower alkylsilylated, for example trimethylsilylated, amino or acylamino, such as lower alkanoylamino, halogeno-lower alkanoylamino or phthaloylamino group, and/or a silylated, such as tri-lower alkylsilylated, for example trimethylsilylated, carboxyl group, or an esterified carboxyl group, such as a carboxyl group which is esterified by lower alkyl, 2-halogeno-lower alkyl or phenyl-lower alkyl, for example diphenylmethyl, or represents a lower alkenyl group, a phenyl group which is optionally substituted, such as a phenyl group which optionally contains hydroxyl which is acylated, for example as indicated above, and/or halogen, for example chlorine, and also optionally protected amino-lower alkyl, such as aminomethyl, which is optionally protected, for example acylated as indicated above, or phenyloxy which is optionally substituted, such as phenyloxy which possesses hydroxyl which is optionally acylated, for example as indicated above, and/or halogen, for example chlorine, or represents a pyridyl group, for example 4-pyridyl group, pyridinium group, for example 4-pyridinium group, thienyl group, for example 2-thienyl group, furyl group, for example 2-furyl group, imidazolyl group, for example 1-imidazolyl group, or tetrazolyl group, for example 1-tetrazolyl group, which are optionally substituted, for example by lower alkyl, such as methyl, or by amino or aminomethyl which are optionally protected, for example acylated as indicated above, or represents an optionally substituted lower alkoxy group, for example a methoxy group, a phenyloxy group which is optionally substituted, such as a phenyloxy group which contains optionally protected hydroxyl, for example hydroxyl acylated as indicated above, and/or halogen, such as chlorine, or represents a lower alkylthio group, for example n-butylthio group, or lower alkenylthio group, for example allylthio group, a phenylthio, pyridylthio, for example 4-pyridylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as 5-methyl-1,3,4-thiadiazol-2-ylthio, or 5-tetrazolylthio, such as 1-methyl-5-tetrazolylthio group, which are optionally substituted, for example by lower alkyl, such as methyl, or represents a halogen atom, especially chlorine or bromine atom, an optionally functionally modified carboxyl group, such as lower alkoxycarbonyl, for example methoxycarbonyl or ethoxycarbonyl, nirile or carbamoyl which is optionally N-substituted, for example by lower alkyl, such as methyl, or phenyl, or represents an optionally substituted lower alkanoyl group, for example an acetyl or propionyl group, or a benzoyl group, or an azido group, or an acyl group of the formula (A) can be an acyl group of the formula

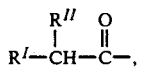

(A₃)

wherein R^I represents lower alkyl or a phenyl, furyl, for example 2-furyl, thienyl, for example 2- or 3-thienyl, or isothiazolyl, for example 4-isothiazolyl group which is optionally substituted, such as substituted by hydroxyl which is optionally acylated, for example as indicated above, and/or by halogen, for example chlorine, R^II represents optionally protected or substituted amino, for example amino, acylamino, such as lower alkoxycarbonylamino, 2-halogeno-lower alkoxycarbonylamino or optionally substituted phenyl-lower alkoxycarbonylamino such as phenyl-lower alkoxycarbonylamino which contains lower alkoxy, for example methoxy, or nitro, for example tert.-butoxycarbonylamino, 2,2,2,-trichloroethoxycarbonylamino, 4-methoxybenzyloxycarbonylamino or diphenylmethyloxycarbonylamino, arylsulphonylamino, for example 4-methylphenylsulphonylamino, tritylamino, arylthioamino, such as nitrophenylthioamino, for example 2-nitrophenylthioamino, or tritylthioamino or 2-propylideneamino which is optionally substituted, such as 2-propylideneamino which contains lower alkoxycarbonyl, for example ethoxycarbonyl, or lower alkanoyl, for example acetyl, such as 1-ethoxycarbonyl-2-propylideneamino, or optionally substituted carbamoylamino, such as guanidinocarbonylamino, or a sulphoamino group which is optionally present in the form of a salt, for example in the form of an alkali metal salt, an azido group, a carboxyl group which is optionally present in the form of a salt, for example in the form of an alkali metal salt, or in a protected form, such as in an esterified form, for example as a lower alkoxycarbonyl group, for example a methoxycarbonyl group or ethoxycarbonyl group, or as a phenyloxycarbonyl group, for example a diphenylmethoxycarbonyl group, a nitrile group, a sulpho group, an optionally functionally modified hydroxyl group, wherein functionally modified hydroxyl in particular represents protected hydroxyl, for example acyloxy, such as formyloxy, as well as lower alkoxycarbonyloxy, 2-halogeno-lower alkoxycarbonyloxy or phenyl-lower alkoxycarbonyloxy which is optionally substituted, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy or phenyloxy, a O-lower alkyl-phosphono group or O,O'-di-lower alkyl-phosphono group, for example O-methyl-phosphono or O,O'-dimethylphosphono, or a halogen atom, for example chlorine or bromine, whereby R^I can also be 1,4-cyclohexadienyl, if R^II is a carboxyl group which is optionally present in the form of a salt, for example in the form of an alkali metal salt, or in a protected form, such as in an esterified form, for example as a lower alkoxycarbonyl group, for example a methoxycarbonyl group or ethoxycarbonyl group, or as a phenyloxycarbonyl group, for example a diphenylmethoxycarbonyl group, a nitrile group, a sulpho group, an optionally functionally modified hydroxyl group, wherein functionally modified hydroxyl in particular represents protected hydroxyl, for example acyloxy, such as formyloxy, as well as particular represents acyloxy, such as formyloxy, as well as lower alkoxycarbonyloxy, 2-halogeno-lower alkoxycarbonyloxy or phenyl-lower alkoxycarbonyloxy which is optionally substituted, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy or phenyloxy, a O-lower alkyl-phosphono group or O,O'-di-lower alkyl-phosphono group, for example O-methyl-phosphono or O,O'-dimethylphosphono, or a halogen atom, for example chlorine or bromine, or an acyl group of the formula (A) can be an acyl group of the formula

wherein R^I and R^II each represent halogen, for example bromine, or lower alkoxycarbonyl, for example methoxycarbonyl, or an acyl group of the formula (A) can be an acyl group of the formula

wherein R^I represents phenyl, furyl, for example 2-furyl, or thienyl, for example 2- or 3-thienyl, or isothiazolyl, for example 4-isothiazolyl, which are optionally substituted, for example by hydroxyl which is optionally acylated, for example as indicated above, and/or by halogen, for example chlorine, and also represents a 1,4-cyclohexadienyl group, R^II represents aminomethyl which is optionally protected, for example as indicated above, or an acyl group of the formula (A) can be an acyl group of the formula

wherein each of the groups R^I, R^II and R^III represents lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the form of a salt, or an amino group which is substituted by an acyl radical which can be split off, preferably easily, for example on treatment with an acid agent, such as trifluoroacetic acid, or by reduction, for example on treatment with a chemical reducing agent, such as zinc in the presence of aqueous acetic acid, or catalytic hydrogen, or hydrolytically, or an acyl radical which can be converted into such a radical, preferably a suitable acyl radical of a carbonic acid half-ester, such as lower alkoxycarbonyl, for example tert.-butoxycarbonyl, 2-halogeno-lower alkylcarbonyl, for exaple 2,2,2-trichloroethoxycarbonyl, 2-bromoethoxycarbonyl or 2-iodoethoxycarbonyl, arylcarbonylmethoxycarbonyl, for example phenacyloxycarbonyl, optionally substituted phenyl-lower alkoxycarbonyl, such as phenyl-lower alkoxycarbonyl containing lower alkoxy, for example methoxy, or nitro, for example 4-methoxybenzyloxycarbonyl or diphenylmethoxycarbonyl, or of a carbonic acid half-amide, such as carbamoyl or N-substituted carbamoyl, such as N-lower alkylcarbamoyl, for example N-methylcarbamoyl, as well as by trityl, also by arylthio, for example 2-nitrophenylthio, arylsulphonyl, for example 4-methylphenylsulphonyl or 1-lower alkoxycarbonyl-2-propylidene, for example 1-ethoxycarbonyl-2-propylidene), 2,6-dimethoxybenzoyl, 5,6,7,8-tetrahydronaphthoyl, 2-methoxy-1-naphthoyl, 2-ethoxy-1-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, pivaloyl, hexanoyl, octanoyl, acrylyl, crotonyl, 3-butenoyl, 2-pentenoyl, methoxyacetyl, butylthioacetyl, allylthioacetyl, methylthioacetyl, chloroacetyl, bromoacetyl, dibromoacetyl, 3-chloropropionyl, 3-bromopropionyl, aminoacetyl or 5-amino-5-carboxy-valeryl (with an amino group which is optionally substituted, for example as indicated, such as substituted by a monoacyl or diacyl radical, for example an optionally halogenated lower alkanoyl radical, such as acetyl or dichloroacetyl, or phthaloyl, and/or with an optionally functionally modified carboxyl group, for example a carboxyl group present in the form of a salt, such as a sodium salt, or in the form of an ester, such as a lower alkyl ester, for example a methyl or ethyl ester, or an aryl-lower alkyl ester, for example diphenylmethyl ester), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethylacrylyl, phenylacetyl, α-bromophenylacetyl, α-azidophenylacetyl, 3-chlorophenylacetyl, 2- or 4-aminomethylphenyl-acetyl (with an amino group which is optionally substituted, for example, as indicated), phenacylcarbonyl, phenoxyacetyl, 4-trifluoromethylphenoxyacetyl, benzyloxyacetyl, phenylthioacetyl, bromophenylthioacetyl, 2-phenoxypropionyl, α-phenoxyphenylacetyl, α-methoxyphenylacetyl, α-ethoxyphenylacetyl, α-methoxy-3,4-dichlorophenylacetyl, α-cyano-phenylacetyl, especially phenylglycyl, 4-hydroxyphenylglycyl, 3-chloro-4-hydroxyphenylglycyl, 3,5-dichloro-4-hydroxy-phenylglycyl, α-aminomethyl-α-phenylacetyl or α-hydroxyphenylacetyl, (it being possible, in these radicals, for an amino group which is present to be optionally substituted, for example as indicated above, and/or an aliphatic and/or phenolically bonded hydroxyl group which is present to be optionally protected, analogously to the amino group, for example by a suitable acyl radical, especially by formyl or by an acyl radical of a carbonic acid half-ester), or α-O-methyl-phosphonophenylacetyl or α-O,O-dimethyl-phosphono-phenylacetyl, also benzylthioacetyl, benzylthiopropionyl, α-carboxyphenylacetyl (with a carboxy group which is optionally functionally modified, for example as indicated above), 3-phenylpropionyl, 3-(3-cyanophenyl)-propionyl, 4-(3-methoxyphenyl)-butyryl, 2-pyridylacetyl, 4-amino-pyridiniumacetyl (optionally with an amino group which is substituted, for example as indicated above), 2-thienylacetyl, 3-thienylacetyl, 2-tetrahydrothienylacetyl, 2-furylacetyl, 1-imidazolylacetyl, 1-tetrazolylacetyl, α-carboxy-2-thienylacetyl or α-carboxy-3-thienylacetyl (optionally with a carboxyl group which is functionally modified, for example as indicated above), α-cyano-2-thienylacetyl, α-amino-α-(2-thienyl)-acetyl, α-amino-α-(2-furyl)acetyl or α-amino-α-(4-isothiazolyl)-acetyl (optionally with an amino group which is substituted, for example as indicated above), α-sulphophenylacetyl (optionally with a sulpho group which is functionally modified, for example like the carboxyl group), 3-methyl-2-imidazolylthioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl group which preferably has multiple branching and/or an aromatic substituent on the carbon atom in the α-position to the oxy group, or a methoxycarbonyl group which is substituted by arylcarbonyl, especially benzoyl, radicals, or a lower alkoxycarbonyl radical which is substituted in the β-position by halogen atoms, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position is preferably polysubstituted, for example diphenylmethoxycarbonyl or α4-biphenylyl-α-methylethoxycarbonyl, or furyl-lower alkoxycarbonyl, above all α-furyl-lower alkoxycarbonyl, for example furfuryloxycarbonyl.

A bivalent acyl group formed by the two radicals $R_1^A$ and $R_1^b$ is, for example, the acyl radical of a lower alkanedicarboxylic acid or lower alkendicarboxylic acid, such as succinyl, or an o-arylenedicarboxylic acid, such as phthaloyl.

A further bivalent radical formed by the groups $R_1^A$ and $R_1^b$ is, for example, a 1-oxo-3-aza-1,4-butylene radical which is substituted, especially in the 2-position and contains, for example, optionally substituted phenyl or thienyl, and is optionally monosubstituted or disubstituted by lower alkyl, such as methyl, in the 4-position, for example 4,4-dimethyl-2-phenyl-1-oxo-3-aza-1,4-butylene.

An etherified hydroxyl group $R_2^A$ forms, together with the carbonyl grouping, an esterified carboxyl group which can preferably be split easily or can be converted easily into another functionally modified carboxyl group, such as into a carbamoyl or hydrazinocarbonyl group. Such a group $R_2^A$ is, for example, lower alkoxy, such as methoxy, ethoxy, n-propoxy or isopropoxy, which, together with the carbonyl grouping, forms an esterified carboxyl group, which can easily be converted, especially in 2-cephem compounds, into a free carboxyl group or into another functionally modified carboxyl group.

An etherified hydroxyl group $R_2^A$ which together with a —C(=O)— grouping forms an esterified carboxyl group which can be split particularly easily represents, for example, 2-halogeno-lower alkoxy, wherein halogen preferably has an atomic weight above 19. Such a radical forms, together with the —C(=O)— grouping, an esterified carboxyl group which can easily be split on treatment with chemical reducing agents under neutral or weakly acid conditions, for example with zinc in the presence of aqueous acetic acid, or an esterified carboxyl group which can easily be converted into such a group and is, for example, 2,2,2-trichloroethoxy or 2-iodoethoxy, also 2-chloroethoxy or 2-bromoethoxy, which can easily be converted into the latter.

An etherified hydroxyl group $R_2^A$ which together with the —C(=O)— grouping represents an esterified carboxyl group which can also be split easily on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^A$ can also represent an arylmethoxy group wherein aryl in particular denotes a monocyclic, preferably substituted, aromatic hydrocarbon radical. Such a radical forms, together, with the —C(=O)— grouping, an esterified carboxyl group which can easily be split on irradiation, preferably with ultraviolet light, under neutral or acid conditions. An aryl radical in such an arylmethoxy group is in particular lower alkoxyphenyl, for example methoxyphenyl (wherein methoxy above all is in the 3-, 4- and/or 5position) and/or above all nitrophenyl (wherein nitro is preferably in the 2-position). Such radicals are, in particular, lower alkoxy-benzyloxy, for example methoxy-benzyloxy, and/or nitrobenzyloxy, above all 3- or 4-methoxy-benzyloxy, 3,5-dimethoxybenzyloxy, 2-nitro-benzyloxy or 4,5-dimethoxy-2-nitro-benzyloxy.

An etherified hydroxyl group $R_2^A$ can also represent a radical which, together with the —C(=O)— grouping, forms an esterified carboxyl group which can easily be split under acid conditions, for example on treatment with trifluoroacetic acid or formic acid. Such a radical is above all a methoxy group in which methyl is polysubstituted by optionally substituted hydrocarbon radicals, especially aliphatic or aromatic hydrocarbon radicals, such as lower alkyl, for example methyl, and/or phenyl, or is monosubstituted by a carbocyclic aryl group possessing electron-donating substituents or by a heterocyclic group of aromatic character possessing oxygen or sulphur as a ring member, or in which methyl denotes a ring member in a polycycloaliphatic hydrocarbon radical or denotes the ring member which represents the α-position to the oxygen or sulphur atom in an oxacycloaliphatic or thiacycloaliphatic radical.

Preferred polysubstituted methoxy groups of this nature are tert.-lower alkoxy, for example tert.-butoxy or tert.-pentoxy, optionally substituted diphenylmethoxy, for example diphenylmethoxy or 4,4'-dimethoxydiphenylmethoxy, and also 2-(4-biphenylyl)-2-propoxy, whilst a methoxy group which contains the abovementioned substituted aryl group or the heterocyclic group is, for example, α-lower alkoxy-phenyl-lower alkoxy, such as 4-methoxybenzyloxy or 3,4-dimethoxybenzyloxy, or furfuryloxy, such as 2-furfuryloxy. A polycycloaliphatic hydrocarbon radical in which the methyl of the methoxy group represents a branched, preferably triply branched, ring member, is, for example, adamantyl, such as 1-admantyl, and an abovementioned oxacycloaliphatic or thiacycloaliphatic radical wherein the methyl of the methoxy group is the ring member which represents the α-position to the oxygen atom or sulphur atom, denotes, for example, 2-oxa-or 2-thia-lower alkylene or -lower alkenylene with 5–7 ring atoms, such as 2-tetrahydrofuryl, 2-tetrahydropropyranyl (sic) or 2,3-dihydro-2-pyranyl or corresponding sulphur analogues.

The radical $R_2^A$ can also represent an etherified hydroxyl group which, together with the —C(=O)— grouping forms an esterified carboxyl group which can be split hydrolytically, for example under weakly basic or weakly acid conditions. Such a radical is, preferably, an etherified hydroxyl group which forms an activated ester group with the —C(=O)— grouping, such as nitrophenyloxy, for example 4-nitrophenyloxy or 2,4-dinitrophenyloxy, nitrophenyl-lower alkoxy, for example 4-nitro-benzyloxy, hydroxy-lower alkylbenzyloxy, for example 4-hydroxy-3,5-tert.-butyl-benzyloxy, polyhalogenophenyloxy, for example 2,4,6-trichlorophenyloxy or 2,3,4,5,6-pentachlorophenyloxy, and also cyanomethoxy, as well as acylaminomethoxy, for example phthaliminomethoxy or succinyliminomethoxy.

The group $R_2^A$ can also represent an etherified hydroxyl group which, together with the carbonyl grouping of the formula —C(=O)—, forms an esterified carboxyl group which can be split under hydrogenolytic conditions and is, for example, α-phenyl-lower alkoxy, which is optionally substituted, for example by lower alkoxy or nitro, such as benzyloxy, 4-methoxybenzyloxy or 4-nitrobenzyloxy.

the group $R_2^A$ can also be an etherified hydroxyl group which, together with the carbonyl grouping —C(=O)—, forms an esterified carboxyl group which can be split under physiological conditions, above all an acyloxymethoxy group, wherein acyl denotes, for example, the radical of an organic carboxylic acid, above all of an optionally substituted lower alkanecarboxylic acid, or wherein acyloxymethyl forms the residue of a lactone. Hydroxyl groups etherified in this way are lower alkanoyloxymethoxy, for example acetoxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy and also phthalidyloxy.

A silyloxy or stannyloxy group $R_2^A$ preferably contains, as substituents, optionally substituted aliphatic, cycloaliphatic aromatic or araliphatic hydrocarbon radicals, such as lower alkyl, halogeno-lower alkyl, cycloalkyl, phenyl or phenyl-lower alkyl groups, or optionally modified functional groups, such as etherified hydroxyl groups, for example lower alkoxy groups, or halogen atoms, for example chlorine atoms, and above all represents tri-lower alkylsilyloxy, for example trimethylsilyloxy, halogeno-lower alkoxy-lower alkylsilyl, for example chloromethoxymethylsilyl, or tri-lower alkylstannyloxy, for example tri-n-butylstannyloxy.

A radical $R_2^A$ which, together with a —C(=O)— grouping, forms an optionally substituted carbamoyl or hydrazinocarbonyl group is, for example, amino, lower alkylamino or di-lower alkylamino, such as methylamino, ethylamino, dimethylamino or diethylamino, lower alkyleneamino, for example pyrrolidino or piperidino, oxa-lower alkyleneamino, for example morpholino, hydroxylamino, hydrazino, 2-lower alkylhydrazino or 2,2-di-lower alkylhydrazino, for example 2-methylhydrazino or 2,2-dimethylhydrazino.

Salts are, for example, those of compounds of the formula I having an acid grouping, such as a carboxyl, sulpho or phosphono group, above all metal salts or ammonium salts, such as alkali metal salts alkaline earth metal salts; for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzyl-ethylenediamine, and also bases of the pyridine type, for example pyridine, collidine or quinoline. Compounds of the formula I which possess a basic group can also form acid addition salts, for example with inorganic acids, such as hydrochloric acid, sulphuric acid or phosphoric acid, or with suitable organic carboxylic acids or sulphonic acids, for example trifluoroacetic acid or 4-methylphenylsulphonic acid. Compounds of the formula I having an acid group and a basic group can also be in the form of internal salts, that is to say in the form of a zwitterion. 1-Oxides of compounds of the formula I having salt-forming groups can also form salts, as described above.

The new compounds of the present invention are valuable intermediate products which can be used for the manufacture of compounds having pharmacological properties; they can be converted into these, for example, as described below.

The invention in particular relates to the cepham-3-one compounds of the formula I, wherein $R_1{}^a$ denotes hydrogen or preferably an acyl radical contained in a fermentatively obtainable (that is to say naturally occurring) or biosynthetically, semi-synthetically or total-synthetically obtainable, in particular pharmacologically active, such as highly active, N-acyl derivative of a 6β-amino-penam-3-carboxylic acid compound or 7β-amino-3-cephem-4-carboxylic acid compound, such as one of the abovementioned acyl radicals of the formula A, in which $R^I$, $R^{II}$, $R^{III}$ and n above all have the preferred meanings, $R_1{}^b$ represents hydrogen, or wherein $R_1{}^a$ and $R_1{}^b$ together represent a 1-oxo-3-aza-1,4-butylene radical which is preferably substituted in the 2-position, for example by an aromatic or heterocyclic radical, such as phenyl, and preferably substituted in the 4-position, for example by two lower alkyl, such as methyl, and $R_2{}^A$ represents lower alkoxy which is optionally monosubstituted or polysubstituted, preferably in the α-position, for example by optionally substituted aryloxy, such as lower alkoxyphenyloxy, for example 4-methoxyphenyloxy, lower alkanoyloxy, for example acetoxy or pivaloyloxy, α-amino-lower alkanoyloxy, for example glycyloxy, L-valyloxy or L-leucyloxy, arylcarbonyl, for example benzoyl, or optionally substituted aryl, such as phenyl, lower alkoxyphenyl, for example 4-methoxyphenyl, nitrophenyl, for example 4-nitrophenyl, or biphenylyl, for example 4-biphenylyl, or is monosubstituted or polysubstituted in the β-position by halogen, for example, chlorine, bromine or iodine, such as lower alkoxy, for example methoxy, ethoxy, n-propoxy, isopropoxy, n-butoxy, tert.-butoxy or tert.-pentoxy, bis-phenyloxy-methoxy which is optionally substituted by lower alkoxy, for example bis-4-methoxyphenyloxy-methoxy, lower alkanoyloxy-methoxy, for example acetoxymethoxy or pivaloyloxymethoxy, α-amino-lower alkanoyloxy-methoxy, for example glycyloxymethoxy, phenacyloxy, optionally substituted phenyl-lower alkoxy, especially 1-phenyl-lower alkoxy, such as phenylmethoxy, with such radicals being able to contain 1–3 phenyl radicals which are optionally substituted, for example by lower alkoxy, such as methoxy, nitro or phenyl, for example benzyloxy, 4-methoxy-benzyloxy, 2-biphenylyl-2-propoxy, 4-nitro-benzyloxy, diphenylmethoxy, 4,4'-dimethoxydiphenylmethoxy or trityloxy, or 2-halogeno-lower alkoxy, for example 2,2,2-trichloroethoxy, 2-chloroethoxy, 2-bromoethoxy or 2-iodoethoxy, and also 2-phthalidyloxy, tri-lower alkylsilyloxy, for example trimethylsilyloxy, or amino or hydrazino which is optionally substituted, for example, by lower alkyl, such as methyl, or hydroxyl, for example amino, lower akylamino or di-lower alkylamino, such as methylamino or dimethylamino, hydrazino, 2-lower alkylhydrazino or 2,2-di-lower alkylhydrazino, for example 2-methylhydrazino or 2,2-dimethylhydrazino, or hydroxyamino, as well as the 1-oxides thereof, or salts of such compounds having salt-forming groups.

Above all, in a cepham-3-one compound of the formula I, and also in a 1-oxide of a cepham-3-one compound of the formula I, or in a salt of such a compound having salt-forming groups, $R_1{}^a$ represents hydrogen or an acyl radical contained in fermentatively obtainable (that is to say naturally occurring) or biosynthetically obtainable N-acyl derivatives of 6β-amino-penam-3-carboxylic acid compounds or 7β-amino-3-cephem-4-carboxylic acid compounds, especially of the formula A, wherein $R^I$, $R^{II}$ and $R^{III}$ and n above all have the preferred meanings, such as a phenylacetyl or phenyloxyacetyl radical which is optionally substituted, for example by hydroxyl, also a lower alkanoyl or lower alkenoyl radical which is optionally substituted, for example by lower alkylthio, or lower alkenylthio, as well as by optionally substituted, such as acylated, amino and/or functionally modified, such as esterified, carboxyl, for example 4-hydroxy-phenylacetyl, hexanoyl, octanoyl or n-butylthioacetyl, and especially 5-amino-5-carboxy-valeryl, wherein the amino and/or the carboxyl groups are optionally protected and are present, for example, as acylamino or esterified carboxyl, phenylacetyl or phenyloxyacetyl, or an acyl radical occurring in highly active N-acyl derivatives of 6β-amino-penam-3-carboxylic acid compounds or 7β-amino-3-cephem-4-carboxylic acid compounds, especially of the formula A, wherein $R^I$, $R^{II}$, $R^{III}$ and n above all have the preferred meanings, such as formyl, 2-halogenoethylcarbamoyl, for example 2-chloroethylcarbamoyl, cyanoacetyl, phenylacetyl, thienylacetyl, for example 2-thienylacetyl, or tetrazolylacetyl, for example 1-tetrazolylacetyl, but especially acetyl substituted in the α-position by a cyclic, such as a cycloaliphatic, aromatic or heterocyclic, above all monocyclic, radical and by a functional group, above all amino, carboxyl, sulpho or hydroxyl groups, especially phenylglycyl, wherein phenyl represents phenyl which is optionally substituted, for example by optionally protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxyphenyl (optionally also with a protected hydroxyl group, such as an acylated hydroxyl group), and wherein the amino group can also optionally be substituted and represents, for example, a sulphoamino group optionally present in the form of a salt, or an amino group which contains, as a substituent, a hydrolytically removable trityl group or above all an acyl group, such as an optionally substituted carbamoyl group, such as an optionally substituted ureidocarbonyl group, for example ureidocarbonyl or N'-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or reductively, such as on treatment with a chemical reducing agent, such as zinc in the presence of aqueous acetic acid, or with catalytic hydrogen, or hydrolytically, or an acyl radical which can be converted into such a radical, preferably a suitable acyl radical of a carbonic acid half-ester, such as one of the abovementioned, for example optionally halogen-substituted or benzoyl-substituted, lower alkoxycarbonyl radicals, for example tert.-butoxycarbonyl, 2,2,2-trichloroethoxycarbonyl, 2-chloroethoxycarbonyl, 2-bromoethoxycarbonyl, 2-iodoethoxycarbonyl or phenacyloxycarbonyl, optionally lower alkoxy-substituted or nitro-substituted phenyl-lower alkoxycarbonyl, for example 4-methoxybenzyloxycarbonyl or diphenylmethoxycarbonyl, or a suitable acyl radical of a carbonic acid half-amide, such as carbamoyl or N-methylcarbamoyl, or an arylthio or aryl-lower alkylthio radical which can be split off with a nucleophilic reagent, such as hydrocyanic acid, sulphurous acid or thioacetic acid amide, for example 2-nitrophenylthio or tritylthio, an arylsulphonyl radical which can be split off by means of electrolytic reduction, for example 4-methylphenylsulphonyl, or a 1-lower alkoxycarbonyl or 1-lower alkanoyl-2-pyropylidene radical which can be split off with an acid agent, such as formic acid or aqueous mineral acid, for example hydrochloric acid or phosphoric acid, for example 1-ethoxycarbonyl-2-propylidene, α-thienyl-glycyl, such as α-2- or α-3-thienylglycyl, α-furylglycyl, such as α-2-furylglycyl, α-isothiazolylglycyl, such as α-4-isothiazolyl-glycyl, it being possible for the amino group in such radicals to be substituted or protected, for example as indicated for a phenylglycyl radical, also α-carboxy-phenylacetyl or α-carboxy-thienylacetyl, for example α-carboxy-2-thienylacetyl (optionally with a functionally modified carboxyl group, for example a carboxyl group present in the form of a salt, such as a sodium salt, or in the form of an ester, such as a lower alkyl ester, for example methyl or ethyl ester, or phenyl-lower alkyl ester, for example diphenylmethyl ester), α-sulpho-phenylacetyl (optionally also with a sulpho group which is functionally modified, for example like the carboxyl group), α-phosphono-, α-O-methylphosphono- or α-O,O'-dimethyl-phosphono-phenylacetyl, or α-hydroxy-phenylacetyl (optionally with a functionally modified hydroxyl group, especially with an acyloxy group, wherein acyl denotes an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as one of the above-mentioned lower alkoxycarbonyl radicals which are, for example, optionally substituted by halogen or benzoyl, for example 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, and also formyl), as well as 1-amino-cyclohexylcarbonyl, aminomethyl-phenylacetyl, such as 2- or 4-aminomethylphenylacetyl, or amino-pyridiniumacetyl, for example 4-aminopyridiniumacetyl (optionally also with an amino group which is substituted, for example as indicated above), or pyridylthioacetyl, for example 4-pyridylthioacetyl, and $R_1^b$ represents hydrogen, or $R_1^a$ and $R_1^b$ together represent a 1-oxo-3-aza-1,4-butylene radical which is preferably substituted in the 2-position by phenyl which is optionally substituted by protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxy-phenyl (optionally also with a hydroxyl group which is protected, for example acylated as indicated above), and which optionally contains two lower alkyl, such as methyl, in the 4-position, and $R_2^A$ represents lower alkoxy, especially α-poly-branched lower alkoxy, for example tert.-butoxy, also methoxy or ethoxy, 2-halogeno-lower alkoxy, for example 2,2,2-trichloroethoxy, 2-iodoethoxy or 2-chloroethoxy or 2-bromoethoxy which can easily be converted into 2-iodoethoxy, phenacyloxy, 1-phenyl-lower alkoxy with 1–3 phenyl radicals which are optionally substituted by lower alkoxy or nitro, for example 4-methoxybenzyloxy, 4-nitrobenzyloxy, diphenylmethoxy, 4,4'-dimethoxy-diphenylmethoxy or trityloxy, lower alkanoyloxymethoxy, for example acetoxymethoxy or pivaloyloxymethoxy, α-amino-lower alkanoyloxymethoxy, for example glycyloxymethoxy, 2-phthalidyloxymethoxy, and also tri-lower alkylsilyloxy, for example trimethylsilyloxy.

The invention above all relates to cephem-3-one compounds of the formula I, wherein $R_1^a$ denotes hydrogen or an acyl group of the formula

(B)

wherein $R_a$ denotes phenyl or hydroxyphenyl, for example 3- or 4-hydroxyphenyl, also hydroxy-chlorophenyl, for example 3-chloro-4-hydroxyphenyl or 3,5-dichloro-4-hydroxy-phenyl, it being possible for hydroxy substituents in such radicals to be protected by acyl radicals, such as optionally halogenated lower alkoxycarbonyl radicals, for example tert.-butoxycarbonyl or 2,2,2-trichloroethoxycarbonyl, as well as thienyl, for example 2- or 3-thienyl, and also pyridyl, for example 4-pyridyl, aminopyridinium, for example 4-aminopyridinium, furyl, for example 2-furyl, isothiazolyl, for example 4-isothiazolyl, or tetrazolyl, for example 1-tetrazolyl, X represents oxygen or sulphur, m represents 0 or 1 and $R_b$ represents hydrogen, or, if m represents 0, $R_b$ represents amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino or diphenylmethoxycarbonylamino, or 3-guanylureido, also sulphoamino or tritylamino, as well as arylthioamino, for example 2-nitrophenylthioamino, arylsulphonylamino, for example 4-methylphenylsulphonylamino, or 1-lower alkoxycarbonyl-2-propylideneamino, for example 1-ethoxycarbonyl-2- propylideneamino, carboxyl, or carboxyl present in the form of a salt, for example an alkali metal salt, such as a sodium salt, as well as protected carboxyl, for example esterified carboxyl, such as phenyl-lower alkoxycarbonyl, for example diphenylmethoxycarbonyl, sulpho, or sulpho present in the form of a salt, for example an alkali metal salt, such as a sodium salt, as well as protected sulpho, hydroxyl, as well as protected hydroxyl, such as acyloxy, for example α-polybranched lower alkoxycarbonyloxy, such as tert.-butoxycarbonyloxy or 2-halogeno-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkylphosphono or O,O'-di-lower alkylphosphono, for example O-methyl-phosphono or O,O'-dimethylphosphono, or denotes a 5-amino-5-carboxyvaleryl radical, wherein the amino and/or carboxyl groups can also be protected and are, for example, present a acylamino, for example lower alkanoylamino, such as acetylamino, halogeno-lower alkanoylamino such as dichloroacetylamino, benzoylamino or phthaloylamino, or as esterified carboxyl, such as phenyl-lower alkoxycarbonyl, for example diphenylmethoxycarbonyl, with m preferably representing 1, if $R_a$ is phenyl, hydroxyphenyl, hydroxy-chlorophenyl or pyridyl and m representing 0 and $R_b$ being different from hydrogen, if $R_a$ is phenyl, hydroxy-phenyl, hydroxy-chlorophenyl, thienyl, furyl or isothiazolyl, whereby $R_a$ can also be 1,4-cyclohexadienyl, if m represents O and $R_b$ is carboxyl, or carboxyl present in the form of a salt, for example an alkali metal salt, such as sodium salt, as well as protected carboxyl, for example esterified carboxyl, such as phenyl-lower alkoxycarbonyl, for example diphenylmethoxycarbonyl, sulpho, or sulpho present in the form of a salt, for example an alkali metal salt, such as a sodium salt, as well as protected sulpho, hydroxyl, as well as protected hydroxyl, such as acyloxy, for example α-polybranched lower alkoxycarbonyloxy, such as tert.-butoxycarbonyloxy or 2-halogeno-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkyphosphono or O,O'-di-lower alkylphosphono, for example O-methyl-phosphono or O,O'-dimethylphosphono, $R_1{}^b$ denotes hydrogen and $R_2{}^A$ represents lower alkoxy, especially α-poly-branched lower alkoxy, for example tert.-butoxy, 2-halogeno-lower alkoxy, for example 2,2,2-tichloroethoxy, 2-iodoethoxy or 2-bromoethoxy, or diphenylmethoxy which is optionally substituted, for example, by lower alkoxy, for example methoxy, for example diphenylmethoxy or 4,4'-dimethoxydiphenylmethoxy, as well as tri-lower alkylsilyloxy, for example trimethylsilyloxy, as well as the 1-oxides of such cepham-3-one compounds of the formula I, or salts of such compounds having salt-forming groups, such as acid addition salts, for example with mineral acids or strong carboxylic acids or sulphonic acids such as preferably halogen-substituted lower alkanecarboxylic acids or arylsulphonic acids, especially trifluoroacetic acid or 4-methylphenylsulphonic acid, of compounds of the formula I wherein $R_1{}^a$ and $R_1{}^b$ represent hydrogen.

Above all, in cephem-3-one compounds of the formula I as well as in salts of such compounds which have salt-forming groups, such as in the salts mentioned in the preceding paragraph, $R_1{}^a$ represents hydrogen, the acyl radical of the formula B, wherein R denotes phenyl, as well as hydroxyphenyl, for example 4-hydroxy-phenyl, thienyl, for example 2-thienyl or 3-thienyl or 4-isothiazolyl, X denotes oxygen, m denots 0 or 1 and $R_b$ denotes hydrogen, or, if m represents 0, denotes amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino, or hydroxyl, as well as protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or represents a 5-amino-5-carboxy-valeryl radical, wherein the amino and carboxyl group can also be protected and, for example, are in the form of acylamino, for example lower alkanoylamino, such as acetylamino, halogeno-lower alkanoylamino, such as dichloroacetylamino, benzoylamino or phthaloylamino, or of esterified carboxyl, such as phenyl-lower alkoxycarbonyl, for example diphenylmethoxycarbonyl, with m preferably representing 1, if $R_a$ denotes phenyl or hydroxyphenyl, whereby $R_a$ can also be 1,4-cyclohexadienyl, if m represents 0 and $R_b$ is hydroxyl, as well as protected hydroxyl, such as tert.-butoxycarbonyloxy, or 2-halogeno-lower alkoxycarbonyloxy, such as 2,2,2-trichloroethoxycarbonyloxy, and also formyloxy, $R_1{}^b$ represents hydrogen and $R_2{}^A$ is lower alkoxy which is optionally halogen-substituted, for example chlorine-substituted, bromine-substituted or iodine-substituted, in the 2-position, especially α-poly-branched lower alkoxy, for example tert.-butoxy, or 2-halogeno-lower alkoxy, for example 2,2,2-trichloroethoxy, 2-iodoethoxy or 2-bromoethoxy, or optionally lower alkoxy-substituted, such as methoxy-substituted, diphenylmethoxy, for example diphenylmethoxy or 4,4'-dimethoxy-diphenylmethoxy, and also tri-lower alkylsilyloxy, for example trimethylsilyloxy.

The invention above all relates to 7β-(D-α-amino-α-$R_a$-acetylamino)-cepham-3-one-4ξ-carboxylic acid diphenylmethyl esters, wherein $R_a$ represents phenyl, 4-hydroxyphenyl, or 2-thienyl and amino is preferably present in the protected form, for example as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyoxycarbonylamino, as well as 7β-amino-cepham-3-one-4ξ-carboxylic acid diphenylmethyl ester and salts thereof and above all 7β-(D-α-tert.butoxycarbonylamino-α-phenyl-acetylamino)-cepham-3-one-4ξ-carboxlic acid diphenylmethyl ester.

The compounds of the formula I are obtained if, in a cepham compound of the formula

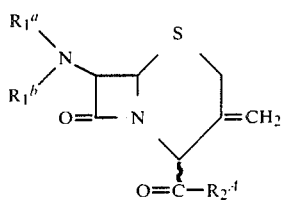
(II)

or in a 1-oxide thereof, the methylene group in the 3-positiion is split off oxidatively and, if desired, a resulting mixture of a compound of the formula I and of the corresponding 1-oxide is separated or oxidised to the 1-oxide of a compound of the formula I and/or, if desired, a resulting compound of the formula I is oxidised to the 1-oxide of a compound of the formula I and/or, if desired, a resulting compound is converted into a ketal and this is subsequently split if desired, and/or, if desired, a resulting compound of the formula I is converted into another compound of the formula I and/or, if desired, a resulting compound having a salt-forming group is converted into a salt or a resulting salt is converted into the free compound or into another salt and/or, if desired, a resulting isomer mixture is separated into the individual isomers.

In a starting material of the formula II, the protected carboxyl group of the formula —C(=O)—R$_2^A$ in the 4-position preferably has the α-configuration.

In a starting material of the formula II, an amino protective group R$_1^A$ in particular represents an acyl group Ac, wherein optionally present free functional groups, for example amino, hydroxyl, carboxyl or phosphono groups, can be protected in a manner which is in itself known, amino groups, for example, by acylation, tritylation, silylation or stannylation and hydroxyl, carboxyl or phosphono groups, for example, by etherification or esterification, including silylation or stannylation, and R$_1^b$ represents hydrogen, whilst R$_2^A$ preferably denotes an etherified hydroxyl group R$_2^A$ which forms, with the —C(=O)— grouping, an esterified carboxyl group which can be split, especially an esterified carboxyl group which can be split under mild conditions, it being possible for optionally present functional groups in a carboxyl protective group R$_2^A$ to be protected in a manner which is in itself known, for example as indicated above. A group R$_2^A$ is, for example, in particular an optionally substituted 1-phenyl-lower alkoxy group, such as a 1-phenyl-lower alkoxy group which contains lower alkoxy, for example methoxy, or nitro, such as benzyloxy or diphenylmethoxy which is optionally substituted, for example as indicated, for example benzyl, 4-methoxybenzyl, 4-nitrobenzyl, diphenylmethoxy or 4,4'-dimethoxy-diphenylmethoxy, as well as an optionally halogen-substituted lower alkoxy group, such as α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromoethoxy or 2-iodoethoxy, and also an organic silyloxy or stannyloxy group such as tri-lower alkylsilyloxy, for example trimethylsilyloxy.

The oxidative splitting off of the methylene group to form an oxo group in the 3-position of the ring skeleton can be effected in various ways.

Thus, it is possible to use oxidising agents which lead directly to the formation of compounds of the formula I. These are, in particular, oxidising agents which contain hexavalent chromium, such as dichromates, for example alkali metal dichromates, such as potassium dichromate, which are usually employed in the presence of aqueous organic solvents, such as suitable water-miscible ethers, for example dioxane, or ketones, for example acetone, and of a suitable acid, such as a mineral acid, for example sulphuric acid, or chromium trioxide which is usually employed in the presence of acetic acid and, if necessary, of an optionally aqueous organic solvent. The oxidation is carried out with cooling, for example down to about −90° C., at room temperature or with at most slight warming, for example up to about 40° C.

It is also possible, for example, to use oxidising agents which lead to the formation of glycol compounds which arise as intermediate products and which are converted into compounds of the formula I in an additional oxidation step. Such oxidising agents preferably contain heptavalent manganese or octavalent osmium or ruthenium, such as appropriate salts or oxides, above all, for example, permanganate compounds, such as alkali metal permanganates, for example potassium permanganate, or oxidizing heavy metal oxides, for example osmium tetraoxide or ruthenium tetraoxide. These oxidising agents are preferably used in the presence of solvents, such as suitable ethers, for example dioxane, ketones, for example acetone, optionally halogenated aliphatic, cycloaliphatic or aromatic hydrocarbons, for example carbon tetrachloride or benzene, or solvent mixtures, including aqueous mixtures, and are used with cooling or slight warming, for example at temperatures of about −90° to about +40° C.

The methylene group in a starting material of the formula II can also be converted into an O,O'-diester of an appropriate glycol grouping, for example with an organic carboxylic acid, such as an aliphtic carboxylic acid, for example an optionally halogen-substituted lower alkanecarboxylic acid, such as trifluoroacetic acid, and the diester grouping can be converted into the glycol grouping which can then be degraded to the keto group in an additional oxidation step. A suitable oxidising agent is an iodine-tris-halogeno-lower alkanoate, especially iodine-tristrifluoroacetate, which is usually employed in an inert solvent, such as an optionally halogenated hydrocarbon, for example methylene chloride, and optionally with cooling, but usually at room temperature. The diester of the glycol compound which can thus be obtained, and wherein the hydroxyl groups are esterified by halogen-lower alkanoyl radicals, especially trifluoroacetyl radicals, can be converted hydrolyically into the corresponding glycol compound, the reaction preferably being carried out under weakly basic conditions, for example in the presence of an alkali metal bicarbonate, for example sodium bicarbonate or potassium bicarbonate, or of a suitable phosphate buffer.

It is furthermore possible, in a starting material of the formula II, to oxidise the methylene group to the corresponding epoxy group by treatment with hydrogen peroxide, preferably in the presence of a suitable acid, such as formic acid, or in combination with other oxidising agents, such as heavy metal oxides, for example osmium tetraoxide or with an inorganic or organic peracid, especially a percarboxylic acid, such as peracetic acid, trifluoroperacetic acid, perbenzoic acid, 3-chloroperbenzoic acid or monoperphthalic acid, and to convert the epoxy group into the glycol grouping by treatment with a mild base, such as a metal alcoholate, such as an alkali metal lower alkanoate, for example sodium methanolate, ethanolate or tert.-butanolate or potassium methanolate, ethanolate or tert.-butanolate, in the presence of an alcohol, such as a lower alkanol, for example methanol, ethanol or tert.-butanol.

The glycol compounds obtainable as intermediate products are usually not isolated and are directly converted into the desired 3-oxo-cepham compound of the formula I by further oxidation, preferably by treatment with a periodate compound, such as an alkali metal periodate, for example sodium priodate, or an oxidising heavy metal acylate, such as a lead-IV acylate, for example lead tetraacetate or lead tetrabenzoate, thallium-III acylate, for example thallium triacetate, or mercury-II acylate, for example mercury diacetate, preferably in a suitable solvent or solvent mixture, such as one of those mentioned above, and with cooling or slight warming, for example at temperatures of about $-70°$ C. to about $+40°$ C.

The oxidative degradation of the methylene group in a starting material of the formula II is preferably carried out through the formation of an ozonide compound by treatment with ozone. Ozone is preferably used in the presence of a solvent, such as an alcohol, for example a lower alkanol, such as methanol or ethanol, a ketone, for example a lower alkananone, such as acetone, an optionally halogenated aliphatic, cycloaliphatic or aromatic hydrocarbon, for example a halogeno-lower alkane, such as methylene chloride or carbon tetrachloride, or a solvent mixture, including an aqueous mixture, and with at most slight warming, but preferably with cooling, that is to say at temperatures of about $-90°$ C. to about $+40°$ C., preferably at temperatures of about $-70°$ C. to about $+10°$ C., the reaction advantageously being carried out in a temperature range of about $-10°$ C. to about $+10°$ C. or in a substantially lower temperature range of about $-70°$ C. to about $-40°$ C.

An ozonide formed as the intermediate product is split by reduction, reducing agents used being, for example, catalytically activated hydrogen, such as hydrogen in the presence of a heavy metal hydrogenation catalyst, for example a nickel catalyst or a palladium catalyst, preferably on a suitable carrier, such as calcium carbonate or charcoal, or chemical reducing agents, such as reducing heavy metals, including heavy metal alloys or heavy metal amalgams, for example zinc, in the presence of a hydrogen donor, such as an acid, for example acetic acid, or an alcohol, for example a lower alkanol, reducing inorganic salts, such as alkali metal iodides, for example sodium iodide, in the presence of a hydrogen donor, such as an acid, for example acetic acid, or reducing organic compounds, such as formic acid. Advantageously, reducing agents which can easily be converted into oxide compounds are employed, in which the oxide formation can take place because of a carbon-carbon double bond which is present or because of an oxide-forming hetero-atom, such as sulphur, phosphorus or nitrogen atom, which is present. Such compounds are, for example, suitably substituted ethene compounds (which are converted into ethyleneoxy compounds during the reaction), such as tetracyanoethylene, and in particular suitable sulphide compounds (which are converted into sulphoxide compounds in the reaction), such as di-lower alkylsulphides, above all dimethylsulphide, suitable organic phosphorus compounds, such as a phosphine which can contain optionally substituted aliphatic or aromatic hydrocarbon radicals as substituents (and which is converted, during the reaction, into a phosphine oxide), such as tri-lower alkylphosphines, for example tri-n-butylphosphine, or triarylphosphines, for example triphenylphosphine and also phosphites which contain optionally substituted aliphatic hydrocarbon radicals as substituents (and which are converted into phosphoric acid triesters during the reaction), such as tri-lower alkylphosphites, usually in the form of the corresponding alcohol adduct compounds, such as trimethylphosphite, or phosphorous acid triamides, which contain optionally substituted aliphatic hydrocarbon radicals as substituents, such as hexalower alkylphosphorous acid triamides, for example hexamethylphosphorous acid triamide, the latter preferably in the form of a methanol adduct, and also suitable nitrogen bases (which are converted into the corresponding N-oxides during the reaction), such as heterocyclic nitrogen bases of aromatic character, for example bases of the pyridine type and especially pyridine itself. The splitting of the ozonide which is usually not isolated, is normally carried out under the conditions which are employed for its manufacture, that is to say in the presence of a suitable solvent or solvent mixture, and with cooling or slight warming, the reaction preferably being carried out at temperatures of about $-10°$ C. to about $+25°$ C. and usually being concluded at room temperature.

The invention particularly relates to a process for the manufacture of a 7β-amino-cephem-3-one-4-carboxylic acid compound of the formula

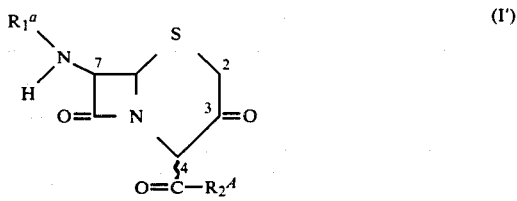

(I')

or of the 3-hydroxy-3-cephem form thereof wherein $R_1{}^a$ represents hydrogen or a group of the formula

(A₁)

wherein $R^I$ represents hydrogen or cycloalkyl with 5—7 ring carbon atoms which is substituted in the 1-position by amino, protected amino, such as lower alkoxycarbonylamino, 2-halogeno-lower alkoxycarbonylamino, phenyl-lower alkoxycarbonylamino, or by substituted amino, such as sulphoamino, or sulphoamino in the salt-form, or $R^I$ represents phenyl, naphthyl or tetrahydronaphthyl, or phenyl, naphthyl or tetrahydronaphthyl substituted by hydroxyl, lower alkoxy, protected hydroxyl, such as lower alkoxycarbonyloxy, 2-halogeno-lower alkoxycarbonyloxy or phenyl-lower alkoxycarbonyloxy, and/or by halogen, or $R^I$ represents an unsubstituted heterocyclic group or an heterocyclic group substituted by lower alkyl, and/or phenyl, which can in turn carry halogen, or $R^I$ represents an amino group which is N-substituted by lower alkyl or halogen-substituted lower alkyl or $R_1{}^a$ represents a group of the formula

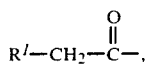 (A₂)

wherein $R^I$ represents lower alkyl, halogeno-lower alkyl, phenyloxy-lower alkyl, hydroxyphenyloxy-lower alkyl, hydroxyphenyloxy-lower alkyl, wherein hydroxy is protected, for example by lower alkoxycarbonyl or 2-halogeno-lower alkoxycarbonyl, halogenophenyloxy-lower alkyl, or $R^I$ represents lower alkyl substituted by amino and/or carboxyl, wherein amino is free or protected, for example by lower alkoxycarbonyl, halogeno-lower alkoxycarbonyl or benzoyl and carboxyl is free or protected, for example by lower alkyl, 2-halogeno lower alkyl, diphenylmethyl or phenyl-lower alkyl, or $R^I$ represents phenyl, hydroxyphenyl, protected hydroxyphenyl, such as lower alkoxycarbonyloxyphenyl or 2-halogeno-lower alkoxycarbonyloxyphenyl, halogen-phenyl, hydroxy-halogeno-phenyl, protected hydroxyhalogeno-phenyl, such as lower alkoxycarbonyloxy-halogenophenyl or 2-halogeno-lower alkoxycarbonyloxy-halogeno-phenyl, amino-lower alkylphenyl, protected amino-lower alkylphenyl, such as lower alkoxycarbonylamino-lower alkyl-phenyl or 2-halogeno-lower alkoxycarbonylamino-lower alkyl-phenyl, phenyloxyphenyl, pyridyl, pyridinium, thienyl, furyl, imidazolyl or tetrazolyl, or these heterocyclic groups substituted by lower alkyl, amino, protected amino, such as lower alkoxycarbonylamino or 2-halogeno-lower alkoxycarbonylamino, aminomethyl, protected aminomethyl, such as lower alkoxycarbonylaminomethyl or 2-halogeno-lower alkoxycarbonylminomethyl, or $R^I$ represents lower alkoxy, phenyloxy, hydroxyphenyloxy, protected hydroxyphenyloxy, such as lower alkoxycarbonyloxyphenyloxy or 2-halogeno-lower alkoxycarbonyloxy-phenyloxy, halogeno-phenyloxy, lower alkylthio, phenylthio, pyridylthio, 2-imidazolylthio, 1,2,4-triazol-3-ylthio, 1,3,4-triazol-2-ylthio, 1,2,4-thiadiazol-3-ylthio, 1,3,4-thiadiazol-2-ylthio, or 5-tetrazolylthio, and these heterocyclylthio groups substituted by lower alkyl, or $R^I$ represents halogeno, lower alkoxycarbonyl, cyano, carbamoyl, N-lower alkyl-carbamoyl, N-phenylcarbamoyl, lower alkanoyl, benzoyl or azido, or $R_1^a$ represents a group of the formula

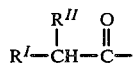 (A₃)

wherein $R^I$ represents lower alkyl, phenyl, hydroxyphenyl, protected hydroxyphenyl, such as lower alkoxycarbonyloxyphenyl or 2-halogeno-lower alkoxycarbonyloxy-phenyl, halogenophenyl, hydroxy-halogeno-phenyl, protected hydroxy-halogeno-phenyl, such as lower alkoxy-carbonyloxy-halogeno-phenyl or 2-halogeno-lower alkoxycarbonyloxy-halogeno-phenyl, furyl, thienyl or isothiazolyl, and $R^{II}$ represents amino or protected amino, such as lower alkoxycarbonylamino, 2-halogeno-lower alkoxycarbonylamino, mono- or diphenyl-lower alkoxycarbonylamino, lower alkoxyphenyl-lower alkoxycarbonylamino, nitrophenyl-lower alkoxycarbonylamino, arylsulphonylamino, tritylamino, arylthioamino, tritylamino, 2-propylideneamino which is substituted in 1-position by lower alkoxycarbonyl or lower alkanoyl, or $R^{III}$ represents substituted amino, such as guanidinocarbonylamino, sulphoamino or sulphoamino in salt-form, azido, carboxyl, carboxyl in salt-form, protected carboxyl, such as lower alkoxycarbonyl or diphenylmethoxycarbonyl, cyano, sulpho, hydroxyl, protected hydroxyl, such as formyloxy, lower alkoxycarbonyloxy, 2-halogeno-lower alkoxycarbonyloxy, mono- or diphenyl-lower alkoxycarbonyloxy, methoxy-phenyl-lower alkoxycarbonyloxy or nitrophenyl-loweralkoxycarbonyloxy, O-lower alkyl-phosphono, O,O'-di-lower alkyl-phosphono or halogeno, or $R_1^1$ represents a group of the formula

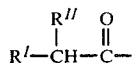 (A₄)

wherein $R^I$ and $R^{II}$ each represents halogeno, or lower alkoxycarbonyl, or $R_1^1$ represents a group of the formula

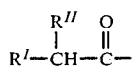 (A₅)

wherein $R^I$ represents phenyl, hydroxyphenyl, protected hydroxy-phenyl, such as lower alkoxycarbonyloxyphenyl or 2-halogeno-lower alkoxycarbonyloxyphenyl, halogen-phenyl, hydroxy-halogenophenyl, protected hydroxy-halogeno-phenyl, such as lower alkoxycarbonyloxy-halogeno-phenyl or 2-halogeno-lower alkoxycarbonyloxy-halogeno-phenyl, furyl, thienyl or isothiazolyl, and $R^{II}$ represents aminomethyl, protected aminomethyl, such as lower alkoxycarbonylaminomethyl or 2-halogen-lower alkoxycarbonylaminomethyl, or $R_1^a$ represents a group of the formula

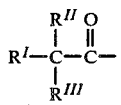 (A₆)

wherein each of the groups $R^I$, $R^{II}$ and $R^{III}$ represents lower alkyl, and $R_2^A$ represents a radical which together with the carbonyl grouping —C(=O)— forms a protected carboxyl group, and is for example lower alkoxy, halogeno-lower alkoxy, phenyl-lower alkoxy, niederalkoxyphenyl-lower alkoxy, nitrophenyl-lower alkoxy, diphenylmethoxy, di-(lower alkoxyphenyl)-methoxy, trityloxy or tri-lower alkylsilyloxy, 1-oxides and salts of such compounds of the formula I, characterised in that a cephem compound of the formula

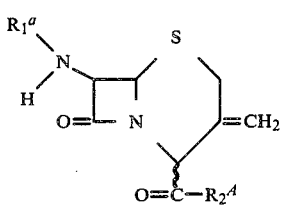 (II')

wherein $R_1^a$ has the meaning given under Formula I', a 1-oxide or a salt thereof, is treated with ozone and the resulting ozonide is split by reduction, as described above.

The new compounds of the formula I can also be manufactured by treating a cephem compound of the formula

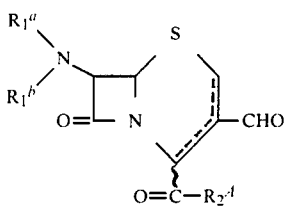
(III)

which contains a double bond in the 2,3- or 3,4-position, or a 1-oxide of a 3-cephem compound of the formula III, with a per-acid, and in a resulting 3formyloxy-4-$R_2^A$-carbonyl-7-N-$R_1^a$-N-$R_1^b$-amino-cephem compound or a 1-oxide thereof splitting the formyloxy group, and, if desired, carrying out the abovementioned additional steps.

The above reaction is carried out according to the Baeyer-Villiger oxidation method. This oxidation reaction uses inorganic per-acids which consist of non-metallic elements, organic per-acids or mixtures of hydrogen peroxide and acids, especially organic carboxylic acids having a dissociation constant of at least $10^{-5}$. Suitable inorganic per-acids are periodic and per-sulphuric acid. Organic per-acids are appropriate percarboxylic acids and persulphonic acids which can be added as such or can be formed in situ by the use of at least one equivalent of hydrogen peroxide and of a carboxylic acid. It is advisable to use a large excess of the carboxylic acid if, for example, acetic acid is used as the solvent. Examples of suitable per-acids are performic acid, peracetic acid, trifluoroperacetic acid, permaleic acid, perbenzoic acid, 3-chloroperbenzoic acid, monoperphthalic acid or p-toluenepersulphonic acid. The reaction is preferably carried out in the presence of an inert solvent, such as an optionally halogenated hydrocarbon, for example methylene chloride or chloroform, and preferably with cooling, for example at temperatures of about $-10°$ C. to about $+20°$ C.

In a resulting 3-formyloxy-4-$R_2^A$-carbonyl-7-N-$R_1^a$-N-$R_1^b$-amino-cephem compound, the formyloxy group can be split by solvolysis, especially hydrolysis, preferably in the presence of a basic agent, such as an alkali metal bicarbonate, for example sodium bicarbonate or potassium bicarbonate.

Depending on the nature of the above oxidation reactions, a compound of the formula I or the corresponding 1-oxide or a mixture of both compounds is obtained according to the invention. Such a mixture can be separated into the compound of the formula I and the corresponding 1-oxide, or can be oxidised to give only the 1-oxide of a compound of the formula I.

A mixture of a compound of the formula I with the corresponding 1-oxide can be separated into the individual components in the usual manner, for example by fractional crystallisation or by chromatography (for example column chromatography or thin layer chromatography).

Furthermore, a mixture, obtainable according to the process, of a compound of the formula I and a 1-oxide thereof, or a resulting compound of the formula I, can be oxidised to the corresponding 1-oxide. Suitable oxidising agents are inorganic per-acids which have a reduction potential of at least $+1.5$ volts and which consist of non-metallic elements, organic per-acids or mixtures of hydrogen peroxide and acids, especially organic carboxylic acids, having a dissociation constant of at least $10^{-5}$. Suitable inorganic per-acids are periodic acid and persulphuric acid. Organic per-acids are appropriate percarboxylic acids and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, trifluoroperacetic acid, permaleic acid, perbenzoic acid, 3-chloroperbenzoic acid, monoperphthalic acid or p-toluenepersulphuric acid.

The oxidation can also be carried out using hydrogen peroxide and catalytic amounts of an acid having a dissociation constant of at least $10^{-5}$, it being possible to employ low concentrations, for example 1–2% or less, but also larger amounts, of the acid. The activity of the mixture above all depends on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{31\ 5}$, its activity depending on its strength. Acids suitable as catalysts are, for example, acetic acid, perchloric acid and trifluoroacetic acid. Usually, at least equimolar amounts of the oxidising agent, and preferably a small excess of about 10% to about 20% are used, it also being possible to use larger excesses, that is to say up to the 10-fold amount of the oxidising agent, or above. The oxidation is carried out under mild conditions, for example at temperatures of about $-50°$ C. to about $+100°$ C., preferably of about $-10°$ C. to about $+40°$ C.

The oxidation of cephem-3-one compounds to the corresponding 1-oxides can also be carried out by treatment with ozone, as well as with organic hypohalite compounds, such as lower alkyl hypochlorites, for example tert.-butylhypochlorite, which are used in the presence of inert solvents, such as optionally halognated hydrocarbons, for example methylene chloride, and at temperatures of about $-10°$ C. to about $+30°$ C., with periodic compounds, such as alkali metal periodates, for example potassium periodate, which are preferably used in an aqueous medium at a pH value of about 6 and at temperatures of about $-10°$ C. to about $+30°$ C., with iodobenzene dichloride, which is used in an aqueous medium, preferably in the presence of an organic base, for example pyridine, and with cooling, for example at temperatures of about $-20°$ C. to about $0°$, or with any other oxidising agent which is suitable for conversion of a thio grouping into a sulphoxide grouping.

Depending on the oxidising agent used, the $1\alpha$-oxide or the $1\beta$-oxide or a mixture of both is obtained.

Ketal derivatives of compounds of the formula I can be manufactured in a manner which is in itself known, for example by treatment with a glycol, thioglycol or dithiioglycol in the presence of an acid catalyst, such as p-toluene-sulphonic acid, of a Lewis acid, such as zinc-II chloride, (especially when using thioglycol, where an agent which adsorbs water, such as sodium sulphate, is usually employed) or of an acid ion exchanger, usually in the presence of an inert solvent, such as an optionally halogenated, such as chlorinated, preferably aliphatic hydrocarbon, or of a suitable, optionally cyclic, ether, for example dioxane, or by ketal exchange, for example by treatment with a ketal of a lower alkanone, for example 2,2-ethylenedioxybutane, in the presence of a strong acid, such as p-toluenesulphonic acid, or with a ketal of a disubstituted formylamino compound, such as a N-formyl-N,N-di-lower alkylamine, for example (1,3-dioxolan-2-yl)-N,N-dimethylamine, in the presence of an acid, for example acetic acid.

Ketal compounds of compounds of the formula I can be split subsequently in a manner which is in itself known, ketals and thioketals, for example, by means of acid hydrolysis, such as with an aqueous inorganic or organic acid, for example hydrochloric acid, formic acid or trifluoroacetic acid, usually in the presence of an inert solvent, such as an optionally halogenated, such as chlorinated, preferably aliphaic hydrocarbon, or of a suitable, optionally cyclic, ether, and dithioketals, for example, by treatment with mercury-II chloride (usually in the presence of an aqueous solvent, for example acetone or dioxane) or with a N-halogenoamide or N-halogenoimide, such as N-bromosuccinimide.

Compounds of the formula I obtainable according to the invention can be converted into other compounds of the formula I, it being necessary to ensure that reaction conditions are chosen under which the oxo group in the 3-position, and the protective carboxyl group of the formula —C(=O)—R$_2^A$, remain intact, it also being possible for the oxo group to be present in a protected form, for example in the form of a functionally modified enol group, such as a silylated or stannylated enol group, or of a ketal group. It is furthermore possible, where necessary, for free functional groups which do not participate in the reaction to be protected in a manner which is in itself known, free amino groups, for example, by acylation, tritylation or silylation, free hydroxyl or mercapto groups, for example, by etherification or esterification, and free carboxyl groups, for example, by esterification, including silylation, and subsequently to be liberated, if desired, in a manner which is in itself known.

In a resulting compound it is possible, for example, to split off an amino protective group $R_1^A$ or $R_1^b$, especially an easily removable acyl group, in a manner which is in itself known, for example an α-polybranched lower alkoxycarbonyl group, such as tert.-butyloxycarbonyl, by treatment with trifluoroacetic acid, and a 2-halogeno-lower alkoxycarbonyl group, such as 2,2,2-trichloroethoxycarbonyl or 2-iodoethoxycarbonyl or a phenacyloxycarbonyl group, by treatment with a suitable reducing metal or corresponding metal compound, for example zinc, or a chromium-II compound, such as chromium-II chloride or chromium-II acetate, advantageously in the presence of an agent which together with the metal or the metal compound generates nascent hydrogen, preferably in the presence of aqueous acetic acid.

It is furthermore possible, in a resulting compound of the formula I, to split off an acyl group $R_1^A$ or $R_1^b$ wherein optionally present free fuctional groups are optionally protected, amino groups, for example, in the form of acylamino groups or silylated amino groups and/or carboxyl groups, for example, in the form of esterified or silylated carboxyl groups, by treatment with an imide-halide-forming agent, reaction of the resulting imide-halide with an alcohol and splitting of the iminoether formed.

Imide-halide-forming agents in which halogen is bonded to an electrophilic central atom are above all acid halides, such as acid bromides and especially acid chlorides. The acid halides are above all acid halides of inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyrocatechyl-phosphorus trichloride, as well as acid halides, especially acid chlorides, of acids containing sulphur or of carboxylic acids, such as thionyl chloride, phosgene or oxalyl chloride.

The reaction with one of the imide-halide-forming agents mentioned is usually carried out in the presence of a suitable base, especially of an organic base, above all of a tertiary amine, for example a tertiary aliphatic monoamine or diamine, such as a tri-lower alkylamine, for example trimethylamine, triethylamine or N-ethyl-N,N-diisopropylamine, also a N,N,N′,N′-tetra-lower alkyl-lower alkylenediamine, for example N,N,N′,N′-tetramethyl-1,5-pentylenediamine or N,N,N′,N′-tetramethyl-1,6-hexylenediamine, a monocylic or bicyclic monoamine or diamine, such as a N-substituted, for example N-lower alkylated, alkyleneamine, azaalkyleneamine or oxaalkyleneamine, for example N-methyl-piperidine or N-methyl-morpholine, as well as 2,3,4,6,7,8-hexahydro-pyrrolo[1,2-a]pyrimidine (diazabicyclonone; DBN), or a tertiary aromatic amine such as a di-lower alkylaniline, for example N,N-dimethylaniline, or above all a tertiary heterocyclic, monocyclic or bicyclic, base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; the latter can however also be present in more than or less than equimolar amount, for example in about 0.2-fold to about 1-fold amount or in, up to about 10-fold, in particular about 3-fold to 5-fold, excess.

The reaction with the imide-halide-forming agent is preferably carried out with cooling, for example at temperatures of about −50° C. to about +10° C., but it is also possible to work at higher temperatures, that is to say, for example, up to about 75° C., if the stability of the starting substances and of the products permits a higher temperature.

The imide-halide product which is usually further processed without isolation, is reacted according to the process with an alcohol, preferably in the presence of one of the above-mentioned bases, to give the iminoether. Examples of suitable alcohols are aliphatic as well as araliphatic alcohols, above all optionally substituted, such as halogenated, for example chlorinated, lower alkanols or lower alkanols possessing additional hydroxyl groups, for example ethanol, propanol or butanol but especially methanol, also 2-halogeno-lower alkanols, for example 2,2,2-trichloroethanol or 2-bromoethanol, and optionally substituted phenyl-lower alkanols, such as benzyl alcohol. Usually an excess, for example up to about 100-fold excess, of the alcohol is employed and the reaction is preferably carried out with cooling, for example at temperatures of about −50° C. to about 10° C.

The imino-ether product can advantageously be split without isolation. The splitting of the imino-ether can be achieved by treatment with a suitable hydroxy compound, preferably by means of hydrolysis, and also by alcoholysis, and the latter can take place directly following the formation of the imino-ether, if an excess of the alcohol is used. Preferably, water or an alcohol, especially a lower alkanol, for example methanol, or an aqueous mixture of an organic solvent, such as an alcohol, is used. The reaction is usually carried out in an acid medium, for example, for example at a pH value of about 1 to about 5 which can, if necessary, be obtained by adding a basic agent, such as an aqueous alkali metal hydroxide, for example sodium hydroxide or potassium hydroxide, or an acid, for example a mineral acid, or an organic acid, such as hydrochloric acid, sulphuric acid, phosphoric acid, fluoroboric acid, trifluoroacetic acid or p-toluenesulphonic acid.

The three-stage process for splitting off an acyl group, described above, is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product obtainable according to the above process, instead of being reacted with an alcohol, is reacted with a salt, such as an alkali metal salt, of a carboxylic acid, especially of a sterically hindered carboxylic acid, a compound of the formula I, wherein both radicals $R_1^a$ and $R_1^b$ represent acyl groups, is obtained.

In a compound of the formula I, wherein both radicals $R_1^a$ and $R_1^b$ represent acyl groups, one of these groups, preferably the sterically hindered group, can be removed selectively, for example by hydrolysis or aminolysis.

Certain acyl radicals $R_1^a$ of an acylamino grouping in compounds obtainable according to the invention such as, for example, the 5-amino-5-carboxyl-valeryl radical, wherein carboxyl is optionally protected, for example by esterification, especially by diphenylmethyl, and/or the amino group is optionally protected, for example by acylation, especially by an acyl radical of an organic carboxylic acid, such as halogeno-lower alkanoyl, such as dichloroacetyl, or phthaloyl, can also be split off by treatment with a nitrosilyating agent, such as nitrosyl chloride, with a carbocyclic arenediazonium salt, such as benzenediazonium chloride, or with an agent which releases positive halogen, such as a N-halogeno-amide or -imide, for example N-bromosuccinimide, preferably in a suitable solvent or solvent mixture, such as formic acid, together with a nitro- or cyano-lower alkane, and treatment of the reaction product with a hydroxylic agent, such as water or a lower alkanol, for example methanol or, if in the 5-amino-5-carboxy-valeryl radical $R_1^A$ the amino group is unsubstituted and the carboxyl group is protected, for example by esterification and $R_1^b$ preferably represents an acyl radical but can also denote hydrogen, by leaving the substance to stand in an inert solvent, such as dioxane or a halogenated aliphatic hydrocarbon, for example methylene chloride and, if necessary, working up the free or monocylated amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group, such as the trityl group $R_1^A$, can be split off, for example, by treatment with an acid agent, such as mineral acid, for example hydrochloric acid.

In a compound of the formula I, wherein $R_1^a$ and $R_1^b$ represents hydrogen, and the oxo group in the 3-position is protected, if necessary, for example as described, the free amino group can be protected according to methods which are in themselves known, for example acylated by treatment with acids, such as carboxylic acids, or reactive acid derivatives thereof.

If a free acid wherein, preferably, optionally present functional groups, such as an optionally present amino group, are protected, is employed for the acylation, suitable condensation agents are usually employed, such as carbodiimides, for example N,N'-diethyl-, N,N'-dipropyl-, N,N'-diisopropyl-, N,N'-dicyclohexyl- or N-ethyl-N'-3-dimethylaminopropyl- carbodiimide, suitable carbonyl compounds, for example carbonyl diimidazole, or isoxazolinium salts, for example N-ethyl-5-phenyl-isoxazolium-3'-sulphonate and N-tert.-butyl-5-methylisoxazolium perchlorate, or a suitable acylamino compound, for example 2-ethoxy-1-ethoxycarbonyl-1,2-dihyroquinoline.

The condensation reaction is preferably carried out in one of the anhydrous reaction media mentioned later, for example in methylene chloride, dimethylformamide or acetonitrile.

An amide-forming functional derivative of an acid, wherein optionally present groups, such as an optionally present amino group, are preferably protected, is above all an anhydride of such an acid, including, and preferably, a mixed anhydride. Mixed anhydrides are, for example, those with inorganic acids, especially with hydrogen halide atoms, that is to say the corresponding acid halides, for example acid chlorides or acid bromides, and also with hydrazoic acid, that is to say the corresponding acid azides, with an acid containing phosphorus, for example phosphoric acid or phosphorus acid, with an acid containing sulphur, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with a half-esters, especially lower alkyl half-ester, of carbonic acid, such as the ethyl half-ester or isobutyl half-ester of carbonic acid, or with organic, especially aliphatic, or aromatic, sulphonic acids, for example p-toluenesulphonic acid.

It is furthermore possible to use, as acylating agents, internal anhydrides, such as ketenes, for example diketene, isocyanates, (that is to say internal anhydrides of carbamic acid compounds) or internal anhydrides of carboxylic acid compounds having carboxyl-substituted hydroxyl or amino groups, such as mandelic acid O-carboxanhydride or the anhydride of 1-N-carboxyaminocyclohexanecarboxylic acid.

Further acid derivatives suitable for reaction with the free amino group are activated esters, wherein the optionally present functional groups are usually protected, such as esters with vinylogous alcohols, (that is to say enols), such as vinylogous lower alkanols, or aryl esters, such as phenyl esters which are preferably substituted, for example, by nitro or halogen, such as chlorine, for example pentachlorophenyl, 4-nitrophenyl or 2,4-dinitrophenyl esters, hetero-aromatic esters, such as benztriazole esters, or diacylimino esters, such as succinylimino esters or phthalyimino esters.

Further acylation derivatives are, for example, substituted formimino derivatives, such as substituted N,N-dimethylchloroformimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a tertiary amine, such as tri-lower alkylamine, for example triethylamine, N,N-di-lower alkylaniline, for example N,N-dimethylaniline, or a base of the pyridine type, for example pyridine, an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or an oxirane, for example a lower 1,2-alkylene oxide, such as ethylene oxide or propylene oxide.

The above acylation can be carried out in an aqueous or, preferably, anhydrous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

An acyl group can also be introduced by acylating a compound of the formula I wherein $R_1^a$ and $R_1^b$ together represent an ylidene radical, (which can also be introduced subsequently, for example by treating a compound wherein $R_1^a$ and $R_1^b$ represent hydrogen, with an aldehyde, such as an aliphatic, aromatic or araliphatic aldehyde), for example according to the methods indicated above, and hydrolysing the acylation product preferably in a neutral or weakly acid medium.

An acyl group can also be introduced stepwise. Thus, for example, it is possible to introduce into a compound of the formula I, having a free amino group, a halogeno-lower alkanoyl group, for example a bromoacetyl group, or, for example by treatment with a carbonic acid dihalide, such as phosgene, a halogenocarbonyl group, for example a chlorocarbonyl group, and to react a N-(halogeno-lower alkanoyl)-amino compound or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol and thus to obtain substituted N-lower alkanoyl-amino or N-hydroxycarbonylamino compounds.

It is furthermore possible, for example, to react a compound of the formula I, wherein $R_1^a$ represents a glycyl group which is preferably substituted in the α-position, such as phenylglycyl, and $R_1^b$ represents hydrogen, with an aldehyde, for example formaldehyde, or a ketone, such as lower alkanone, for example acetone, and thus to arrive at compounds of the formula I, wherein $R_1^a$ and $R_1^b$ together with the nitrogen atom represent a 5-oxo-1,3-diaza-cyclopentyl radical which is preferably substituted in the 4-position and is optionally substituted in the 2-position.

The acylation can also be effected by replacement of an already existing acyl group by another, preferably sterically hindered, acyl group, for example according to the process described above, by manufacturing the imide-halide compound, treating this with a salt of an acid and splitting off hydrolytically one of the acyl groups present in the product thus obtainable, usually the sterically less hindered acyl group.

In a compound of the formula I, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkylsilane, lower alkoxy-lower alkyl-dihalogeno-silane or tri-lower alkyl-silyl halide, for example dichlorodimethylsilane, methoxy-methyldichloro-silane, trimethylsilyl chloride or dimethyl-tert.-butyl-silyl chloride, such silyl halide compounds preferably being used in the presence of a base, for example pyridine, or by treatment wth an optionally N-monolower alkylated, N,N-di-lower alkylated, N-tri-lower alkylsilylated or N-lower alkyl-N-tri-lower alkylsilylated N-(tri-lower alkylsilyl)-amine (see, for example, British Pat. No. 1,073,530), or with a silylated carboxylic acid amide, such as a bis-tri-lower alkylsilylacetamide, for example bistrimethylsilyl-acetamide or trifluorosilylacetamide, or by treatment with a suitable stannylating agent, such as a bis-(tri-lower alkyl-tin) oxide, for example bis-(tri-n-butyl-tin) oxide, a tri-lower alkyl-tin hydroxide, for example triethyltin hydroxide, a tri-lower alkyl-lower alkoxy-lower, alkoxy-tin compound, tetra-lower alkoxy-tin compound or tetra-lower alkyl-tin compound, or with a tri-lower alkyl-tin halide, for example tri-n-butyl-tin chloride (see, for example, Netherlands Published Specification No. 67/11,107).

In a resulting compound having an esterified grouping of the formula $-C(=O)-R_2^A$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

In the process according to the invention, and in additional measures which may require to be carried out it is possible, if necessary, transiently to protect free functional groups, which do not participate in the reaction, in the starting substances, or in the compounds obtainable according to the process, for example free amino groups by, for example, acylation, tritylation or silylation, free hydroxyl or mercapto groups by, for example, etherification or esterification, and free carboxyl groups by, for example, esterification, including silylation and in each case to liberate them after the reaction has taken place, if desired, individually or conjointly, in a manner which is in itself known. Thus it is preferably possible, for example, to protect amino, hydroxyl, carboxyl or phosphono groups in an acyl radical $R_1^A$ or $R_1^b$, for example in the form of acylamino groups, such as those mentioned above, for example 2,2,2-trichloroethoxycarbonylamino, 2-bromoethoxycarbonylamino, 4-methoxybenzyloxycarbonylamino, diphenylmethoxycarbonylamino or tert.-butoxycarbonylamino groups, of arylthioamino or aryl-lower alkylthioamino groups, for example 2-nitrophenylthioamino groups, or arylsulphonylamino groups, for example 4-methylphenylsulphonylamino groups, or of 1-lower alkoxycarbonyl-2-propylideneamino groups, or, respectively, of acyloxy groups, such as those mentioned above, for example tert.-butoxycarbonyloxy, 2,2,2-trichloroethoxycarbonyloxy or 2-bromoethoxycarbonyloxy groups, or, respectively, of esterified carboxyl groups, such as those mentioned above, for example diphenylmethoxycarbonyl groups, or, respectively, O,O'-disubstituted phosphono groups, such as those mentioned above, for example O,O'-di-lower alkylphosphono groups, for example O,O'-dimethylphosphono groups and subsequently, optionally after conversion of the protective group, for example of a 2-bromoethoxycarbonyl group into a 2-iodoethoxycarbonyl group, to split the protected group in a manner which is in itself known and depending on the nature of the protective group, for example a 2,2,2-trichloroethoxycarbonylamino or 2-iodoethoxycarbonylamino group by treatment with suitable reducing agents, such as zinc in the presence of aqueous acetic acid, a diphenylmethoxycarbonylamino or tert.-butoxycarbonylamino group by treatment with formic acid or trifluroacetic acid, an arylthioamino or aryl-lower alkylthioamino group by treatment with a nucleophilic reagent, such as sulphurous acid, an arylsulphonylamino group by means of electrolytic reduction, a 1-lower alkoxycarbonyl-2-propylideneamino group by treatment with an aqueous mineral acid, or a tert.-butoxycarbonyloxy group by treatment with formic acid or trifluoroacetic acid, or a 2,2,2-trichloroethoxycarbonyloxy group by treatment with a chemical reducing agent, such as zinc in the presence of aqueous acetic acid, or a diphenylmethoxycarbonyl group by treatment with formic acid or trifluoroacetic acid or by hydrogenolysis, or an O,O'-disubstituted phosphono group by treatment with an alkali metal halide, the splitting being carried out if desired, for example partially.

Salts of compounds of the formula I can be manufactured in a manner which is in itself known. Thus, salts of such compounds which possess acid groups can be formed, for example, by treatment with metal compounds, such as alkali metal salts, of suitable carboxylic acids, for example the sodium salt of α-ethyl-caproic acid, or with ammonia or a suitable organic amine, preferably using stoichiometric amounts or only a small excess of the salt-forming agent. Acid addition salts of compounds of the formulae I (sic) having basic groupings are obtained in the customary manner, for example by treatment with an acid or with a suitable anion exchange reagent. Internal salts of compounds of the formulae I (sic) which contain a salt-forming amino group and a free carboxyl group can be formed, for example, by neutralising salts, such as acid addition salts, to the isoelectric point, for example with weak bases, or by treatment with liquid ion exchangers. Salts of 1-oxides of compounds of the formula I having salt-forming groups can be manufactured analogously.

Salts can be converted into the free compounds in the customary manner, metal salts and ammonium salts, for example, by treatment with suitable acids, and acid addition salts, for example, by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation processes. Resulting racemates can be separated into the antipodes in the usual manner, if appropriate after introducing suitable salt-forming groupings, for example by forming a mixture of diastereomeric salts with optically active salt-forming agents, separating the mixture into the diasteromeric salts and converting the separated salts into the free compounds, or by fractional crystallisation from optically active solvents.

The process also encompasses those embodiments according to which compounds arising as intermediate products are used as starting substances and the remaining process steps are carried out with these, or the process is stopped at any stage; furthermore, starting substances can be used in the form of derivatives or be formed during the reaction.

Preferably, those starting substances are used, and the reaction conditions are so chosen, that the compounds initially mentioned as being particularly preferred are obtained.

The starting compounds of the formula II used according to the invention can be manufactured, for example, by converting the acetoxymethyl group in a cephem compound of the formula

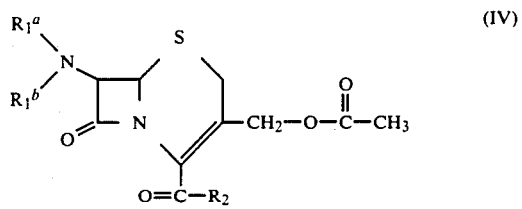

(IV)

wherein $R_1^a$ preferably represents an amino protective group $R_1^A$ and wherein $R_2$ preferably represents hydroxyl, but also represents a group $R_2^A$, into the hydroxymethyl group, for example by hydrolysis in a weakly basic medium, such as with an aqueous sodium hydroxide solution at pH 9–10, or by treatment with a suitable esterase, such as an appropriate enzyme from *Rhizobium tritolii, Rhizobium lupinii, Rhizobium japonicum* or *Bacillus subtilis*, functionally modifying a free carboxyl group of the formula —C(=O)—$R_2$ in a suitable manner, for example esterifying it by treatment with a diazo compound, such as diphenyldiazomethane, and converting the hydroxymethyl group into a halogenomethyl group, for example a chloromethyl or iodomethyl group, for example by treatment with a halogenating agent, such as a chlorinating agent, for example thionyl chloride, or an iodinating agent, for example N-methyl-N,N'-dicyclohexylcarbodiimidium iodide. A chloromethyl group is converted into the methylene group of the starting material of the formula II either directly, for example by treatment with a suitable chromium-II compound, such as an inorganic or organic salt of divalent chromium, for example chromium-II chloride or chromium-II acetate, in a suitable solvent, such as dimethylsulphoxide, or indirectly via the iodomethyl group (which can be formed, for example, by treating the chloromethyl compound with a metal iodide, such as sodium iodide, in a suitable solvent, such as acetone), by treatment of a resulting iodomethyl compound with a suitable reducing agent, such as zinc in the presence of acetic acid.

In a compound of the formula II which can also be obtained from compounds of the formula IV by electrochemical reduction or by reduction with chromium-II salts or aluminium amalgam, a protected amino group in the 7-position can be liberated or be converted into another protected amino group and/or a free amino group in the 7-position can be converted into a protected amino group; these reactions are carried out in a manner which is in itself known, for example as described above.

The starting substances of the formula III can be obtained, for example, if in an abovementioned compound of the formula

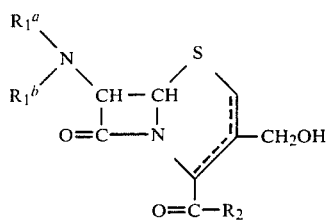 (V)

wherein $R_2$ preferably represents hydroxyl and which contains a double bond in the 2,3- or 3,4-position, the hydroxymethyl group is oxidised to the formyl group and, at a suitable stage, a 3-cephem compound is isomerised to the desired 2-cephem compound and, if desired or required, a hydroxyl group $R_2$ in a resulting compound is replaced by a suitable etherified hydroxyl group or by an amino or hydrazino group. The oxidation can be carried out, for example, according to the process described in U.S. Pat. No. 3,351,596, that is to say by treatment with oxidising metal compounds, such as metal oxides, for example chromium trioxide or manganese dioxide, or, in the case of 2-cephem compounds, advantageously with 2,3-dichloro-5,6-dicyano-1,4-benzoquinone and, in the case of 3-cephem compounds, advantageously with aliphatic sulphoxides, such as di-lower alkylsulphoxides, for example dimethylsulphoxide, or lower alkylenesulphoxides, for example tetramethylenesulphoxide, in the presence of aliphatic carboxylic acid anhydrides, for example acetic anhydride, preferably using an excess of the sulphoxide and an equimolar amount of the anhydride as compared to the sulphoxide, and at temperatures of about $-50°$ C. to about $+70°$ C., if desired in the presence of an additional inert solvent, such as benzene or toluene. The isomerisation of a 3-cephem compound to the corresponding 2-cephem compound can be effected, for example, by treating an ester or anhydride, which has optionally been formed in situ, with a base, such as a tertiary amine, for example triethylamine, and/or a heterocyclic base, for example pyridine.

The 2-cephem starting substances of the formula III can also be obtained by total synthesis, for example according to the method described in Austrian Pat. Nos. 263,768 and 264,537.

As mentioned above, the new compounds of the formula II can be used as intermediate products for the manufacture of compounds having the cepham structure, which either possess valuable pharmacological properties or can again be used as intermediate products.

Thus, for example, it is possible to convert the compounds of the formula II into their enol derivatives, for example into an enol ether by treatment with an optionally substituted diazo-hydrocarbon compound of aliphatic character, such as a diazo-lower alkane, for example diazomethane, or a phenyl-diazo-lower alkane, such as phenyl-diazomethane, or into an enol ester by treatment with an acid or, preferably, a suitable acid derivative, such as a halide, for example a chloride, or an anhydride, and, if desired, to convert a protected carboxyl group of the formula $-C(=O)-R_2^A$, in enol derivatives thus obtainable, into a free carboxyl group in a manner which is in itself known, and thus to arrive at cephem compounds of the formula

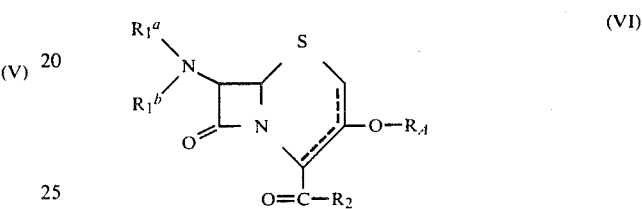 (VI)

which contain a double bond in the 2,3- or 3,4-position and wherein $R_1^a$ and $R_1^b$ have the abovementioned meanings, $R_2$ represents hydroxyl or a radical $R_2^A$ which, together with the carbonyl grouping, forms a protected carboxyl group, and $R_A$ denotes an optionally substituted hydrocarbon radical of aliphatic character or an acyl group. Compounds of the formula VI, especially those in which $R_1^a$ represents an acyl radical contained in pharmacologically active N-acyl derivatives of 6β-amino-penam-3-carboxylic acid compounds and 7β-amino-3-cephem-4-carboxylic acid compounds, $R_1^b$ denotes hydrogen and $R_2$ represents hydroxyl or an etherified hydroxyl group which together with the carbonyl grouping forms a carboxyl group which can be split under physiological conditions, and $R_A$ has the abovementioned meaning, with functional groups optionally present in an acyl radical $R_1^a$, such as amino, carboxyl, hydroxyl and/or sulpho, usually being present in the free form, or salts of such compounds having salt-forming groups, on parenteral and/or oral administration are active against micro-organisms, such as Gram-positive bacteria, for example *Staphylococcus aureus*, *Streptococcus pyogenes* and *Diplococcus pneumoniae*, (for example in mice at doses of about 0.001 to about 0.02 g/kg administered subcutaneously or orally), and Gram-negative bacteria, for example *Escherichia coli*, *Salmonella typhimurium*, *Shigella flexneri*, *Klebsiella pneumoniae*, *Enterobacter cloacae*, *Proteus vulgaris*, *Proteus rettgeri* and *Proteus mirabilis*, (for example in mice in doses of about 0.001 to about 0.15 g/kg administered subcutaneously or orally), and especially also against penicillin-resistant bacteria, whilst being of low toxicity. These new compounds can therefore be used, for example in the form of antibiotically active preparations, for the treatment of corresponding injections.

Furthermore, it is possible, in the cepham compounds of the formula I, to reduce the oxo group in the 3-position to the hydroxyl group, for example by treatment with a suitable complex metal hydride, such as sodium borohydride, in the presence of a suitable solvent, such as an alcohol or ether, and to convert the hydroxyl group, if desired, into an esterified hydroxyl group, especially into a hydroxyl group esterified by an organic carboxylic acid, and/or to convert a protected carboxyl group of the formula —C(=O)—$R_2^d$ into the free carboxyl group. In the cepham compound thus obtainable of the formula

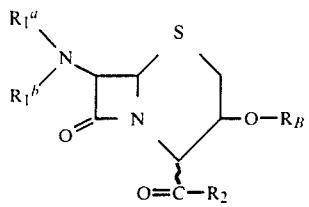

wherein $R_B$ represents hydrogen or an acyl radical, the elements of a compound of the formula $R_B$—OH VIII, that is to say of water of or an acid, can be split off under acid or basic conditions, and the known 3-cephem compounds of the formula

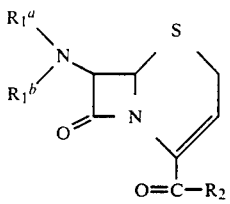

are thus obtained, wherein $R_1^a$, $R_1^b$ and $R_2$ have the above-mentioned meanings and in which these radicals can be converted into one another in a manner which is in itself known. The compounds of the formula IX or salts thereof however possess valuable pharmacological, especially antimicrobial properties, especially in those cases in which $R_1^a$ represents an acyl radical contained in pharmacologically active N-acyl derivatives of 6β-amino-penam-3-carboxylic acid compounds and 7β-amino-3-cephem-4-carboxylic acid compounds, $R_1^b$ denotes hydrogen and $R_2$ represents hydroxyl or an etherified hydroxyl group which together with the carbonyl grouping forms a carboxyl group which can be split under physiological conditions, or salts thereof, or can be used as intermediate products for the manufacture of the said compounds having pharmcological properties.

In the above conversions of compounds according to the invention, of the formula I, to the compounds of the formula IV or to the compounds of the formulae V and VII, it is not necessary to isolate compounds of the formula I; it is possible to convert them directly, in the form of the crude reaction mixtures after the manufacture from the compounds of the formula II, into the compounds of the formula VI or VII and IX.

In the context of the present description, organic radicals described as "lower" contain up to 7, preferably up to 4, carbon atoms; acyl radicals contain up to 20, preferably up tp 12, carbon atoms.

The examples which follow serve to illustrate the invention.

EXAMPLE 1

A solution of 0.50 g of 3-methylene-7β-phenylacetylamino-cepham-4α-carboxylic acid diphenylmethyl ester in 100 ml of methanol is treated for 6.5 minutes at −70° C. with a stream of oxygen and ozone, containing 0.175 mmol/min. of ozone. The reaction mixture is treated with 0.5 ml of dimethylsulphide and is stirred for one hour at −70° C. and then for 2 hours at room temperature and evaporated to dryness. The residue, in methylene chloride, is chromatographed on 15 g of silica gel. Amorphous 7β-phenylacetylamino-cepham-3-one-4ξ-carboxylic acid diphenylmethyl ester is eluted with methylene chloride, thin layer chromatography (silica gel): Rf~0.47 (system: toluene/acetone/methanol/acetic acid, 80:10:5:5); infrared absorption spectrum (in methylene chloride): characteristic bands at 2.95μ, 5.61μ, 5.77μ, 5.85μ, 5.95μ, 6.21μ and 6.87μ; the compound shows a positive iron-III chloride reaction, which indicates the presence of the enol form.

Using methylene chloride, containing 10% of acetone, it is possible to elute a polar compound whichis very probably identical with 7β-phenylacetylamino-cepham-3-one-4ξ-carboxylic acid diphenylmethyl ester-1-oxide, thin layer chromatogram (silica gel): Rf=0.22 (system: toluene/acetone/methanol/acetic acid, 80:10:5:5); infrared absorption spectrum (in methylene chloride): characteristic bands at 2.96μ, 5.58μ, 5.76μ (shoulder), 5.83μ, 5.97μ, 6.22μ and 6.61μ; the compound shows a positive iron-III chloride reaction which indicates the presence of the enol form.

The starting material can be manufactured as follows:

A solution of 11.82 g of the crude sodium salt of 3-hydroxymethyl-7β-phenylacetylamino-3-cephem-4-carboxylic acid (manufactured by enzymatic desacetylation of the sodium salt of 3-acetoxymethyl-7β-phenylacetylamino-3-cephem-4-carboxylic acid with the aid of a purified enzyme extract from Bacillus subtilis, strain ATCC 6,633, and subsequent lyophilisation of the reaction solution) in 200 ml of water is covered with 400 ml of ethyl acetate and acidified to a pH value of 2 with concentrated aqueous phosphoric acid. The aqueous phase is separated off and twice re-extracted with 150 ml of ethyl acetate at a time. The combined organic extracts are washed four times with 50 ml of water at a time, dried over magnesium sulphate and then concentrated to about 400 ml. Excess diphenyldiazomethane is added to the solution, which is left to stand for 3 hours at room temperature, and the granular crystalline precipitate is then filtered off. The filtrated off. The filtrate is concentrated to about 200 ml, cyclohexane is added whilst warm and after cooling to room temperature the mixture is left to stand for some time at about 4° C. The precipitate is filtered off and recrystalised from a mixture of acetone and cyclohexane; the 3-hydroxymethyl-7β-phenylacetylamino-3-cephem-4-carboxylic acid diphenylmethyl ester thus obtained melts at 176°–176.5° C. (uncorrected); $[\alpha]_D^{20}=-6°\pm1°$ (c=1.231% in chloroform); thin layer chromatogram (silica gel; detection with iodine vapour or ultraviolet light, $\lambda_{254}$ $m_\mu$); Rf=0.42 (system: chloroform/acetone, 4:1), Rf=0.43 (system: toluene/acetone, 2:1), and Rf=0.41 (system: methylene chloride/acetone, 6:1).

1.03 g of 3-hydroxymethyl-7β-phenylacetylamino-3-cephem-4-carboxylic acid diphenylmethyl ester and 1.05 g of N-methyl-N,N'-dicyclohexylcarbodiimidium iodide are dissolved in 25 ml of absolute tetrahydrofurane under a nitrogen atmosphere and warmed at 35° C. for one hour. Thereafter, a further 1.05 g of N-methyl-N,N'-dicyclohexylcarbodiimidium iodide, in 15 ml of absolute tetrahydrofurane, is added and the mixture is left to stand for 17 hours at room temperature under a nitrogen atmosphere. The reaction mixture is freed of the solvent on a rotary evaporator under reduced pressure. The residue is taken up in methylene chloride and filtered through a column of 50 g of silica gel (with addition of 10% of distilled water); the column is rinsed with 4 portions of methylene chloride, each of 100 ml. The eluate is concentrated to a small volume and chromatographed on a silica gel column (90 g; deactivated by adding 10% of distilled water). Non-polar impurities are eluted with a total of 900 ml of a 3:7 mixture of toluene and methylene chloride. Elution with 2 portions of methylene chloride, each of 200 ml, yields 3-iodomethyl-7β-phenylacetylamino-3-cephem-4-carboxylic acid diphenylmethyl ester; the fractions which according to a thin layer chromatogram are a single substance are lyophilised from benzene. Infrared absorption spectrum (in methylene chloride): characteristic bands at $3.00\mu$, $5.62\mu$, $5.82\mu$, $5.95\mu$, $6.70\mu$, $7.32\mu$ and $8.16\mu$.

The iodination reagent used above can be manufactured as follows:

42 g of freshly distilled N,N'-dicyclohexylcarbodiimide are dissolved in 90 ml of methyl iodide in a 250 ml round flask equipped with a magnetic stirrer and reflux condenser and fitted nitrogen bulb, at room temperature under a nitrogen atmosphere, and the colourless reaction mixture is stirred for 72 hours at a bath temperature of 70° C. At the end of the reaction time, the excess methyl iodide is distilled from the solution, which is now red-brown, under reduced pressure and the viscous red-brown residue is dissolved in 150 ml of abslute toluene at 40° C. The crystal mass, which crystallises out spontaneously within a few hours, is separated from the mother liquor with the aid of a glass suction filter with fitted nitrogen bulb, whilst excluding air, the reaction vessel is rinsed three times with 25 ml of absolute, ice-cold toluene at a time and the same toluene is used in order to wash the slightly yellowish crystal mass on the glass suction filter until it is colourless. After drying for 20 hours at 0.1 mm Hg and room temperature, the N-methyl-N,N'-dicyclohexylcarbodiimidium iodide is obtained in the form of colourless crystals, melting point 111°-113° C.; infrared absorption spectrum (in chloroform): characteristic bands at $4.72\mu$ and $6.00\mu$.

A solution of 0.400 g of 3-iodomethyl-7β-phenylacetylamino-3-cephem-4-carboxylic acid diphenylmethyl ester in 15 ml of 90% strength aqueous acetic acid is cooled to 0° C. in an ice bath and 2.0 g of zinc dust are added in portions whilst stirring well. After a reaction time of 30 minutes at 0° C. the unreacted zinc dust is filtered off by means of a suction filter covered with a layer of diatomaceous earth; the filter residue is repeatedly suspended in fresh methylene chloride and again filtered. The combined filtrates are concentrated under reduced pressure, mixed with absolute toluene and evaporated to dryness under reduced pressure. The residue is taken up in 50 ml of methylene chloride and 30 ml of an 0.5 molar aqueous dipotassium hydrogen phosphate solution, whilst stirring; the aqueous phase is separated off, re-extracted with two portions of methylene chloride, each of 30 ml, and discarded. The organic extracts are repeatedly washed with a saturated aqueous sodium chloride solution, dried over magnesium sulphate and evaporated under reduced pressure. The residue is chromatographed on a column of 22 g of silica gel (with addition of 10% of water). The 3-methylene-7β-phenylacetylamino-cepham-4α-carboxylic acid diphenylmethyl ester is eluted with methylene chloride, and with methylene chloride containing 2% of methyl acetate, and is crystallised from a mixture of methylene chloride and hexane, melting point 144°-147° C.; $[\alpha]_D^{20} = -18° \pm 1°$ (c=0.715 in chloroform); ultraviolet absorption spectrum (in 95% strength aqueous ethanol): $\lambda_{max}=254$ m$\mu$($\epsilon=1,540$) and 260 m$\mu$ ($\epsilon=1,550$); infrared absorption spectrum (in methylene chloride): characteristic bands at $2.94\mu$, $5.65\mu$, $5.74\mu$, $5.94\mu$, $6.26\mu$ and $6.67\mu$.

EXAMPLE 2

A solution of 1.53 g of 3-formyl-7β-phenylacetylamino-2-cephem-4α-carboxylic acid diphenylmethyl ester in 40 ml of methylene chloride is cooled to 0° C. and 0.61 g of 3-chloroperbenzoic acid is added. The mixture is left to stand for one hour whilst warming to room temperature and is thereafter successively washed with 5% strength aqueous sodium bisulphite solution, 0.5 molar aqueous dipotassium hydrogen phosphate solution and water; the aqueous wash solutions are twice extracted with methylene chloride and then discarded. The organic phase is dried over magnesium sulphate and evaporated under reduced pressure.

The yellow jelly-like residue, containing 3-formyloxy-7β-phenylacetylamino-cephem-4-carboxylic acid diphenylmethyl ester, in which the ring double bond is preferably in the 3-position, is stirred for one hour at 0° C. with 30 ml of tetrahydrofurane and 30 ml of an 0.5 molar sodium bicarbonate solution and the mixture is concentrated under reduced pressure to a volume of about 25 ml. It is diluted with 25 ml of water and then extracted twice with ethyl acetate. The organic phase is washed with water, dried over magnesium sulphate and evaporated under reduced pressure. The residue is chromatographed on 65 g of silica gel. 7β-Phenylacetylaminocepham-3-one-4ξ-carboxylic acid diphenylmethyl ester is eluted with methylene chloride containing 2-3% of acetone and is lyophilised from dioxane; the product, which according to thin layer chromatography is not quite pure, is identical with the product of the process described in Example 1 and is used, without further purification, as a starting material.

The starting material can be manufactured as follows: A suspension of 3.40 g of 3-acetoxymethyl-7β-phenylacetylamino-2-cephem-4α-carboxylic acid in 70 ml of distilled water is mixed with 1N aqueous sodium hydroxide solution, whilst stirring with a Vibro-mixer, until a pH value of 7.3 is reached. The solution is warmed to 35° C. in a thermostatic bath and 0.4 g of the cell lyophilisate from *Bacillus subtilis* ATCC 6633, in 3 ml of water is added. The pH value is kept constant at 7.4 by adding 1N aqueous sodium hydroxide solution; after about 2½ hours half the theoretical consumption of sodium hydroxide is reached. The mixture is left to complete reaction until no further sodium hydroxide is consumed and the pH value of the reaction solution no longer changes even after standing for several hours at room temperature. It is covered with 300 ml of cooled ethyl acetate and acidified with 5 molar aqueous phosphoric acid to pH 2.0, whilst stirring well. After separating the layers, the aqueous phase is saturated with sodium chloride and extracted with two further portions each of 250 ml of cold ethyl acetate. The combined organic phases are washed five times with 50 ml portions of a saturated aqueous sodium chloride solution, dried over sodium sulphate and evaporated. The residue consists of chromatographically pure 3-hydroxymethyl-7β-phenylacetylamino-2-cephem-4α-carboxylic acid which after repeated crystallisation from a mixture of ethyl acetate and cyclohexane is in the form of white needle-shaped crystals which melt at 156°–156.5° C.

A solution of 0.7 g of 3-hydroxymethyl-7β-phenylacetylamino-2-cephem-4α-carboxylic acid in 30 ml of a 4:1 mixture of dioxane and methanol is treated with 0.507 g of diphenyldiazomethane in 5.07 ml of dioxane and the mixture is left to stand at room temperature; over the course of 90 minutes, further quantities of diphenyldiazomethane are added in portions until the slight discolouration persists. The mixture is then evaporated to dryness and the residue is crystallised from a mixture of ethyl acetate and cyclohexane; 3-hydroxymethyl-7β-phenylacetylamino-2-cephem-4α-carboxylic acid diphenylmethyl ester, thus obtainable, is in the form of fine colourless needles which melt at 179°–179.5° C.; $[\alpha]_D^{20} = +390° \pm 1°$ (c=1.174 in chloroform); thin layer chromatogram, silica gel: Rf=0.35 (system: benzene/acetone 4:1); ultraviolet absorption spectrum (95% strength aqueous ethanol: $\lambda_{max}$=250 mμ ($\epsilon$=6,500) and $\lambda_{min}$=245 mμ ($\epsilon$=6,400); infrared absorption spectrum: Caracteristic bands at 2.74μ, 2.89μ, 5.58μ, 5.71μ, 5.90μ, 6.61μ and 6.65μ (in methylene chloride) and at 3.00μ, 3.07μ, 5.62μ, 5.71μ, 6.04μ, 6.52μ, 6.68μ, 7.10μ, 7.42μ 8.20 and 8.52μ (in mineral oil).

A mixture of 5.14 g of 3-hydroxymethyl-7β-phenylacetylamino-2-cephem-4α-carboxylic acid diphenylmethyl ester in 150 ml of acetone is treated dropwise, at −15° C., with a chromic acid solution (manufactured by dissolving 267 g of chromium-VI oxide in 230 ml of concentrated sulphuric acid and 400 ml of water and diluting with water to 1,000 ml) until the orange-brownish discolouration persists; after 20 minutes, 4.5 ml of the reagent have been consumed. The mixture is stirred for 20 minutes at −10° C., 0.5 ml of isopropanol is added and the whole is concentrated under reduced pressure. The concentrate is diluted with 50 ml of water and extracted with ethyl acetate. The organic extract is washed with water, dried over magnesium sulphate and evaporated. The residue is recrystallised from a mixture of ethyl acetate and cyclohexane and yields 3-formyl-7β-phenylacetylamino-2-cephem-4α-carboxylic acid diphenylmethyl ester, melting point 175.5°–176° C. (with decomposition); thin layer chromatogram (silica gel): Rf=0.35 (system: toluene/acetone, 4:1) and Rf=0.58 (system: toluene/acetone 65:35); ultraviolet absorption spectrum (in 95% strength ethanol): $\lambda_{max}$=289 mμ ($\epsilon$=20,200); infrared absorption spectrum (in mineral oil): Characteristic bands at 3.00μ, 5.63μ, 5.76μ, 5.95μ, 5.99μ and 6.07μ.

EXAMPLE 3

A stream of oxygen and ozone (containing 0.35 mmol of ozone per minute) is passed for 4 minutes through a solution, cooled to −60° C., of 0.553 g of the 4-methylphenylsulphonate of 7β-amino-3-methylene-cepham-4α-carboxylic acid diphenylmethyl ester in 50 ml of methanol. After a further 5 minutes, the pale blue-coloured solution is treated with 0.3 ml of dimethyl sulphide. The mixture is stirred for 15 minutes at −70° C., for one hour at −12° C. and for one hour in an ice bath and is then evaporated. The residue is taken up in a small amount of methylene chloride, diethyl ether is then added until the mixture turns cloudy, and the mixture is left to stand. The microcrystalline, reddish-coloured pulverulent precipitate is filtered off and yields the 4-methylphenylsulphonate of 7β-amino-cepham-3-one-4α-carboxylic acid diphenylmethyl ester which is mainly present in the enol form as the 4-methylphenylsulphonate of 7β-amino-3-cephem-3-ol-4-carboxylic acid diphenylmethyl ester, melting point=143°–145° C. (with decomposition); thin layer chromatogram (silica gel) Rf~0.28 (system: ethyl acetate/pyridine/water, 85:10:5); ultraviolet absorption spectrum (in ethanol): $\lambda_{max}$=262 mμ ($\epsilon$=3,050) and 282 mμ ($\epsilon$=3,020); infrared absorption spectrum (in methylene chloride): characteristic bands at 5.58μ, 5.77μ (shoulder), 6.02μ and 6.22μ.

The starting material can be manufactured as follows:

A solution, cooled to −15° C., of 2.0 g of 3-methylene-7β-phenylacetylamino-cepham-4α-carboxylic acid diphenylmethyl ester in 80 ml of absolute methylene chloride is mixed with 3.2 ml of absolute pyridine and 32 ml of an 8% strength solution of phosphorus pentachloride in methylene chloride and stirred for one hour under a nitrogen atmosphere at a temperature between −10° C. and −5° C. The reaction mixture is then cooled to −25° C., mixed with 25 ml of absolute methanol and stirred for one hour at −10° C. and then for 1.5 hours at room temperature. 80 ml of an 0.5 molar aqueous solution of potassium dihydrogen phosphate are then added, the pH value is adjusted to 2 with 20% strength aqueous phosphoric acid and the mixture is stirred for 30 minutes at room temperature.

The organic phase is separated off, the aqueous phae is twice re-extracted with 150 ml of methylene chloride at a time and the organic solutions are combined, dried over sodium sulphate and evaporated. The oily residue is taken up in 25 ml of ethyl acetate and a solution of 1.14 g of 4-methylphenylsulphonic acid monohydrate in 25 ml of ethyl acetate is added at 0° C. A voluminous precipitate separates out, which is filtered off, rinsed with cold ethyl acetate and diethyl ether, dried and recrystallised, from a mixture of methylene chloride and diethyl ether. The 4-methylphenylsulphonate of 7β-amino-3-methylene-cepham-4α-carboxylic acid diphenylmethyl ester is thus obtained in the form of colourless needless, melting point 153°–155° C.; $[\alpha]_D = -14° \pm 1°$ (c=0.97 in methanol); ultraviolet absorption spectrum (in ethanol): $\lambda_{max}$=257μ ($\epsilon$=1,500); infrared absorption spectrum (in methylene chloride): characteristic bands at 3.5μ, 5.60μ, 5.73μ, 8.50μ, 9.68μ and 9.92μ.

EXAMPLE 4

An oxygen-ozone stream, containing 0.21 mmol of ozone/minute, is passed for one hour into a solution, cooled to −70° C., of 5.0 g of 3-methylene-7β-(D-α-tert.-butoxycarbonylamino-α-phenylacetylamino)-cepham-4α-carboxylic acid diphenylmethyl ester in 500 ml of methylene chloride, whilst stirring vigorously. After a further 10 minutes, 3 ml of dimethyl sulphide are added to the reaction mixture, which is stirred for one hour at −65° C. and for 2 hours at room temperature and then evaporated under reduced pressure. The crude product, which contains the 7β-(D-α-tert.-butoxycarbonylamino-α-phenylacetyl-amino)-cepham-3-one 4ξ-carboxylic acid diphenylmethyl ester, in 150 ml of methanol, is treated at 0° C. with an excess amount of a solution of diazomethane in diethyl ether, stirred for 15 minutes and subsequently evaporated. A yellowish foam is obtained, which is chromatographed on 200 g of silica gel. Amorphous 3-methoxy-7β-(D-α-tert.-butoxycarbonylamino-α-phenylacetylamino)-3-cephem-4- carboxylic acid diphenylmethyl ester is eluted with a 3:1 mixture of toluene and ethyl acetate. Thin layer chromatogram (silica gel): Rf=0.22 (system: toluene-/ethyl acetate, 3:1); infrared absorption spectrum (in methylene chloride): characteristic bands at 2.94μ, 5.60μ, 5.85μ, 6.23μ and 6.70μ.

The starting material can be manufactured as follows:

A chromatography column (diameter: 3 cm) is filled with 350 g of zinc grit, which is amalgamated for 10 minutes with an 0.1 molar solution of mercury-II chloride in 0.1N hydrochloric acid and is washed with a large amount of water and subsequently with a small amount of 1N hydrochloric acid. A solutio of 55 g of green chromium-III chloride hexahydrate in 55 ml of water and 11 ml of 2N sulphuric acid is poured into the reduction tube and the outlet speed is regulated so that a chromium-II chloride solution of a pure blue colour drips into the reaction vessel, which is kept under a nitrogen atmosphere. The blue chromium-II chloride solution is subsequently treated with a solution of 92 g of sodium acetate in 180 ml of air-free water, whereupon the solution assumes a red discolouration and finely crystalline chromium-II acetate precipitates. After completion of the precipitation, the supernatant solution is removed and the chromium-II acetate is twice washed with 250 ml of air-free water at a time. A solution of 10.0 g of 3-acetoxymethyl-7β-(D-α-tert.-butoxycarbonyl-amino-phenylacetyl-amino)-3-cephem-4-carboxylic acid in 200 ml of dimethylsulphoxide is added to the moist chromium-II acetate and the reaction mixture is stirred for 15 hours under a nitrogen atmosphere at room temperature. For working up, the reaction mixture is aerated for 30 minutes and after addition of 1,000 g of a polystyrenesulphonic ion exchanger in the Na ⓡ form (Dowex 50 W) and 1,000 ml of water, the whole is stirred for one hour. After removing the ion exchanger, the pH value of the solution is adjusted to 2 with 6N hydrochloric acid and the aqueous phase is extracted three times with 2,000 ml of ethyl acetate at a time. The organic extracts are washed once with 1,000 ml of a saturated aqueous sodium chloride solution, dried over magnesium sulphate and evaporated.

The resulting crude product is dissolved in 100 ml of methanol and stirred with a solution of 6 g of diphenyl-diaazomethane in 30 ml of benzene for 1 hour at room temperature. The crude product obtained after the evaporation is chromatographed on 500 g of silica gel; 3-methylene-7β-(D-α-tert.-butoxycarbonylamino-α-phenylacetylamino)-cepham-4α-carboxylic acid diphenylmethyl ester is eluted with a 4:1 mixture of petroleum ether and diethyl ether; after crystallisation from a mixture of methylene dichloride and hexane, the product melts at 156°-158° C.; [α]$_D$=−50°±1° (c=0.713, chloroform); ultraviolet absorption spectrum in 95% strength aqueous ethanol): λ$_{max}$=258μ (ε=990); infrared absorption spectrum (in methylene chloride): characteristic bands at 2.94μ, 5.64μ, 5.74μ, 5.88μ (shoulder) and 6.71μ.

EXAMPLE 5

A solution of 1.0 g of 3-methylene-7β-phenylacetylamino-cepham-4α-carboxylic acid diphenylmethyl ester in 250 ml of methylene chloride is treated for 8½ minutes at −70° C. with an oxygen-ozone mixture (0.265 mmol of ozone/minute) and 1 ml of dimethyl sulphide is added to the reaction mixture. The mixtureis stirred for 30 minutes at −70° C. and for 1½ hours at room temperature and is then evaporated to dryness under reduced pressure. The residue, containing a mixture of 7β-phenylacetylamino-cepham-3-one-4ξ-carboxylic acid diphenylmethyl ester and of 7β-phenylacetamino-cepham-3-one-4α-carboxylic acid diphenylmethyl ester 1-oxide is taken up in 50 ml of methanol and treated with an excess of diazomethane (in the form of a solution in diethyl ether) at 0° C. The whole is stirred for one hour at 0° C. and then evaporated under reduced pressure. The residue is chromatographed on 50 g of silica gel. Elution with a 4:1 mixture of toluene and ethyl acetate yields 3-methoxy-7β-phenylacetylamino-2-cephem-4α-carboxylic acid diphenylmethyl ester of Rf=0.57 (system: toluene/ethyl acetate, 1:1); melting point 174°-177° C. after recrystallisation from a mixture of methylene chloride and pentane; ultraviolet absorption spectrum (in 95% strength aqueous ethanol): λ$_{max}$=258 mμ (ε=4,000); infrared absorption spectrum (in methylene chloride): characteristic bands at 2.96μ, 5.60μ, 5.71μ, 5.92μ, 6.15μ and 6.66μ; followed by 3-methoxy-7β-phenylacetylamino-3-cephem-4-carboxylic acid diphenylmethyl ester of Rf∼0.37 (system: toluene/ethyl acetate 1:1): ultraviolet absorption spectrum (in 95% strength aqueous ethanol): λ$_{max}$=258 mμ (ε=6,340), λ$_{max}$=264 mμ (ε=6,350) and λ$_{shoulder}$=261 mμ (ε=5,600); infrared absorption spectrum (in methylene chloride): characteristic bands at 2.94μ, 3.02μ, 5.62μ, 5.67μ (shoulder), 5.81μ, 5.92μ, 6.23μ and 6.67μ; elution with ethyl acetate yields 3-methoxy-7β-phenylacetylamino-3-cephem-4-carboxylic acid diphenylmethyl ester 1-oxide of Rf=0.31 (system: ethyl acetate); melting point 152°-155° C. after crystallisation from a mixture of acetone and diethyl ether; ultraviolet absorption spectrum (in 95% strength aqueous ethanol): λ$_{max}$=288 mμ (ε=3,610) and λ$_{shoulder}$=247 mμ; infrared absorption spectrum (in methylene chloride): characteristic bands at 2.94μ, 5.59μ, 5.81μ, 5.95μ, 6.22μ and 6.61μ.

EXAMPLE 6

A solution of 0.50 g of 3-methylene-7β-phenylacetylamino-cepham-4α-carboxylic acid diphenylmethyl ester in 50 ml of methanol is treated with an oxygen-ozone mixture at −70° C. until a blue colouration starts to appear. The excess ozone is driven off with nitrogen; 0.5 ml of dimethyl sulphide is added and the mixture is stirred for 1½ hours at room temperature. The reaction mixture, containing a mixture of 7β-phenylacetylamino-cepham-3-one-4ξ-carboxylic acid diphenylmethyl ester and of 7β-phenylacetylamino-cepham-3-one-4ξ-carboxylic acid diphenylmethyl ester 1-oxide is then evaporated to dryness under reduced pressure. The residue is taken up in 10 ml of pyridine, 5 ml of acetic anhydride are added and the mixture is left to stand for 16 hours at 0° C. It is evaporated to dryness under a high vacuum; the residue is taken up in ethyl acetate and the organic solution is washed with a saturated aqueous sodium bicarbonate solution and a saturated aqueous sodium chloride solution, dried over sodium sulphate and evaporated under reduced pressure. The residue is chromatographed on 30 g of silica gel, 3-acetoxy-7β-phenylacetylamino-3-cephem-4-carboxylic acid diphenylmethyl ester being eluted with a 4:1 mixture of toluene and ethyl acetate. The product is crystallised from a mixture of acetone and diethyl ether, melting point 158°-160° C.; ultraviolet absorption spectrum (in 95% strength aqueous ethanol): λ$_{max}$=258 mμ (ε=6,580) and 264 mμ (ε=6,550); infrared absorption spectrum (in methylene chloride): characteristic bands at 2.95μ, 5.59μ, 5.69μ (shoulder), 5.78μ, 5.91μ, 6.06μ (shoulder) and 6.67μ.

EXAMPLE 7

A solution of 1.0 g of 3-methylene-7β-phenylacetylamino-cepham-4α-carboxylic acid diphenylmethyl ester in 100 ml of methanol is treated with an oxygen-ozone mixture at −70° C. until a blue colouration begins to show, and the excess ozone is expelled with nitrogen. The reaction mixture is treated with 0.4 ml of dimethylsulphide and is stirred for 30 minutes at room temperature. It is then cooled to 0° C. and a solution of 0.10 g of sodium borohydride in 5 ml of water is added to the reaction mixture, which contains 7β-phenylacetylamino-cepham-3-one-4ξ-carboxylic acid diphenylmethyl ester and 7β-phenylacetylamino-cepham-3-one-4ξ-carboxylic acid diphenylmethyl ester-1-oxide. The reaction is allowed to proceed for 30 minutes at 0° C., the ph value is adjusted to about 6 by adding acetic acid and the reaction mixture is evaporated under reduced pressure. The residue is taken up in ethyl acetate; the organic solution is washed with a saturated aqueous sodium bicarbonate solution and a saturated aqueous sodium chloride solution, dried over sodium sulphate and evaporated under reduced pressure. The residue is chromatographed on 50 g of silica gel. 3ξ-Hydroxy-7β-phenylacetylamino-cepham-4ξ-carboxylic acid diphenylmethyl ester is eluted with a 2:1 mixture of toluene and ethyl acetate and after crystallisation from a mixture of acetone and diethyl ether melts at 157°–160° C.; $[\alpha]_D = +80° \pm 1°$ (c=0.492 in dioxane): $\lambda_{max} = 258\mu$ ($\epsilon = 850$); infrared absorption spectrum (in methylene chloride): characteristic bands at 2.82μ, 2.94μ, 5.63μ, 5.74μ, 5.92μ, 6.25μ and 6.63μ.

EXAMPLE 8

A solution of 0.400 g of 7β-(D-α-tert.-butoxycarbonylamino-α-phenyl-acetylamino)-3-methylene-cepham-4α-carboxylic acid diphenylmethyl ester in 40 ml of methylene chloride is cooled to 0° C. and 0.0835 g of tetracyanoethylene are added. The yellow solution is treated, at 0° C., with an oxygen/ozone mixture until 0.773 mmol of ozone has been consumed and is then evaporated to dryness under a high vacuum at about 35° C. The residue, containing 7β-(D-α-tert.-butoxycarbonylamino-α-phenyl-acetylamino)-cepham-3-one-4-ξ-carboxylic acid diphenylmethyl ester is taken up in 50 ml of methanol, treated with a solution of diazomethane in diethyl ether until the yellow colouration persists, and then evaporated under reduced pressure at about 35° C. 0.1 g of the residue is worked up by means of a layer chromatogram (silica gel; system: ethyl acetate/toluene, 1:1), 3-methoxy-7β-(D-α-tert.-butoxycarbonylamino-α-phenyl-acetylamino)-3-cephem-4-carboxylic acid diphenylmethyl ester, which is identical with the product of Example 4, being obtained at Rf∼0.5, and 7β-(D-α-tert.-butoxycarbonylamino-α-phenyl-acetylamino)-3-methylene-cepham-4α-carboxylic acid diphenylmethyl ester being obtained at Rf∼0.6.

EXAMPLE 9

A solution of 0.2 g of 7β-(D-α-tert.-butoxycarbonylamino-α-phenyl-acetylamino)-3-methylene-cepham-4α-carboxylic acid diphenylmethyl ester in 3 ml of methylene chloride is cooled to −22° C. and treated, whilst cooling, first with 0.026 ml of pyridine and then with an ozone-oxygen mixture until 1.31 mmols of ozone have been passed through. The reaction mixture is evaporated to dryness in a high vacuum and the residue is purified by thin layer chromatography. 7β-(D-α-tert.-Butoxycarbonylamino-α-phenyl-acetylamino)-cepham-3-one-4ξ-carboxylic acid diphenylmethyl ester shows an Rf-value of ∼0.05 (silica gel; system: toluene/acetone/methanol/acetic acid, 80:10:4:5); infrared absorption spectrum (in methylene chloride): Characteristic bands at 2.94μ, 3.40μ, 5.62μ, 5.77μ, 5.75–5.95μ (broad band), 6.21μ and 6.88μ.

EXAMPLE 10

The manufacture of 7β-(D-α-tert.-butoxycarbonylamino-α-phenyl-acetylamino)-cepham-3-one-4ξ-carboxylic acid diphenylmethyl ester from 7β-(D-α-tert.-butoxycarbonylamino-α-phenylacetylamino)-3-methylene-cepham-4α-carboxylic acid diphenylmethyl ester is advantageously carried out continuously: A 1% strength solution of 7β-(D-α-tert.-butoxycarbonylamino-α-phenylacetylamino)-3-methylene-cepham-4α-carboxylic acid diphenylmethyl ester in methylene chloride, which has been precooled to 0° C., is allowed to flow through a reactor tube (about 3 cm diameter) which is filled with packings (for example Raschig rings) and is cooled to 0° C., and an ozone-oxygen mixture which provides 0.245 mmol of ozone per minute is passed through the tube in counter-current. The gas stream is regulated so that 700 ml of the gas mixture flow hourly through the reactor tube. The dwell time of the solution of 7β-(D-α-tert.-butoxycarbonylamino-α-phenyl-acetylamino)-3-methylene-cepham-4α-carboxylic acid diphenylmethyl ester in the reactor tube is 15 seconds. The reaction solution containing the ozonide is allowed to run directly into a receiver containing a solution of dimethylsulphide in methylene chloride until it contains an excess of 5% of dimethylsulphide; the receiver is then changed. The solution of 7β-(D-α-tert.-butoxycarbonylamino-α-phenylacetylamino)-cepham-3-one-4ε-carboxylic acid diphenylmethyl ester, thus obtainable, is evaporated under reduced pressure at about 35° C. and the residue is taken up in methanol and treated with a solution of diazomethane in diethyl ether, for example as described in Example 4. 3-Methoxy-7β-(D-α-tert.-butoxycarbonylamino-α-phenyl-acetylamino)-3-cephem-4-carboxylic acid diphenylmethyl ester, which is identical with the product of Example 4, is thus obtained.

EXAMPLE 11

A mixture of 5 g of 3-methylene-7β-(D-α-tert.-butoxycarbonylamino-α-phenylacetylamino)-cepham-4α-carboxylic acid diphenylmethyl ester and 500 ml of methylene chloride is treated, at −70° C., with 1.15 equivalents of ozone according to the process described in the preceding examples, 2 ml of dimethylsulphide are subsequently added and the mixture is stirred for one hour at −70° C. and 2 hours at room temperature and is then evaporated under reduced pressure. The residue, containing 7β-(D-α-tert.-butoxycarbonylamino-α-phenylacetylamino)-cepham-3-one-4ξ-carboxylic acid diphenylmethyl ester, is dissolved in 150 ml of methanol and a solution of diazo-n-butane in diethyl ester is added at 0° C. until the yellow colouration persists. After 15 minutes, the solution is evaporated under reduced pressure and the residue is purified by means of preparative layer chromatography (silica gel; 1.5 mm thickness; plates of size 16×100 cm; system: toluene/ethyl acetate, 72:25). The zone which is visible under ultraviolet light, and has an Rf value of about 0.35, yields 3-n-butoxy-7β-(D-α-tert.-butoxycarbonylamino-α-phenylacetylamino)-3-cephem-4-carboxylic acid diphenylmethyl ester, which is again purified by renewed chromatography on silica gel and is lyophilised from dioxane, $[\alpha]_D^{20} = +11° \pm 1°$ (c=0.98 in chloroform); ultraviolet absorption spectrum (in 95% strength aqueous ethanol): $\lambda_{max} = 264$ mμ ($\epsilon = 6,100$); infrared absorption spectrum (in methylene chloride): characteristic bands at 2.88μ, 5.63μ, 5.84μ (shoulder), 5.88μ, 6.26μ and 6.71μ.

EXAMPLE 12

A solution of 0.258 g of 3-methylene-7β-phenylacetylamino-cepham-4α-carboxylic acid diphenylmethyl ester 1-oxide in 50 ml of methanol is treated with an oxygen/ozone mixture (20 mmols of ozone per minute) at −65° until the blue colouration persists. The reaction mixture is thereafter treated with 0.5 ml of dimethylsulphide, stirred for 20 minutes at −65° C. and 30 minutes at room temperature and evaporated under reduced pressure. The residue, containing 7β-phenylacetylamino-cepham-3-one-4ξ-carboxylic acid diphenylmethyl ester 1-oxide is taken up in 20 ml of methanol and treated, at 0° C., with an ethereal solution of diazomethane in diethyl ether until the yellow colouration persists. After standing for 15 minutes, the reaction mixture is evaporated under reduced pressure. The residue is purified by means of preparative thin layer chromatography; the zone which is visible under ultraviolet light ($\lambda = 254$ mμ), of Rf~0.20 (system: ethyl acetate; identification with iodine) is eluted with a 1:1 mixture of acetone and methanol and 3-methoxy-7β-phenylacetylamino-3-cephem-4-carboxylic acid diphenylmethyl ester 1-oxide is thus obtained, ultraviolet absorption spectrum (in 95% strength aqueous ethanol): $\lambda_{max} = 276$ mμ ($\epsilon = 7,500$); infrared absorption spectrum (in methylene chloride): characteristic bands at 2.94μ, 5.56μ, 5.81μ, 5.92μ, 6.22μ and 6.67μ.

The starting material used in the above example can be manufactured as follows: a solution, cooled to 0° C., of 0.50 g of 3-methylene-7β-phenylacetylamino-cepham-4α-carboxylic acid diphenylmethyl ester in 50 ml of methylene chloride is mixed with a solution of 0.19 g of 3-chloroperbenzoic acid in 10 ml of methylene chloride and the mixture is stirred for 30 minutes in an ice bath under a nitrogen atmosphere. The reaction mixture is diluted with 100 ml of methylene chloride, washed twice with 50 ml of a saturated aqueous sodium bicarbonate solution and with 50 ml of a saturated aqueous sodium chloride solution, dried over sodium sulphate and evaporated under reduced pressure. The residue is chromatographed on 50 g of silica gel. 3-Methylene-7β-phenylacetylaminocephem-4α-carboxylic acid diphenylmethyl ester 1-oxide is eluted with methylene chloride, containing 3–5% of acetone, and crystallised from a mixture of acetone, diethyl ether and hexane, melting point = 172°–175° C.; $[\alpha]_D^{20} = -68°$ (c=0.925 in chloroform); thin layer chromatogram (silica gel; identification with iodine): RF~0.25 (system: toluene/ethyl acetate, 1:1); ultraviolet absorption spectrum (in 95% strength aqueous ethanol): no specific absorption; infrared absorption spectrum (in methylene chloride): characteristic bands at 2.96μ, 5.60μ, 5.74μ, 5.92μ, 6.24μ, 6.63μ and 9.60μ.

EXAMPLE 13

A solution, cooled to −70° C., of 8.2 g of 7β-(D-α-tert.-butoxycarbonylamino-α-phenylacetylamino)-3-methylene-cepham-4α-carboxylic acid diphenylmethyl ester in 800 ml of methylene chloride is treated for 34 minutes with a stream of oxygen/oxone (0.49 mmol of ozone per minute), and is then treated with 3.5 ml of dimethylsulphide and stirred for one hour at −70° C. and for 2 hours at room temperature. After evaporation under reduced pressure, the oily residue containing the 7β-(D-α-tert.-butoxycarbonylamino-α-phenylacetylamino)-cepham-3-one-4ξ-carboxylic acid diphenylmethyl ester is dissolved in 300 ml of benzene, 3.28 g of 1-ethyl-3-(4-methylphenyl)-triazene are added and the whole is boiled for one hour under reflux in a nitrogen atmosphere and is then evaporated under reduced pressure. The residue is chromatographed on 360 g of silica gel. The amorphous 3-ethoxy-7β-(D-α-tert.-butoxycarbonylamino-α-phenylacetylamino)-3-cephem-4-carboxylic acid diphenylmethyl ester is eluted with a 4:1 mixture of toluene and ethyl acetate, thin layer chromatography (silica gel): Rf~0.28 (system: toluene/ethyl acetate, 3:1); ultraviolet absorption spectrum (in 95% strength aqueous ethanol): $\lambda_{max} = 258$ mμ ($\epsilon = 7,000$) and $\lambda_{max} = 264$ mμ ($\epsilon = 6,900$); infrared absorption spectrum (in methylene chloride): characteristic bands at 2.96μ, 5.64μ, 5.90μ, 6.28μ and 6.73μ.

EXAMPLE 14

A solution of 15 g of 3-methylene-7β-(D-α-tert.-butoxycarbonylamino-α-phenylacetylamino)-cephem-4α-carboxylic acid diphenylmethyl ester in 1,500 ml of methylene chloride is treated for 62 minutes, at −65° C., with a mixture of oxygen and ozone, containing 0.5 mmol of ozone per minute, and is then mixed with 8.7 ml of dimethylsulphide at −70° C. The mixture is stirred for 1 hour at −70° C. and for 2 hours at room temperature and is evaporated under reduced pressure. The residue, containing the crude 7β-(D-α-tert.-butoxycarbonylamino-α-phenylacetylamino)-cepham-3-one-4ξ-carboxylic acid diphenylmethyl ester, is dissolved in 350 ml of benzene, 11 g of 1-benzyl-3-(4-methylphenyl)-triazene are added and the whole is then boiled for 4 hours under reflux. After cooling, it is washed with 100 ml of 2N aqueous hydrochloric acid and with a saturated aqueous sodium chloride solution; the organic phase is dried over sodium sulphate and evaporated under reduced pressure. The reduced is chromatographed on 650 g of silica gel; with toluene, containing 15% of ethyl acetate, amorphous 3-benzyloxy-7β-(D-α-tert.-butoxycarbonylamino-α-phenylacetylamino)-3-cephem-4-carboxylic acid diphenylmethyl ester, which according to thin layer chromatography is a single substance, is eluted; thin layer chromatogram (silica gel; development with iodine): Rf~0.34 (system: toluene/ethyl acetate 3:1); $[\alpha]_D^{20} = +7° \pm 1°$ (c=0.97 in chloroform); ultraviolet absorption spectrum (in 95% strength aqueous ethanol): $\lambda_{max} = 258$ mμ ($\epsilon = 6,800$), and 264 mμ ($\epsilon = 6,800$), and $\lambda_{shoulder} = 280$ mμ ($\epsilon = 6,300$); infrared absorption spectrum (in methylene chloride): characteristic bands at 2.96μ, 5.63μ, 5.88μ, 6.26μ and 6.72μ.

EXAMPLE 15

A solution of 1.59 g of 7β-(5-benzoylamino-5-diphenylmethoxycarbonyl-valeryl-amino)-3-methylene-cepham-4α-carboxylic acid diphenylmethyl ester in 150 ml of methylene chloride is cooled to −70° C.

and treated for 12 minutes and 43 seconds, whilst stirring vigorously, with a mixture of oxone and oxygen, containing 0.2 mmol of ozone per minute, and then with 1 ml of dimethylsulphide. The mixture is stirred for 5 minutes at −70° C. and for 30 minutes at room temperature and is evaporated under reduced pressure. The residue, containing 7β-(5-benzoylamino-5-diphenylmethoxycarbonyl-valeryl-amino)-cepham-3-one-4ξ-carboxylic acid diphenylmethyl ester, is dissolved in 40 ml of methanol, cooled in an ice bath, and treated with a solution of diazomethane in diethyl ether until the yellow colouration persists. The reaction mixture is evaporated under reduced pressure and the residue is chromatographed on 100 g of silica gel. 7β-(5-Benzoylamino-5-diphenylmethoxycarbonyl-valeryl-amino)-3-methoxy-3-cephem-4-carboxylic acid diphenylmethyl ester is eluted with a 1:1 mixture of toluene and ethyl acetate and obtained as an amorphous product, thin layer chromatogram (silica gel): Rf=0.45 (system: toluene/ethyl acetate, 1:1); ultraviolet absorption spectrum (in 95% strength aqueous ethanol): $\lambda_{shoulder}$=258 mμ ($\epsilon$=7,450), 264 mμ ($\epsilon$=7,050) and 268 mμ ($\epsilon$=6,700); infrared absorption spectrum (in methylene chloride): characteristic bands at 5.65μ, 5.78μ, 6.03μ and 6.64μ.

The starting material can be manufactured as follows:

A solution of 50 g of the sodium salt of cephalosporin C in 1,500 ml of 10% strength aqueous dipotassium hydrogen phosphate is diluted with 1,200 ml of acetone and 21 g of benzoyl chloride are added at 0° C. The mixture is stirred for 30 minutes at 0° C. and for 45 minutes at 20° C., whilst keeping the pH value constant at 8.5 by addition of a 50% strength aqueous tripotassium phosphate solution. It is concentrated to about half its volume under reduced pressure, washed with ethyl acetate, acidified to pH 2.0 with 20% strength aqueous phosphoric acid and extracted with ethyl acetate. The organic phase is dried and evaporated under reduced pressure; the residue, recrystallised from acetone, yields N-benzoyl-cephalosporin C, melting point 117°–119° C.; thin layer chromatogram (silica gel): Rf=0.37 (system: n-butanol/acetic acid/water, 75:7.5:21) and Rf: 0.08 (system: ethyl acetate/pyridine/acetic acid/water, 62:21:6:11).

A solution of 4.7 g of N-benzoyl-cephalosporin C in 85 ml of 0.5M molar aqueous dipotassium hydrogen phosphate solution and 9 ml of dimethylformamide is stirred with 4.7 g of aluminium amalgam for 45 minutes at pH 6.0 and 45° C., whilst keeping the pH value constant by addition of 20% strength aqueous phsophoric acid. 100 ml of ice are added, and the mixture is covered with cold ethyl acetate and adjusted to pH 2.0 with concentrated phosphoric acid. The mixture is saturated with sodium chloride, the organic phase is separated off and the aqueous phase is twice rinsed with ethyl acetate.

The combined organic extracts are washed with saturated aqueous sodium chloride solution and dried over sodium sulphate and on evaporation under reduced pressure yield a residue which is caused to crystallised in ethyl acetate. It is slowly diluted with 15 ml of a 2:3 mixture of ethyl acetate and hexane and filtered after standing for 2 hours at −5° C., and after crystallisation from a 1:4 mixture of ethyl acetate and diethyl ether, 7β-(5-benzoylamino-5-carboxy-valerylamino)-3-methylene-cepham-4α-carboxylic acid is obtained, melting point 82°–89° C. (with decomposition); thin layer chromatogram (silica gel): Rf=0.53 (system: n-butanol/acetic acid/water, 75:7.5:21), and Rf=0.008 (system: ethyl acetate/pyridine/acetic acid/water, 62:21:6:11).

The aluminium amalgam used above can be manufactured as follows: a mixture of 3.3 g of aluminium grit and 100 ml of 50% strength aqueous sodium hydroxide solution is shaken for 30 seconds and after decanting the supernatant liquid the aluminium is washed three times with 300 ml of water at a time. The residue is treated for 3 minutes with 130 ml of an 0.3% strength aqueous mercury-II chloride solution and is washed three times with 300 ml of water at a time. The entire treatment is repeated once and the aluminium amalgam is finally washed three times with tetrahydrofurane. About 15 ml of ethyl acetate are used to transfer the product into the reaction vessel.

A solution of 2.3 g of 7β-(5-benzoylamino-5-carboxyvaleryl-amino)-3-methylene-cepham-4α-carboxylic acid in 25 ml of dixoane is treated dropwise, over the course of 10 minutes, with a solution of 2.5 g of diphenyldiazomethane in 10 ml of n-pentane. It is stirred for 30 minutes at room temperature, the excess diphenyldiazomethane is decomposed by adding a few drops of acetic acid (glacial acetic acid) and the solution is evaporated under reduced pressure. The residue is chromatographed on 80 g of silica gel, 7β-(5-benzoylamino-5-diphenylmethoxycarbonyl-valeryl-amino)-3-methylene-cepham-4α-carboxylic acid diphenylmethyl ester being eluted with a 3:1 mixture of toluene and ethyl acetate and then crystallised from a mixture of methyl acetate and cyclohexane, melting point 180°–181° C.; thin layer chromatogram (silica gel): Rf=0.24 (system: toluene/ethyl acetate, 2:1); ultraviolet absorption spectrum (in 95% strength aqueous ethanol): no characteristic bands; infrared absorption spectrum (in methylene chloride): characteristic bands at 5.66μ, 5.76μ, 5.95μ, 6.03μ, 6.64μ and 6.70μ.

EXAMPLE 16

A solution, cooled to 0° C., of 0.400 g of 7β-(D-α-tert.-butoxycarbonylamino-α-phenylacetylamino)-3-methylene-cepham-4α-carboxylic acid diphenylmethyl ester in 40 ml of methylene chloride is treated for 3.6 minutes with an ozone-oxygen mixture containing 0.21 mmol of ozone per minute, and is then mixed with 0.5 ml of dimethylsulphide and subsequently evaporated under reduced pressure. The residue, containing 7β-(D-α-tert.-butoxycarbonylamino-α-phenylacetylamino)-cepham-3-one-4ξ-carboxylic acid diphenylmethyl ester, is dissolved in 10 ml of methanol and treated with a solution of diazomethane in diethyl ether until the yellow colouration persists. The mixture is evaporated under reduced pressure and the residue is subjected to preparative layer chromatography (silica gel; system: toluene/ethyl acetate, 1:1, identification with ultraviolet light, λ=254). A mixture of 7β-(D-α-tert.-butoxycarbonylamino-α-phenylacetylamino)-3-methylene-cepham-4α-carboxylic acid diphenylmethyl ester and of 7β-(D-α-tert.-butoxycarbonylamino-α-phenylacetylamino)-3-methoxy-2-cephem-4α-carboxylic acid diphenylmethyl ester, both of Rf value 0.55, is thus obtained, followed by 7β-D-α-tert.-butoxycarbonylamino-α-phenylacetylamino)-3-methoxy-3-cephem-4-carboxylic acid diphenylmethyl ester of Rf value 0.45 and finally by a mixture of 7β-(D-α-tert.-butoxycarbonylamino-α-phenylacetylamino)-3-methoxy-3-cephem-4-carboxylic acid diphenylmethyl ester 1β-oxide of Rf value 0.17 and 1α-oxide of Rf value 0.07.

Instead of 7β-(D-α-tert.-butoxycarbonylamino-α-phenylacetylamino)-3-methylene-cepham-4α-carboxylic acid diphenylmethyl ester it is possible to use, as starting substances in the above process, 7β-(D-α-tert.-butoxycarbonylamino-α-phenylacetylamino)-3-methylene-cepham-4α-carboxylic acid 4-nitrobenzyl ester or 7β-D-α-tert.-butoxycarbonylamino-α-phenylacetylamino)-3-methylene-cepham-4α-carboxylic acid 2,2,2-trichloroethyl ester, which can be respectively obtained by treatment of the sodium salt of 7β-(D-α-tert.-butyoxycarbonylamino-α-phenylacetylamino)-3-methylene-cephem-4α-carboxylic acid with 4-nitrobenzyl bromide or of a reactive mixed anhydride of 7β-(D-α-tert.-butoxycarbonylamino-α-phenylacetylamino)-3-methylene-cepham-4α-carboxylic acid with 2,2,2-trichloroethanol, and from these starting substances to obtain, via 7β-(D-α-tert.-butoxycarbonylamino-α-phenylacetylamino)-cepham-3-one-4ξ-carboxylic acid 4-nitrobenzyl ester and 7β-(D-α-tert.-butoxycarbonylamino-α-phenylacetylamino)-cepham-3-one-4ξ-carboxylic acid 2,2,2-trichloroethyl ester respectively, 7β-(D-α-tert.-butoxycarbonylamino-α-phenylacetylamino)-3-methoxy-3-cephem-4-carboxylic acid 4-nitrobenzyl ester and 7β-(D-α-tert.-butoxycarbonylamino-α-phenylacetylamino)-3-methoxy-3-cephem-4-carboxylic acid 2,2,2-trichloroethyl ester respectively.

EXAMPLE 17

A solution of 0.250 g of the 4-methylphenylsulphonic acid salt of 7β-amino-cepham-3-one-4ξ-carboxylic acid diphenylmethyl ester, which is mainly present in the enol form of the 4-methylphenylsulphonate of 7β-amino-3-cepham-3-ol-4-carboxylic acid diphenylmethyl ester, in 10 ml of methylene chloride, is treated with 0.063 ml of trimethylchlorosilane and 0.044 ml of pyridine and stirred for 30 minutes at room temperature and then cooled to 0° C. 0.088 ml of pyridine and 0.092 ml of phenylacetic acid chloride are added, and the mixture is allowed to react for one hour at 0° C. and for a further hour at room temperature and is diluted with 5 ml of a 1:1 mixture of dioxane and water and stirred for 10 minutes. The whole is diluted with 50 ml of methylene chloride, the phases are separated and the organic solution is washed with a saturated aqueous sodium bicarbonate solution and a saturated aqueous sodium chloride solution, dried over sodium sulphate and evaporated under reduced pressure. The residue is chromatographed on silica gel; 7β-phenylacetylamino-cepham-3-one-4ξ-carboxylic acid diphenylmethyl ester is eluted with methylene chloride; thin layer chromatogram (silica gel): Rf~0.55 (system: ethyl acetate/pyridine/water, 85:10:5); ultraviolet absorption spectrum (in 95% strength aqueous ethanol): $\lambda_{max}=283$ mμ ($\epsilon=4,400$); infrared absorption spectrum (in methylene chloride): Characteristic bands at 2.94μ, 5.12μ, 5.77μ, 5.93μ, 6.21μ and 6.63μ.

EXAMPLE 18

The following compounds can be obtained analogously if suitable starting substances are chosen: 7β-[D-α-]tert.-butoxycarbonylamino-α-(4-hydroxy-phenyl)-acetylamino]-cepham-3-one-4ξ-carboxylic acid diphenylmethyl ester; 7β-[D-α-tert.-butoxycarbonylamino-α-(2-thienyl)-acetylamino]-cepham-3-one-4ξ-carboxylic acid diphenylmethyl ester; 7β-[D-α-tert.-butoxycarbonylamino-α-(3-thienyl)-acetylamino]-cepham-3-one-4ξ-carboxylic acid diphenylmethyl ester; 7β-[D-α-tert.-butoxycarbonylamino-α-(2-furyl)-acetylamino-cepham-3-one-4ξ-carboxylic acid diphenylmethyl ester; 7β-(2-thienyl)-acetylamino-cepham-3-one-4ξ-carboxylic acid diphenylmethyl ester; 7β-(1-tetrazolyl)acetylamino-cepham-3-one-4ξ-carboxylic acid diphenylmethyl ester; 7β-(4-pyridylthio)-acetylamino-cepham-3-one-4ξ-carboxylic acid diphenylmethyl ester; 7β-(4-aminopyridinium-acetylamino)-cepham-3-one-4ξ-carboxylic acid diphenylmethyl ester and 7β-[D-α-(2,2,2-trichloroethoxycarbonyloxy)-α-phenyl-acetylamino]-cepham-3-one-4ξ-carboxylic acid diphenylmethyl ester.

The compounds which can be manufactured according to the invention can be converted further, for example as follows:

EXAMPLE 19

A solution of 0.050 g of 7β-phenylacetylamino-cepham-3-one-4ξ-carboxylic acid diphenylmethyl ester and 0.020 g of 1-methyl-3-(4-methylphenyl)-triazene in 5 ml of benzene is boiled for 2 hours under reflux. After cooling, the mixture is evaporated under reduced pressure and the residue is purified by thin layer chromatography (silica gel; 1×20 cm; system: toluene/ethyl acetate, 3:1). The zone (Rf~0.18) which is visible under ultraviolet light ($\lambda=254\mu$) is eluted with acetone and 3-methoxy-7β-phenylacetylamino-3-cephem-4-carboxylic acid diphenylmethyl ester is obtained, ultraviolet absorption spectrum (in ethanol): $\lambda_{max}=264\mu$ ($\epsilon=6,300$); infrared absorption spectrum (in methylene chloride): Characteristic bands at 2.94μ, 5.63μ, 5.83μ, 5.94μ, 6.26μ and 6.68μ.

EXAMPLE 20

A solution of 0.50 g of the 4-methylphenylsulphonate of 7β-amino-cepham-3-one-4ξ-carboxylic acid diphenylmethyl ester, which is predominantly present in the enol form, that is to say as the 4-methylphenylsulphonate of 7β-amino-3-cephem-3-ol-4-carboxylic acid diphenylmethyl ester, in 25 ml of methanol, is treated, at 0° C. with a solution of diazomethane in diethyl ether until the yellow colouration persists. The mixture is stirred for 10 minutes in an ice bath and is then evaporated. The residue is chromatographed on silica gel. Oily 7β-amino-3-methoxy-3-cephem-4-carboxylic acid diphenylmethyl ester is eluted with a 2:1 mixture of toluene and ethyl acetate, thin layer chromatogram (silica gel; development with iodine vapour): Rf~0.39 (system: ethyl acetate); ultraviolet absorption spectrum (in ethanol): $\lambda_{max}=265\mu$ ($\epsilon=6,100$); infrared absorption spectrum (in methylene chloride): characteristic bands at 3.33μ, 5.63μ, 5.81μ and 6.23μ.

Further elution with ethyl acetate yields oily 7β-dimethylamino-3-methoxy-3-cephem-4-carboxylic acid diphenylmethyl ester, thin layer chromatogram (silica gel; development with iodine vapour): Rf~0.20 (system: ethyl acetate); ultraviolet absorption spectrum (in ethanol): $\lambda_{max}=265\mu$ ($\epsilon=5,900$); infrared absorption spectrum (in methylene chloride): characteristic bands at 2.98μ, 3.33μ, 5.62μ, 5.81μ and 6.24μ.

A solution, cooled to 0° C., of 0.253 g of D-α-tert.-butoxycarbonylamino-α-(1,4-cyclohexadienyl)-acetic acid in 75 ml of methylene chloride is stirred for 30 minutes with 0.097 ml of N-methyl-morpholine and 0.129 ml of chloroacetic acid isobutyl ester under a nitrogen atmosphere, the mixture is then cooled to −10° C. and 0.30 g of 7β-amino-3-methoxy-3-cephem-4-carboxylic acid diphenylmethyl ester and 0.085 g of N-methyl-morpholine are added successively. The reaction mixture is stirred for 30 minutes at −10° C. and for 30 minutes at 0° C., 30 ml of water are added and the pH value is adjusted to 7.9 by adding 40% strength aqueous dipotassium hydrogen phosphate solution. The phases are separated, the aqueous solution is extracted with methylene chloride and the combined organic solutions are washed with a saturated aqueous sodium chloride solution, dried over sodium sulphate and evaporated under reduced pressure. The residue is purified by means of preparative layer chromatography (silica gel; system: diethyl ether; identification with ultraviolet light, λ=254 mμ; Rf∼0.39). 7β-[D-α-tert.-Butoxycarbonylamino-α-(1,4-cyclohexadienyl)-acetylamino]-3-methoxy-3-cephem-4-carboxylic acid diphenylmethyl ester, which is pure according to thin layer chromatography, is obtained as an amorphous product, thin layer chromatogram (silica gel; identification with diethyl ether): Rf∼0.39 (system: diethyl ether); $[\alpha]_D^{20}$=+1°±1° (c=0.745 in chloroform); ultraviolet absorption spectrum (in 95% strength aqueous ethanol): $\lambda_{max}$=263 mμ (ε=6,700) and $\lambda_{shoulder}$=280 mμ (ε=6,300); infrared absorption spectrum (in methylene chloride): characteristic bands at 2.96μ, 5.64μ, 5.86μ, 5.90μ (shoulder) 6.27μ and 6.73μ.

A mixture of 0.200 g of 7β-[D-α-tert.-butoxycarbonylamino-α-(1,4-cyclohexadienyl)-acetylamino]-3-methoxy-3-cephem-4-carboxylic acid diphenylmethyl ester, 0.5 ml of anisole and 10 ml of pre-cooled trifluoroacetic acid is stirred for 15 minutes at 0° C. and subsequently mixed with 50 ml of cold toluene and evaporated under reduced pressure. The residue is stirred with diethyl ether and the pulverulent precipitate is filtered off and dried. The salt, thus obtained, of 7β-[D-α-amino-α-(1,4-cyclohexadienyl)-acetylamino]-3-methoxy-3-cephem-4-carboxylic acid with trifluoroacetic acid is dissolved in about 6 ml of water, the pH value of the solution is adjusted to 1.5 by adding 2N hydrochloric acid, the aqueous solution is washed with 20 ml of ethyl acetate and its pH value is adjusted to 5.0 by dropwise addition of a 20% strength solution of triethylamine in methanol. It is diluted with 20 ml of acetone and 10 ml of diethyl ether and the mixture is left to stand for 16 hours at 0° C. The resulting precipitate is filtered off, washed with acetone and diethyl ether and dried. 7β-[D-α-amino-α-(1,4-cyclohexadienyl)-acetylamino]-3-methoxy-3-cephem-4-carboxylic acid is thus obtained in the form of the internal salt, melting point 170° C. (with decomposition); thin layer chromatogram (silica gel; identification with iodine): Rf∼0.26 (system: n-butanol/acetic acid/water, 67:10:23) and Rf∼0.58 (system:isopropanol/formic acid/water, 77:4:19); ultraviolet absorption spectrum: $\lambda_{max}$=267 mμ (ε=6,100) in 0.1N hydrochloric acid, and $\lambda_{max}$=268 mμ (ε=6,600) in 0.1N aqueous sodium bicarbonate solution.

EXAMPLE 21

A mixture of 250 ml of anisole in 1,200 ml of methylene chloride is added to 256.3 g of 3-methoxy-7β-(D-α-tert.-butoxycarbonylamino-α-phenyl-acetylamino)-3-cephem-4-carboxylic acid diphenylmethyl ester and the whole is treated, at 0° C., with 1,200 ml of trifluoroacetic acid which has been precooled to 0° C. The reaction mixture is left to stand for 30 minutes at 0° C. and is diluted, over the course of 15 minutes, with 12,000 ml of a 1:1 mixture of diethyl ether and petroleum ether which has been cooled to 0° C. The trifluoroacetic acid salt of 3-methoxy-7β-(D-α-phenyl-glycylamino)-3-cephem-4-carboxylic acid which has precipitated is filtered off, washed with diethyl ether, dried under reduced pressure and dissolved in 1,900 ml of water. To remove the yellowish-coloured impurities, the solution is washed with 900 ml of ethyl acetate; the organic wash liquid is discarded and the aqueous solution (pH∼1.5) is adjusted to pH 4.5 with a 20% strength solution of triethylamine in methanol. The internal salt of 3-methoxy-7β-(D-α-phenyl-glycylamino)-3-cephem-4-carboxylic acid crystallises out as the dihydrate, in the form of colourless prisms, and is filtered off after having been mixed with 1,800 ml of acetone and stirred for 2 hours at 0° C.; melting point 175°–177° C. (with decomposition); $[\alpha]_D^{20}$=+138°±1° (c=1 in 0.1N hydrochloric acid); ultraviolet absorption spectrum (in 0.1N aqueous sodium bicarbonate solution): $\lambda_{max}$=265 mμ (ε=6,500); infrared absorption spectrum (in mineral oil): Bands at 2.72μ, 2.87μ, 3.14μ, 3.65μ, 5.68μ, 5.90μ, 6.18μ, 6.27μ, 6.37μ, 6.56μ, 6.92μ, 7.16μ, 7.58μ, 7.74μ, 7.80μ, 8.12μ, 8.30μ, 8.43μ, 8.52μ, 8.65μ, 8.95μ, 9.36μ, 9.55μ, 9.70μ, 10.02μ, 10.38μ, 10.77μ, 11.70μ, 12.01μ, 12.15μ, 12.48μ, 12.60μ, 12.87μ, 13.45μ and 14.30μ; microanalysis ($C_{16}H_{17}O_5N_3S \cdot 2H_2O$; molecular weight: 399.42): Calculated: C 48.11%, H 5.30%, N 10.52% and S 8.03%; found: C 47.86%, H 5.27%, N 10.47% and S 8.00%.

EXAMPLE 22

A mixture of 0.06 g of 3-methoxy-7β-phenylacetylamino-3-cephem-4-carboxylic acid diphenylmethyl ester and 0.05 ml of anisole and 1 ml of trifluoroacetic acid is left to stand for 5 minutes at room temperature and is then evaporated under reduced pressure. The residue is twice evaporated to dryness together with a 1:1 mixture of chloroform and toluene and is chromatographed on 5 g of silica gel (containing about 5% of water). The amorphous 3-methoxy-7β-phenylacetylamino-3-cephem-4-carboxylic acid is eluted with methylene chloride containing 30–50% of acetone and is lyophilised from dioxane. Ultraviolet absorption spectrum (in 95% strength aqueous ethanol): $\lambda_{max}$=259 mμ (ε=4,970) and 265 mμ (ε=4,950); infrared absorption spectrum (in methylene chloride): characteristic bands at 3.03μ, 5.60μ, 5.74μ, 5.92μ, 6.24μ and 6.67μ.

EXAMPLE 23

A mixture of 0.312 g of 3ξ-hydroxy-7β-phenylacetylamino-cepham-4ξ-carboxylic acid diphenylmethyl ester in 15 ml of pyridine and 7 ml of acetic anhydride is left to stand for 16 hours at 0° C. and after addition of 50 ml of toluene is evaporated under reduced pressure. The residue is taken up in ethyl acetate; the organic solution is washed with a saturated aqueous sodium bicarbonate solution and a saturated aqueous sodium chloride solution, dried over sodium sulphate and evaporated under reduced pressure. The residue is purified by means of preparative thin layer chromatography; a silica gel plate of 100 cm length is used and development is carried out with a 1:1 mixture of toluene and ethyl acetate. 3ξ-Acetoxy-7β-phenylacetylaminocepham-4α-carboxylic acid diphenylmethyl ester of Rf=0.47 is obtained, melting at 162°–164° C. after crystallization from a mixture of methylene chloride and pentane; $[\alpha]_D^{20}$=+55°±1° (c=0.492 in chloroform); ultraviolet absorption spectrum (in 95% strength ethanol): $\lambda_{max}$=253 mμ (ε=700), 258 mμ(ε=820) and 265 mμ (ε=660); infrared absorption spectrum (in methylene chloride): characteristic bands at 2.96μ, 5.66μ, 5.77μ, 5.97μ, 6.28μ and 6.71μ.

A mixture of 0.150 g of 3ξ-acetoxy-7β-phenylacetylamino-cepham-4ξ-carboxylic acid diphenylmethyl ester and 5 ml of methylene chloride is treated with 0.1 ml of triethylamine and left to stand for 16 hours at room temperature. The reaction mixture is diluted with 100 ml of methylene chloride; the organic phase is washed with 50 ml of 2N hydrochloric acid and 50 ml of a saturated aqueous sodium chloride solution, dried over magnesium sulphate and evaporated under reduced pressure. The residue is purified by means of preparative thin layer chromatography (2 silica gel plates of 20 cm length, system: toluene/ethyl acetate, 3:1). At Rf=0.36, a pale yellowish oil is obtained, which crystallises from a mixture of methylene chloride and hexane. The product is 7β-phenylacetylamino-3-cephem-4-carboxylic acid diphenylmethyl ester, melting point 161°-163° C., $[\alpha]_D^{20} = +30° \pm 1°$ (c=0.968 in dioxane); thin layer chromatogram (silica gel; identification in ultraviolet light and by means of iodine vapour): Rf=0.55 (system: toluene/acetone, 4:1), Rf=0.35 (system: toluene/actone, 9:1) and Rf=0.40 (system: toluene/ethyl acetate, 4:1): ultraviolet absorption spectrum: $\lambda_{max}=258$ mμ ($\epsilon=6,100$) and $\lambda_{min}=240$ mμ ($\epsilon=5,250$) (in methylene chloride) and $\lambda_{max}=259$ mμ ($\epsilon=6,050$) and $\lambda_{min}=239$ mμ ($\epsilon=4,950$) (in 95% strength aqueous ethanol); infrared absorption spectrum: characteristic bands at 2.90μ, 5.57μ, 5.76μ, 5.91μ, 6.09μ, 6.66μ, 7.13μ, 8.12μ, 8.63μ, 9.07μ, 10.43μ and 12.22μ (in methylene chloride) and 3.01μ, 5.60μ, 5.82μ, 6.04μ, 6.08μ (shoulder), 6.51μ and 7.13μ (in mineral oil).

A solution of 1.94 g of 7β-phenylacetylamino-3-cephem-4-carboxylic acid diphenylmethyl ester in 100 ml of absolute methylene chloride is cooled to −15° C., 3.86 ml of absolute pyridine and 31.6 ml of an 8% strength solution of phosphorus pentachloride in methylene chloride are then added and the reaction mixture is stirred for 30 minutes at −10° C. and for a further 30 minutes at −5° C. The golden yellow solution is cooled to −20° C. and 26.8 ml of absolute methanol are added at a speed such that the internal temperature does not rise above −10° C. The reaction mixture is stirred for one hour at −10° C. and left to stand for a further hour at 25°-30° C., and is then mixed with 80 ml of an 0.5 molar aqueous potassium dihydrogen phosphate solution, whilst stirring vigorously. The pH value of the two-phase reaction mixture is adjusted to 2 by dropwise addition of 20% strength phosphoric acid, the mixture is stirred for 20 minutes at room temperature and the phases are separated. The aqueous solution is twice washed with methylene chloride; the combined organic solutions are washed with two portions of water, each of 20 ml, and are dried over anhydrous magnesium sulphate.

The solvent is removed under reduced pressure; the oily residue is applied to a column of 110 g of silica gel (5% water content). The elution with methylene chloride, phenylacetic acid methyl ester and methylene chloride containing 3% of methyl acetate yields 7β-amino-3-cephem-4-carboxylic acid diphenylmethyl ester, which is crystallised by dissolving in a small amount of methylene chloride and adding diethyl ether to the warm solution (giving needle-shaped crystals), and is washed with cold diethyl ether and dried, melting point 153°-154° C.; thin layer chromatogram (silica gel): Rf=0.50 (system: toluene/acetone, 4:1), Rf=0.65 (system: toluene/acetone, 2:1), Rf=0.40 (system: toluene/ethyl acetate, 1:1) and Rf=0.33 (system: toluene/diethyl ether, 1:1); ultraviolet absorption spectrum: $\lambda_{max}=257$ mμ ($\epsilon=8,150$) and $\lambda_{min}=245$ mμ ($\epsilon=7,730$) (in methylene chloride) and $\lambda_{max}=255$ mμ ($\epsilon=5,500$) and $\lambda_{min}=236$ mμ ($\epsilon=4,650$) (in 95% ethanol); infrared absorption spectrum: characteristic bands at 2.91μ, 2.97μ, 5.61μ, 5.78μ, 6.11μ, 7.14μ, 8.15μ, 8.29, 9.14μ and 9.83μ (in methylene chloride) and at 2.99μ, 5.65μ, 5.77μ, 6.08μ, 7.14μ, 7.74μ, 7.84μ, 8.08μ, 8.53μ, 9.14μ, 9.85μ and 10.35 (in mineral oil).

0.380 g of 7β-amino-3-cephem-4-carboxylic acid diphenylmethyl ester is covered with 2 ml of anisole and 8 ml of absolute trifluoroacetic acid, and the clear solution is left to stand for 10 minutes at room temperature and is then diluted with about 20 ml of absolute toluene. The mixture is evaporated under reduced pressure; the residue is twice evaporated to dryness after addition of toluene and is then suspended in 5 ml of methanol, 5 ml of diethyl ether and 0.5 ml of water. The pH value of the suspension is adjusted to 3.5 by dropwise addition of a 5% strength solution of triethylamine in methanol; the whole is left to stand for 30 minutes in an ice bath and the fine precipitate is filtered off with the aid of a suitable glass suction filter. The pale beige-coloured filter residue is washed with a mixture of methanol and methylene chloride and then with diethyl ether and is dried under reduced pressure at 35° C. The 7β-amino-3-cephem-4-carboxylic acid thus obtainable as a fine microcrystalline powder decomposes at 215° C.; thin layer chromatogram (silica gel; developing with iodine): Rf=0.12 (system: n-butanol/acetic acid/water, 67:10:23), Rf=0.28 (system: n-butanol/pyridine/acetic acid/water, 40:24:6:30) and Rf=0.21 (system: ethyl acetate/n-butanol/pyridine/acetic acid/water, 42:21:21:6:10); infrared absorption spectrum (in mineral oil): characteristic bands at 3.12μ, 3.80μ, 4.12μ (shoulder), 4.94μ, 5.54μ, 6.05μ (shoulder), 6.19μ, 6.55μ, 7.05μ, 7.42μ, 8.23μ, 8.79μ, 9.55μ, 12.08μ, 12.69μ, and 13.04μ.

A suspension of 0.070 g of 7β-amino-3-cephem-4-carboxylic acid in 2 ml of absolute methylene chloride is treated with 0.031 g of triethylamine in 0.35 ml of methylene chloride, the suspension is diluted with 5 ml of absolute tetrahydrofurane and the mixture is stirred for 30 minutes, periodically in an ultrasonics bath.

0.102 g of tert.-butoxycarbonyl-D-α-phenylglycine is dissolved in 5 ml of absolute methylene chloride, 0.040 g of 4-methylmorpholine is added and the mixture is diluted with 10 ml of acetonitrile. It is cooled to −20° C. and 0.060 g of chloroformic acid isobutyl ester is added whilst stirring, after which the reaction is allowed to proceed for 30 minutes at −15° C. After again cooling to below −20° C., the milky suspension of the triethylammonium salt of 7β-amino-3-cephem-4-carboxylic acid is then added. The reaction mixture is stirred for 30 minutes at −15° C., a further 30 minutes at 0° C. and finally 2 hours at room temperature. It is filtered, the residue is rinsed with acetonitrile, methylene chloride and diethyl ether, and the filtrate is dried and evaporated to dryness. The residue is taken up in ethyl acetate and water and the mixture is acidified to pH 2 by adding 5 molar aqueous phosphoric acid whilst stirring vigorously and cooling with ice. The organic phase is separated off and washed four times with a small amount of a saturated aqueous sodium chloride solution. The aqueous extracts are re-extracted with 2 portions of ethyl acetate and the combined organic extracts are dried over anhydrous magnesium sulphate and freed of the solvent under reduced pressure. The residue is chromatographed on 10 g of silica gel (column; 5% water added). First, unreacted tert.-butoxycarbonyl-D-α-phenylglycine is eluted with methylene chloride and with methylene chloride containing increasing proportions of acetone, and subsequently 7β-(D-α-tert.-butoxycarbonylamino-α-phenyl-acetylamino)-3-cephem-4-carboxylic acid is eluted and obtained in an amorphous form; ultraviolet absorption spectrum (in 95% strength ethanol): $\lambda_{max}=252$ mμ ($\epsilon=5,100$); infrared absorption spectrum (in methylene chloride): characteristic bands at 5.61μ, 5.85μ, 5.92μ and 6.12μ; thin layer chromatogram (silica gel G; detection with iodine vapour): Rf=0.6–0.7 (system: n-butanol/acetic acid/water, 44:12:44).

A solution of 0.02 g of 7β-(D-α-tert.-butoxycarbonylamino-α-phenyl-acetylamino)-3-cephem-4-carboxylic acid in 3 ml of pure trifluoroacetic acid is left to stand for 15 minutes at room temperature. The resulting solution is evaporated in a rotary evaporator and the residue is twice evaporated to dryness with addition of 20 ml of a 1:1 mixture of chloroform and toluene, in order to remove the trifluoroacetic acid completely, and is dried for 16 hours at 0.0001 mm Hg. 7β-(D-α-Phenylglycyl)-amino]-3-cephem-4-carboxylic acid is obtained as a yellowish amorphous powder, by adding an equivalent amount of triethylamine to a solution of the resulting salt with trifluoroacetic acid, in water and methanol, evaporating and digesting the residue with methylene chloride. Thin layer chromatogram (silica gel; developing with iodine vapour): Rf=0.29 (system: n-butanol/pyridine/acetic acid/water, 40:24:6:30); ultraviolet absorption spectrum (in water): $\lambda_{max}=250$ mμ ($\epsilon=4,300$).

EXAMPLE 24

A mixture of 0.5 g of 3-n-butoxy-7β-(D-α-tert.-butoxycarbonylamino-α-phenylacetylamino)-3-cephem-4-carboxylic acid diphenylmethyl ester, 1 ml of anisole and 15 ml of trifluoroacetic acid is left to stand for 15 minutes at 0° C. and is then diluted with 200 ml of cold toluene and evaporated under reduced pressure. The residue is stirred with diethyl ether and the pulverulent colourless residue is filtered off, washed with diethyl ether and dried under a high vacuum. The trifluoroacetate salt of 3-n-butoxy-7β-(D-α-phenyl-glycylamino)-3-cephem-4-carboxylic acid is thus obtained, and is dissolved in 5 ml of water. The solution is twice washed with 10 ml of ethyl acetate at a time and the pH value of the aqueous phase is adjusted to 5.0 by adding a solution of triethylamine in methanol. Thereafter the solution is evaporated under reduced pressure; the residue is taken up in a small amount of acetone and is diluted with diethyl ether until the mixture is turbid. The 3-n-butoxy-7β-(D-α-phenyl-glycylamino)-3-cephem-4-carboxylic acid, which is present in the form of the internal salt, is obtained as a crystalline precipitate and filtered off, melting point 141°–142° C.; thin layer chromatogram (silica gel): Rf∼0.21 (system: ethyl acetate/pyridine/acetic acid/water, 62:21:6:11); ultraviolet absorption spectrum (in 0.1N aqueous sodium bicarbonate solution): $\lambda_{max}=267$ mμ ($\epsilon=7,300$).

EXAMPLE 25

A mixture of 2.70 g of 3-ethoxy-7β-(D-α-tert.-butoxycarbonylamino-α-phenylacetylamino)-3-cephem-4-carboxylic acid diphenylmethyl ester, 6.7 ml of anisole and 67 ml of formic acid is stirred for one hour at room temperature, diluted with 200 ml of toluene and then evaporated under reduced pressure, and the residue is dried under a high vacuum, digested with diethyl ether and filtered off. The formate of 3-ethoxy-7β-(D-α-phenyl-glycylamino)-3-cephem-4-carboxylic acid, which is obtained as a brownish powder, is dissolved in 8 ml of water and the aqueous phase is acidified with 2N aqueous hydrochloric acid, washed with 10 ml of ethyl acetate, adjusted to a pH value of about 5 with a 10% strength solution of triethylamine in methanol and evaporated under reduced pressure. The residue is taken up in a small amount of methanol and the amorphous light yellowish 3-ethoxy-7β-(D-α-phenyl-glycylamino)-3-cephem-4-carboxylic acid is precipitated as the internal salt by addition of methylene chloride and diethyl ether; thin layer chromatogram (silica gel): Rf∼0.17 (system: ethyl acetate/pyridine/acetic acid/water, 62:21:6:11); ultraviolet absorption spectrum (in 0.1 molar aqueous sodium bicarbonate solution): $\lambda=263$ mμ ($\epsilon=5,500$).

EXAMPLE 26

A mixture of 4.6 g of 3-benzyloxy-7β-(D-α-tert.butoxycarbonylamino-α-phenylacetylamino)-3-cephem-4-carboxylic acid diphenylmethyl ester, 10 ml of anisole and 100 ml of trifluoroacetic acid is stirred for 15 minutes at 0° C., then diluted with 250 ml of pre-cooled toluene and evaporated under reduced pressure, and the residue is dried in a high vacuum. The product is stirred with diethyl ether and the pulverulent trifluoroacetate of 3-benzyloxy-7β-(D-α-phenyl-glycylamino)-3-cephem-4-carboxylic acid is thus obtained; this is filtered off and dissolved in a 9:1 mixture of water and methanol. The pH value is adjusted to 1.7 with 2N aqueous hydrochloric acid; the mixture is twice washed with 30 ml of ethyl acetate at a time (the organic wash solutions are discarded) and the pH value of the aqueous phase is adjusted to 5 by addition of a 10% strength solution of triethylamine in methanol. The aqueous phase is evaporated under reduced pressure, the residue is stirred with a mixture of acetone and diethyl ether, and the pulverulent product is filtered off and rinsed with acetone and with diethyl ether. 3-Benzyloxy-7β-(D-α-phenyl-glycylamino)-3-cephem-4-carboxylic acid is thus obtained in the form of a zwitter-ion, thin layer chromatogram (silica gel): Rf=0.17 system: ethyl acetate/pyridine/acetic acid/water, 62:21:6:11); ultraviolet absorption spectrum (in 0.1N aqueous sodium bicarbonate solution): $\lambda_{max}=266$ mμ ($\epsilon=6,500$).

EXAMPLE 27

A solution of 0.263 g of 7β-(5-benzoylamino-5-diphenylmethoxycarbonyl-valeryl-amino)-3-methoxy-3-cepham-4-carboxylic acid diphenylmethyl ester in 13 ml of methylene chloride is cooled to −10° C. and 0.132 ml of pyridine and 3.52 ml of an 8% strength solution of phosphorus pentachloride in methylene chloride are added. The mixture is stirred for one hour at −10° C. and is then cooled to −30° C., 2.2 ml of methanol cooled to −30° C. are added rapidly and the whole is stirred further for 30 minutes at −10° C. and 30 minutes at −5° C. Thereafter, 6.5 ml of an 0.5 molar aqueous solution of potassium dihydrogen phosphate are added to the reaction mixture, which is stirred for 5 minutes at room temperature, and the phases are separated. The aqueous phase is washed with methylene chloride; the combined methylene chloride phases are washed with concentrated aqueous sodium chloride solution, dried over sodium sulphate and evaporated under reduced pressure. The residue is dissolved in methanol and the solution is treated with diethyl ether until it is slightly turbid. 7β-Amino-3-methoxy-3-cephem-4-carboxylic acid diphenylmethyl ester is thus obtained as an amorphous precipitate, thin layer chromatogram (silica gel): Rf=0.17 (system: ethyl acetate; development with iodine): ultraviolet absorption spectrum (in 95% strength aqueous ethanol): λ$_{max}$=258 mμ (ε=5,700); infrared absorption spectrum (in dioxane): characteristic bands at 2.87μ, 5.62μ, 5.85μ and 6.26μ.

EXAMPLE 28

A solution, cooled to 0° C., of 0.63 g of 3-methoxy-7β-(D-α-tert.-butoxycarbonylamino-α-phenyl-acetylamino)-2-cephem-4α-carboxylic acid diphenylmethyl ester in 25 ml of methylene chloride is treated with a solution of 0.20 g of 3-chloroperbenzoic acid in 5 ml of methylene chloride. The mixture is stirred for 30 minutes at 0° C., 50 ml of methylene chloride are added and the whole is washed successively with 25 ml of a saturated aqueous sodium bicarbonate solution and a saturated aqueous sodium chloride solution. The organic phase is dried over sodium sulphate and evaporated under reduced pressure. The residue is crystallised from a mixture of methylene chloride and diethyl ether; 3-methoxy-7β-(D-α-tert.-butoxycarbonylamino-α-phenyl-acetyl-amino)-3-cephem-4-carboxylic acid diphenylmethyl ester-1-oxide is thus obtained in the form of colourless needles, melting point 172°-175° C.; thin layer chromatogram (silica gel): Rf~0.44 (system: ethyl acetate; developing with iodine vapour); ultraviolet absorption spectrum (in ethanol): λ$_{max}$=277 mμ (ε=7,200); infrared absorption spectrum (in methylene chloride): characteristic bands at 2.96μ, 5.56μ, 5.71μ, 5.83μ, 5.90μ, 6.27μ and 6.67μ.

A solution, cooled to −10° C., of 1.30 g of 3-methoxy-7β-(D-α-tert.-butoxycarbonylamino-α-phenyl-acetyl-amino)-3-cephem-4-carboxylic acid diphenylmethyl ester-1-oxide in 30 ml of dimethylformamide is treated with 2.80 g of phosphorus trichloride whilst excluding air. After standing for 15 minutes, the reaction mixture is poured out onto a mixture of ice and an aqueous dipotassium hydrogen phosphate solution; the aqueous mixture is twice extracted with 100 ml of ethyl acetate at a time. The organic extract is washed with a saturated aqueous sodium chloride solution, dried over sodium sulphate and evaporated. The residue is chromatographed on silica gel; amorphous 3-methoxy-7β-(D-α-tert.-butoxycarbonylamino-α-phenyl-acetyl-amino)-3-cephem-4-carboxylic acid diphenylmethyl ester is eluted, with diethyl ether, as a substance which is pure according to thin layer chromatography, Rf~0.39 (system: diethyl ether; developing with iodine vapour); [α]$_D$=1°±1° (c=0.981 in chloroform); ultraviolet absorption spectrum (in ethanol): λ$_{max}$=264μ (ε=6,300); infrared absorption spectrum (in methylene chloride): characteristic bands at 2.94μ, 5.62μ, 5.84μ, 5.88μ, 6.25μ amd 6.70μ.

We claim:

1. A 7β-amino-cepham-3-one-4-carboxylic acid compound of the formula

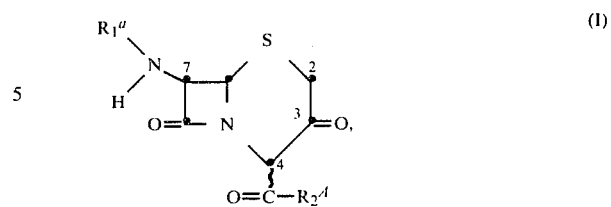

a 1-oxide thereof, a 1-oxide of the 3-hydroxy-3-cephem form thereof, or a salt of such compound, wherein $R_1{}^a$ represents a group of the formula

wherein $R^I$ represents cycloalkyl with 5–7 ring carbon atoms which is substituted in the 1-position by amino, protected amino, sulphoamino, or by sulphoamino in the salt-form, or $R^I$ represents phenyl, naphthyl or tetrahydronaphthyl or phenyl, naphthyl or tetrahydronaphthyl substituted by hydroxyl, protected hydroxyl, lower alkoxy, and/or by halogen, or $R_1{}^a$ represents a group of the formula

wherein $R^I$ represents phenyl, hydroxyphenyl, protected hydroxyphenyl, halogeno-phenyl, hydroxy-halogeno-phenyl, protected hydroxy-halogeno-phenyl, amino-lower alkyl-phenyl, protected amino-lower alkyl-phenyl, phenyloxyphenyl or $R_1{}^a$ represents a group of the formula

wherein $R^I$ represents phenyl, hydroxyphenyl, protected hydroxyphenyl, halogeno-phenyl, hydroxy-halogeno-phenyl, protected hydroxy-halogeno-phenyl, and $R^{II}$ represents amino, protected amino, guanidinocarbonylamino, sulphoamino, sulphoamino in salt-form, azido, carboxyl, carboxyl in salt-form, lower alkoxycarbonyl, diphenylmethoxycarbonyl, cyano, sulpho, hydroxyl, protected hydroxyl, O-lower, alkyl-phosphone, O,O'-di-lower alkyl-phosphone or halogeno, whereby $R^I$ can also be 1,4-cyclohexadienyl, if $R^{II}$ represents carboxyl, carboxyl in salt-form, lower alkoxycarbonyl, diphenylmethoxycarbonyl, cyano, sulpho, hydroxyl, protected hydroxyl, O-lower alkyl-phosphone, O,O'-di-lower alkyl-phosphone or halogeno, or $R_1{}^a$ represents a group of the formula

wherein $R^1$ represents phenyl, hydroxyphenyl, protected hydroxyphenyl, hydroxy-halogeno-phenyl, protected hydroxy-halogeno-phenyl, or 1,4-cyclohexadienyl and $R^{II}$ represents aminomethyl or protected aminomethyl, and $R_2{}^A$ represents a radical which together with the carbonyl grouping —C(=O)— forms a protected carbonyl group, except that there are excluded the compounds of the formula

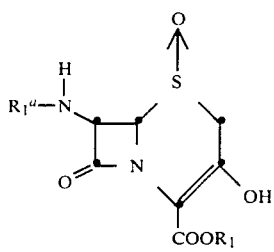

wherein $R_1{}^a$ is phenylacetyl and $R_1$ is a carboxylic acid protecting ester forming group, and the compounds in the keto form of the formula

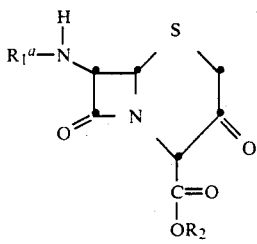

wherein $R_1{}^a$ is an acyl group of the formula

 (A₁)

wherein
$R^I$ is phenyl or phenyl substituted by halogen or hydroxy, or
$R_1{}^a$ is a group of the formula

 (A₂)

wherein $R^I$ is phenyl, hydroxyphenyl or halogenophenyl, or $R_1{}^a$ is a group of the formula

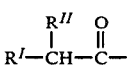 (A₃)

wherein $R^I$ is phenyl, hydroxyphenyl, halogenophenyl or 1,4-cyclohexadienyl, and $R^{II}$ is hydroxy or protected hydroxy and wherein $R_2$ is a carboxylic acid protecting ester forming group.

2. A 7β-amino-cepham-3-one-4-carboxylic acid compound according to claim 1, a 1-oxide thereof or a 1-oxide of the 3-hydroxy-3-cephem form thereof, wherein $R_1{}^a$ represent a group of the formula

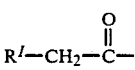 (A₂)

wherein $R^I$ represents phenyl, hydroxyphenyl protected hydroxyphenyl, chloro-phenyl, hydroxy-chlorophenyl, protected hydroxy-chloro-phenyl, or $R_1{}^a$ represents a group of the formula

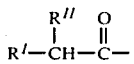 (A₃)

wherein $R^I$ represents phenyl, hydroxyphenyl, protected hydroxyphenyl, halogeno-phenyl, hydroxy-halogeno-phenyl, protected hydroxy-halogeno-phenyl, and $R^{II}$ represents amino, protected amino, guanidinocarbonylamino, sulphoamino, sulphoamino in salt-form, carboxyl, carboxyl in salt-form, lower alkoxycarbonyl, diphenylmethoxycarbonyl, sulpho, hydroxyl, formyloxy, lower alkoxycarbonyloxy, 2-halogeno-lower alkoxy-carbonyloxy, mono- or diphenyl-lower alkoxycarbonyloxy, methoxy-phenyl-lower alkoxycarbonyloxy, nitrophenyl-lower-alkoxycarbonyloxy, O-lower alkylphosphono, or O,O'-di-lower alkyl-phosphono, whereby $R^I$ can also be 1,4-cyclohexadienyl, if $R^{II}$ represents carboxyl, carboxyl in salt-form, lower alkoxycarbonyl, diphenylmethoxycarbonyl, sulpho, hydroxyl, formyloxy, lower alkoxycarbonyloxy, 2-halogeno-lower alkoxycarbonyloxy, mono- or diphenyl-lower alkoxycarbonyloxy, methoxy-phenyl-lower alkoxycarbonyloxy, nitrophenyl-lower alkoxycarbonyloxy, O-lower alkyl-phosphono, or O,O'-di-lower alkyl-phosphono, and $R_2{}^A$ represents a radical which together with the carbonyl grouping —C(=O)— forms a protected carboxyl group, except that there are excluded the compounds of the formula

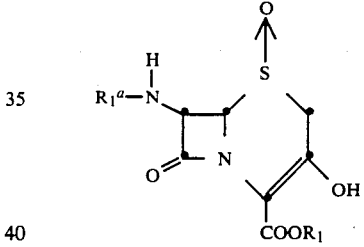

wherein $R_1{}^a$ is phenylacetyl and $R_1$ is a carboxylic acid protecting ester forming group and the compounds in the keto form of the formula

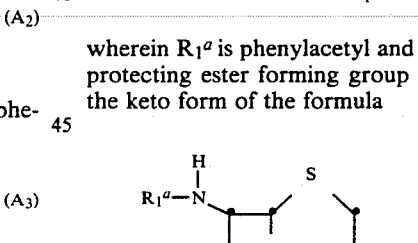

wherein $R_1{}^a$ is an acyl group of formula or

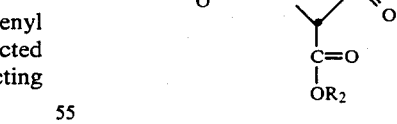 (A₂)

wherein $R^I$ is phenyl, hydroxyphenyl or halogenophenyl, or $R_1{}^a$ is a group of the formula

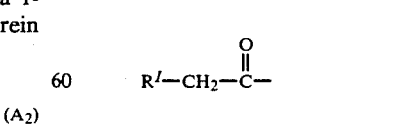 (A₃)

wherein R^I is phenyl, hydroxyphenyl, halogenophenyl or 1,4-cyclohexadienyl, and R^II is hydroxy, formyloxy, lower alkoxycarbonyloxy, 2-halogeno-lower alkoxycarbonyloxy, mono- or diphenyl-lower alkoxycarbonyloxy, methoxy-phenyl-lower alkoxycarbonyloxy, nitrophenyl-lower alkoxycarbonyloxy and wherein $R_2$ is a carboxylic acid protecting ester forming group.

3. A 7β-amino-cepham-3-one-4-carboxylic acid compound according to claim 1, a 1-oxide thereof or a 1-oxide of the 3-hydroxy-3-cephem form thereof wherein $R_1{}^a$ represents a group of the formula

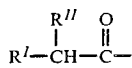  (A₃)

wherein $R^1$ represents phenyl, 4-hydroxyphenyl, lower alkoxycarbonyloxyphenyl, or 2-halogeno-lower alkoxycarbonyloxyphenyl, and $R^{II}$ is amino, lower alkoxycarbonylamino, 2-halogeno-lower alkoxycarbonylamino, mono- or diphenyl-lower alkoxycarbonylamino, lower alkoxyphenyl-lower alkoxycarbonylamino, nitrophenyl-lower alkoxycarbonylamino, or 2-halogeno-ethoxycarbonyloxy, and $R_2{}^A$ is diphenylmethoxy, p-nitrobenzyloxy or 2,2,2-trichloroethoxy, except that there are excluded the compounds in the keto form of the formula

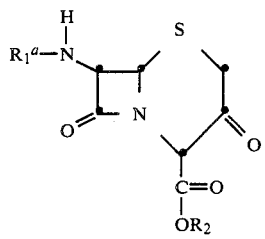

wherein $R_1{}^a$ is an acyl group of the formula

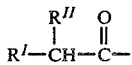  (A₃)

wherein $R^I$ is phenyl, or 4-hydroxyphenyl and $R^{II}$ is 2-halogenoethoxycarbonyloxy, and wherein $R_2$ is a carboxylic acid protecting ester forming group.

4. A compound of the formula

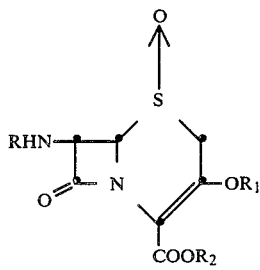

wherein R is an acyl group of the formula

wherein R' is (a) $C_1$-$C_7$-alkyl, $C_3$-$C_7$-alkenyl, cyanomethyl, halomethyl, 4-amino-4-carboxybutyl, 4-protected amino-4-carboxybutyl; or (b) the group R'' wherein R'' is 1,4-cyclohexadienyl, phenyl or phenyl substituted by halogen, hydroxy, amino or $C_1$-$C_4$-lower alkoxy;

(c) an aralkyl group of the formula R''—(Y)_m—$CH_2$— wherein R'' is defined as above, Y is O or S, m is 0 or 1 or (d) a substituted aralkyl group of the formula

wherein R''' is R'' as defined above, 2-thienyl or 3-thienyl, Z is hydroxy or protected hydroxy; or (e) a heteroarylmethyl group of the formula

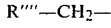

wherein R'''' is 2-thienyl, 3-thienyl, 2-furyl, 3-furyl or 1-tetrazyl; and wherein $R_1$ is hydrogen;

$R_2$ is a carboxylic acid protecting ester forming group, except that there are excluded 3-hydroxy-3-cephem-1-oxide compounds in which R is phenylacetyl or phenoxyacetyl.

5. Process for the manufacture of a 7β-amino-cepham-3-one-4-carboxylic acid compound of the formula

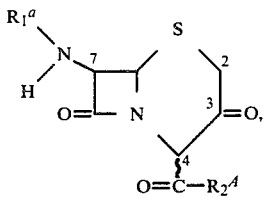  (I)

a 1-oxide thereof or a 1-oxide of the 3-hydroxy-3-cephem form thereof, wherein $R_1{}^a$ represents a group of the formula

  (A₁)

wherein $R^I$ represents cycloalkyl with 5–7 ring carbon atoms which is substituted in the 1-position by amino, protected amino, sulphoamino, or by sulphoamino in the salt-form, or $R^I$ represents phenyl, naphthyl or tetrahydronaphthyl or phenyl, naphthyl or tetrahydronaphthyl substituted by hydroxyl, protected hydroxyl, lower alkoxy, and/or by halogen, or $R_1{}^a$ represents a group of the formula

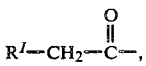  (A₂)

wherein $R^I$ represents phenyl, hydroxyphenyl, protected hydroxyphenyl, halogeno-phenyl, hydroxy-halogeno-phenyl, protected hydroxy-halogeno-phenyl, amino-lower alkyl-phenyl, protected amino-lower alkyl-phenyl or phenyloxyphenyl, or $R_1{}^a$ represents a group of the formula

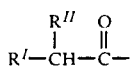 (A₃)

wherein $R^I$ represents phenyl, hydroxyphenyl, protected hydroxyphenyl, halogeno-phenyl, hydroxy-halogeno-phenyl, or protected hydroxy-halogeno-phenyl and $R^{II}$ represents amino, protected amino, guanidinocarbonylamino, sulphoamino, sulphoamino in salt-form, azido, carboxyl, carboxyl in salt-form, lower alkoxycarbonyl, diphenylmethoxycarbonyl, cyano, sulpho, hydroxyl, protected hydroxyl, O-lower alkylphosphono, O,O'-di-lower alkyl-phosphono or halogeno, or $R_1{}^a$ represents a group of the formula

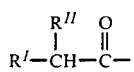 (A₅)

wherein $R^I$ represents phenyl, hydroxyphenyl, protected hydroxyphenyl, halogeno-phenyl, hydroxy-halogeno-phenyl or protected hydroxy-halogeno-phenyl and $R^{II}$ represents aminomethyl or protected aminomethyl and $R_2{}^A$ represents a radical which together with the carbonyl grouping —C(=O)— forms a protected carboxyl group, or a salt of such a compound, characterised in that a cephem compound of the formula

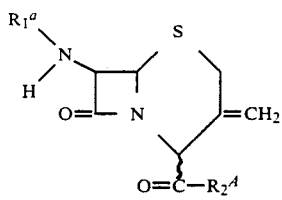 (II)

wherein $R_1{}^a$ has the meanings given under formula I, a 1-oxide or a salt thereof, is treated with ozone and the resulting ozonide is split by reduction and the compound of the formula I, a 1-oxide thereof, a 1-oxide of the 3-hydroxy-3-cephem form thereof, or a salt of such a compound is separated.

6. Process according to claim 5, characterised in that a compound of the formula II, a 1-oxide, or a salt thereof is treated in a solvent at a temperature between −90° and +40° C. with ozon and that the resulting ozonide is split under the same conditions of its formation by treatment with a reducing agent selected from the group consisting of hydrogen catalytically activated by a nickel or a palladium catalyst, zinc or zinc amalgam in the presence of a hydrogen donating acid or a lower alkanol, an alkali metall iodide in the presence of a hydrogen donating acid, formic acid, tetracyanoethylene, a di-lower alkyl-sulphide, a tri-lower alkyl-phosphine, triphenylphosphine, a tri-lower alkylphosphite, a hexa-lower alkylphosphorous acid triamide, and pyridine.

7. Process according to claim 6, characterised in that the resulting ozonide is split by treatment with tetracyanoethylene, dimethylsulfide, trimethylphosphide or pyridine.

8. The compound 7β-phenyl-acetylamino-3-hydroxy-3-cephem-4-[ξ]carboxylic acid diphenylmethyl ester 1-oxide.

9. The compound 7β-(D-α-tert.-butoxycarbonylamino-α-phenyl-acetylamino)-3-hydroxy-3-cephem-4-carboxylic acid diphenylmethyl ester 1-oxide.

10. The compound 7β-(D-α-tert.-butoxycarbonylamino-α-phenyl-acetylamino)-3-hydroxy-3-cephem-4-carboxylic acid p-nitrobenzyl ester 1-oxide.

11. The compound 7β-(D-α-tert.-butoxycarbonylamino-α-phenyl-acetylamino)-3-hydroxy-3-cephem-4-carboxylic acid 2,2,2-trichloroethyl ester 1-oxide.

12. A compound of the formula

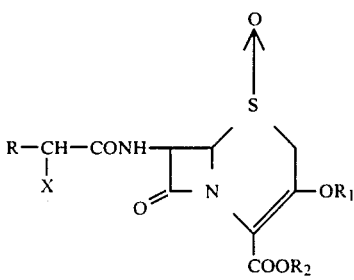

wherein
X is a protected amino group or free amino group
R is phenyl, hydroxyphenyl, halophenyl, 2-thienyl or 2-furyl
$R_1$ is hydrogen and
$R_2$ is a carboxylic acid protecting ester forming group.

13. The p-nitrobenzyl 7-(D-phenylglycylamido)-3-hydroxy-3-cephem-4-carboxylate 1-oxide.

14. The compound of claim 12, wherein the amino group of the 7-glycylamido substituent is protected with an amino protecting group selected from the group consisting of t-butoxy-carbonyl or 2,2,2-trichloroethoxycarbonyl.

15. The compound of claim 4, said compound being p-nitrobenzyl-7-phenylacetamido-3-hydroxy-3-cephem-4-carboxylate 1-oxide.

16. The compound of claim 4, said compound being p-methoxybenzyl 7-phenoxyacetamido-3-hydroxy-3-cephem-4-carboxylate 1-oxide.

17. The process for preparing a 3-hydroxy-3-cephem compound of the formula

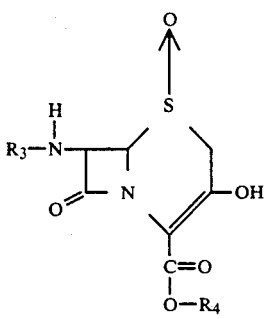

which comprises
(a) reacting with ozone in an inert solvent at a temperature between −90° and +40° C. a 3-exomethylenecepham compound of the formula

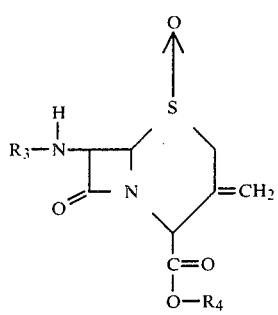

to obtain the intermediate ozonide;

(b) adding to the reaction mixture maintained at $-90°$ to $+40°$ C. and containing said ozonide, as a reducing compound trimethyl phosphite; and (c) recovering said 3-hydroxy-3-cephem 1-oxide compound from said mixture;

where in the above formulae $R_4$ is a carboxylic acid protecting ester forming group; and $R_3$ is hydrogen, $C_2$-$C_7$ alkanoyl, cyano-acetyl, haloacetyl, 5'-protected amino-5'-protected carboxyvaleryl; or an acyl group of the formula

wherein R" is phenyl, or phenyl substituted by halogen, hydroxy, nitro, amino, cyano, $C_1$-$C_4$-lower alkyl, $C_1$-$C_4$ lower alkoxy, hydroxymethyl, aminomethyl, carboxy or carboxymethyl;

or an arylalkanoyl group of the formula

wherein

R" is as defined above,

Y is O or S, and m is 0 or 1;

or a substituted arylakanoyl group of the formula

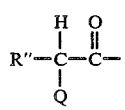

wherein

R' is as defined above and

Q is protected hydroxy.

18. The compound of claim 4, in the keto form of the formula

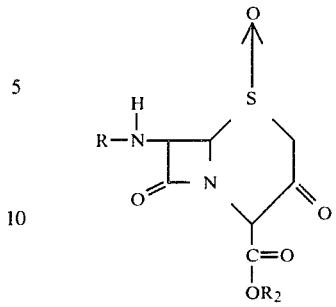

wherein R is as defined in claim 4, and $R_2$ is a carboxylic acid protecting ester forming group.

19. A member of the group consisting of p-nitrobenzyl-7-(D-phenylglycylamido)-3-hydroxy-3-cephem-carboxylate 1-oxide and the diphenylmethyl-7-(D-phenylglycylamido)-3-hydroxy-3-cephem-carboxylate 1-oxide.

20. A member selected from the group consisting of p-nitrobenzyl 7-phenylacetylamido-3-hydroxy-3-cephem-4-carboxylate 1-oxide and diphenylmethyl 7-phenylacetylamido-3-hydroxy-3-cephem-4-carboxylate 1-oxide.

21. A process for preparing a 3-hydroxy-3-cepham sulfoxide ester of the formula

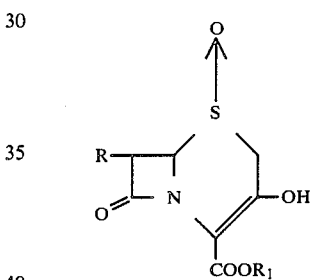

wherein R is $H_2N$, phthalimido, succinimido or an acylamido group of the formula

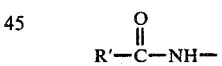

wherein

R' is hydrogen, $C_1$-$C_6$ alkyl-, cyanomethyl, halomethyl; or an acylamino group of the formula

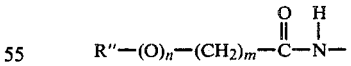

wherein

R" is phenyl, or phenyl substituted by halogen, $C_1$-$C_4$ lower alkoxy, and m and n are independently 0 or 1;

or R is a substituted arylacylamido group of the formula

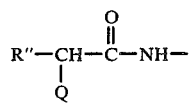

wherein
R" is phenyl or phenyl substituted by halogen and Q is protected hydroxy, protected amino, carboxy, or —SO₃H;
and R₁ is a carboxyl acid protecting group which comprises
(a) reacting in an inert solvent a 3-exomethylenecepham sulfoxide ester of the formula

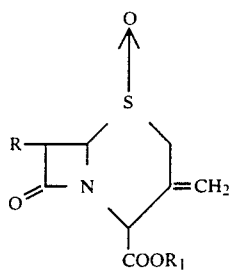

wherein R and R₁ have the same meaning as defined above, with ozone at a temperature between −90° and 40° C. and (b) decomposing the intermediate oxidation products.

22. The process of claim 21 wherein the intermediate oxidation products are decomposed with a reducing agent.

23. The process of claim 22 wherein the reducing agent is dimethyl sulfide.

24. The process of claim 22 wherein the reducing agent is a member selected from the group consisting of dimethyl sulfide and sulfur dioxide.

25. The process of claim 21 wherein the intermediate oxidation products are decomposed by slight warming.

26. The process of claim 21 wherein the reaction of the 3-exomethylenecepham sulfoxide ester with ozone is carried out in the presence of a protic solvent.

27. The process of claim 21 wherein R is phenoxy acetamido, phenylacetamido or phthalimido.

28. The process of claim 27 wherein the 3-exomethylenecepham sulfoxide ester is diphenylmethyl 7-phenylacetamido-3-exomethylenecepham-4-carboxylate-1-oxide.

29. The process of claim 21 wherein the 3-exomethylenecepham-sulfoxide ester in p-nitrobenzyl 7-phenoxyacetamido-3-exomethylenecepham-4-carboxylate-1-oxide, diphenylmethyl 7-phenylacetamido-3-exomethylenecepham-4-carboxylate-1-oxide or p-nitrobenzyl 7-phthalimido-3-exomethylenecepham-4-carboxylate-1-oxide.

30. The process of claim 21 wherein the reaction of the 3-exomethylenecepham sulfoxide ester with ozone is carried out in the presence of a solvent which is an alcohol or a ketone or a mixture of said solvents.

31. A compound of claim 12, said compound being diphenylmethyl 7-(D-phenylglycylamido)-3-hydroxy-3-cephem-4-carboxylate 1-oxide.

* * * * *